(12) United States Patent
Skerra et al.

(10) Patent No.: US 12,173,038 B2
(45) Date of Patent: Dec. 24, 2024

(54) HIGH AFFINITY ANTICALINS DIRECTED AGAINST HUMAN CD98HC

(71) Applicant: Technische Universität München, Munich (DE)

(72) Inventors: Arne Skerra, Dachau (DE); Friedrich-Christian Deuschle, Freising (DE); André Schiefner, Nuremberg (DE); Volker Morath, Munich (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 555 days.

(21) Appl. No.: 17/440,520

(22) PCT Filed: Mar. 18, 2020

(86) PCT No.: PCT/EP2020/057469
§ 371 (c)(1),
(2) Date: Sep. 17, 2021

(87) PCT Pub. No.: WO2020/193316
PCT Pub. Date: Oct. 1, 2020

(65) Prior Publication Data
US 2022/0153790 A1 May 19, 2022

(30) Foreign Application Priority Data
Mar. 28, 2019 (EP) .................... 19165966

(51) Int. Cl.
*A61K 38/16* (2006.01)
*C07K 14/47* (2006.01)
*A61K 38/00* (2006.01)

(52) U.S. Cl.
CPC .............. *C07K 14/47* (2013.01); *A61K 38/00* (2013.01); *C07K 2319/00* (2013.01)

(58) Field of Classification Search
None
See application file for complete search history.

(56) References Cited

FOREIGN PATENT DOCUMENTS

| EP | 2 510 357 B1 | 3/2016 |
|---|---|---|
| WO | 2008/022759 A2 | 2/2008 |
| WO | 2013/078377 A1 | 5/2013 |
| WO | 2020/193316 A1 | 10/2020 |

OTHER PUBLICATIONS

International Search Report and Written Opinion mailed on Apr. 21, 2020 in International Patent Application No. PCT/EP2020/057469, filed on Mar. 18, 2020, 15 pages.
Abou et al., "In Vivo Biodistribution and Accumulation of Zr-89 in Mice", Nuclear Medicine and Biology, Jul. 2011, 38(5):675-681.
Altschul et al., "Gapped BLAST and PSI-BLAST: A New Generation of Protein Database Search Programs", Nucleic Acids Research, Sep. 1997, 25(17):3389-3402.
Altshuler et al., "Generation of Recombinant Antibodies and Means for Increasing their Affinity", Biochemistry (Moscow), Dec. 2010, 75(13):1584-1605.
Ansari et al., "The Multifunctional Solute Carrier 3A2 (SLC3A2) Confers a Poor Prognosis in the Highly Proliferative Breast Cancer Subtypes", British Journal of Cancer, 2018, 118:1115-1122.
Baas "Light It Up", Science-Business exchange, 2014, 7:2 pages.
Bagshawe K.D. "Targeting: The ADEPT Story So Far", Current Drug Targets, 2009, 10(2):152-157.
Bajaj et al., "CD98-mediated Adhesive Signaling Enables the Establishment and Propagation of Acute Myelogenous Leukemia", Cancer Cell, 2016, 30(5):792-805.
Barinka et al., "Selection and Characterization of Anticalins Targeting Human Prostate-Specific Membrane Antigen (PSMA)", Protein Engineering, Design and Selection, Mar. 2016, 29(3)105-115.
Barkovskiy et al., "An Engineered Lipocalin That Tightly Complexes the Plant Poison Colchicine for Use as Antidote and in Bioanalytical Applications", Biological Chemistry, 2019, 400(3):351-366.
Barollo "Overexpression of L-Type Amino Acid Transporter 1 (LAT1) and 2 (LAT2): Novel Markers of Neuroendocrine Tumors", Plos One, May 25, 2016, 14 pages.
Beckett et al., "A Minimal Peptide Substrate in Biotin Holoenzyme Synthetase-Catalyzed Biotinylation", Protein Science, 1999, 8:921-929.
Bertschinger et al., "Selection of Single Domain Binding Proteins by Covalent DNA Display", Protein Engineering, Design & Selection, 2007, 20(2):57-68.
Binder et al., "High-Throughput Sorting of an Anticalin Library via EspP-Mediated Functional Display on the *Escherichia coli* Cell Surface", Journal of Molecular Biology, Jul. 2010, 400(4):783-802.
Binder et al., "PASylation®: A Versatile Technology to Extend Drug Delivery", Current Opinion in Colloid & Interface Science, 2017, 31:10-17.
Bixby et al., "A Phase I Study of IGN523, a Novel Anti-CD98 Monoclonal Antibody in Patients with Relapsed or Refractory Acute Myeloid Leukemia (AML)", Blood, 2015, 126(23):3809.
Braasch et al., "Locked Nucleic Acid (LNA): Fine-Tuning the Recognition of DNA and RNA", Chemistry & Biology, 2001, 8:1-7.
Broer et al., "The Heterodimeric Amino Acid Transporter 4F2hc/y+LAT2 Mediates Arginine Efflux in Exchange with Glutamine", Biochemical Journal, 2000, 349:787-795.
Browne et al., "Selection Methods for High-Producing Mammalian Cell Lines", Trends Biotechnology, 2007, 25(9):425-432.
Cantor et al., "CD98 at the Crossroads of Adaptive Immunity and Cancer", Journal of Cell Science, 2012, 125:1373-1382.
Cantor et al., "Integrin-Associated Proteins as Potential Therapeutic Targets", Immunological Reviews, Pages, Jun. 2008, 223(1):236-251.
Cetin et al., "RasIns: Genetically Encoded Intrabodies of Activated Ras Proteins", Journal of Molecular Biology, 2017, 429(4):562-573.
Chen et al., "A Humanized Immunoenzyme with Enhanced Activity for Glucuronide Prodrug Activation in the Tumor Microenvironment", Bioconjugate Chemistry, 2011, 22:938-948.

(Continued)

*Primary Examiner* — Fred H Reynolds
(74) *Attorney, Agent, or Firm* — LOZA & LOZA LLP

(57) ABSTRACT

The present invention relates to a cluster of differentiation 98 heavy chain (CD98hc)-specific binding protein, wherein the CD98hc-specific binding protein is a lipocalin 2 (Lcn2)-derived binding protein and binds to CD98hc with a $K_D$ of 200 nM or lower.

Figure 1:
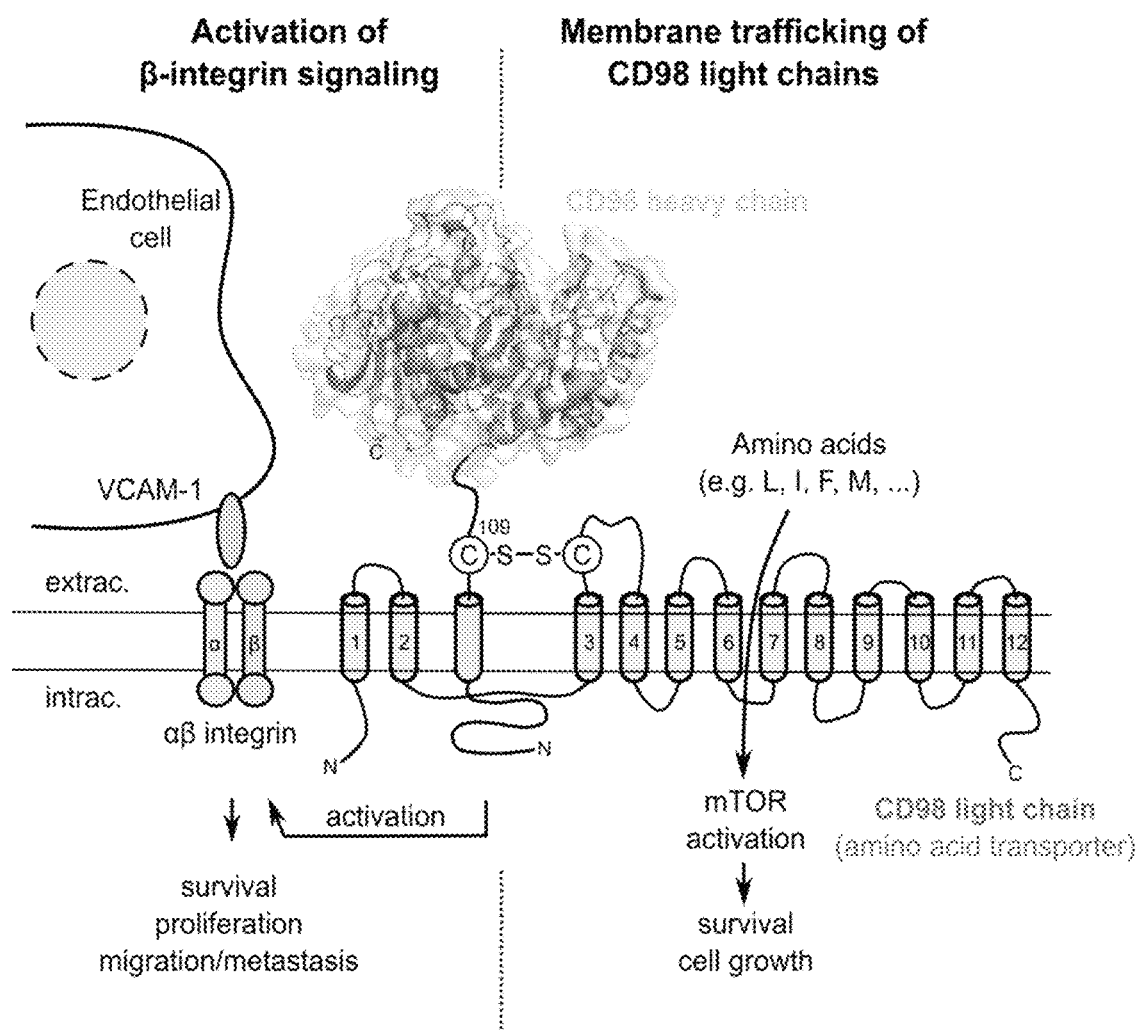

11 Claims, 28 Drawing Sheets
Specification includes a Sequence Listing.

(56) References Cited

OTHER PUBLICATIONS

Costa et al., "Stable Expression of the Golgi Form and Secretory Variants of Human Fucosyltransferase III from BHK-21 Cells", The Journal of Biological Chemistry, Apr. 25, 1997, 272(17):11613-11621.

De Jong et al., "Receptor-Ligand Binding Assays: Technologies and Applications", Journal of Chromatography B, 2005, 829(1-2):1-25.

Diem et al., "Selection of High-Affinity Centyrin FN3 Domains from a Simple Library Diversified at a Combination of Strand and Loop Positions", Protein Engineering, Design & Selection, 2014, 27(10):419-429.

Digomann et al., "The CD98 Heavy Chain Is a Marker and Regulator of Head and Neck Squamous Cell Carcinoma Radiosensitivity", Clinical Cancer Research, 2019, 25:3152-3163.

Emsley et al., "Features and Development of COOT", Acta Crystallographica Section D Biological Crystallography, 2010, D66:486-501.

Feldwisch et al., "Engineering of Affibody Molecules for Therapy and Diagnostics", Methods in Molecular Biology, Chapter 7, 2012, 899:103-126.

Fischer et al., "Zr-89, a Radiometal Nuclide with High Potential for Molecular Imaging with PET: Chemistry, Applications and Remaining Challenges", Molecules, 2013, 18:6469-6490.

Fort et al., "The Ectodomains of rBAT and 4F2hc Are Fake or Orphan α-Glucosidases", Molecules, 2021, 26(20):6231.

Fotiadis et al., "The SLC3 and SLC7 Families of Amino Acid Transporters", Molecular Aspects of Medicine, Apr.-Jun. 2013, 34(2-3):139-158.

Friedrich et al., "Selection of an Anticalin® Against the Membrane Form of Hsp70 via Bacterial Surface Display and Its Theranostic Application in Tumour Models", Biological Chemistry, 2018, 399:235-252.

Fukasawa et al., "Identification and Characterization of a Na+-independent Neutral Amino Acid Transporter That Associates with the 4F2 Heavy Chain and Exhibits Substrate Selectivity for Small Neutral d- and I-Amino Acids", Journal of Biological Chemistry, 2000, 275(13):9690-9698.

Furuya et al., "Correlation of L-Type Amino Acid Transporter 1 and CD98 Expression with Triple Negative Breast Cancer Prognosis", Cancer Science, Feb. 2012, 103(2):382-389.

Garousi et al., "ADAPT, a Novel Scaffold Protein-Based Probe for Radionuclide Imaging of Molecular Targets That Are Expressed in Disseminated Cancers", Cancer Research, 2015, 75(20):4364-4371.

Gebauer et al., "Anticalins Small Engineered Binding Proteins Based on the Lipocalin Scaffold", Methods Enzymology, 2012, 503:157-188.

Gebauer et al., "Combinatorial Design of an Anticalin Directed against the Extra-Domain B for the Specific Targeting of Oncofetal Fibronectin", Journal of Molecular Biology, 2013, 425:780-802.

Gebauer et al., "Engineered Protein Scaffolds as Next-Generation Antibody Therapeutics", Current Opinion in Chemical Biology, 2009, 13:245-255.

Geisse et al., "Transient Expression Technologies: Past, Present, and Future", Methods in Molecular Biology, 2012, 899:203-219.

Genbank "*Homo sapiens* Lipocalin 2 (LCN2), mRNA", NCBI Reference Sequence: NM_005564.4, Sep. 29, 2015, 3 pages.

Grabulovski et al., "A Novel, Non-immunogenic Fyn SH3-derived Binding Protein with Tumor Vascular Targeting Properties", The Journal of Biological Chemistry, Feb. 2, 2007, 282:3196-3204.

Gross et al., "Recombinant Probes for Visualizing Endogenous Synaptic Proteins in Living Neurons", Neuron, 2013, 78(6):971-985.

Hadpech et al., "Alpha-helicoidal HEAT-like Repeat Proteins (αRep) Selected as Interactors of HIV-1 Nucleocapsid Negatively Interfere with Viral Genome Packaging and Virus Maturation", Scientific Reports, Nov. 27, 2017, 7(16335):19 pages.

Hayashi et al., "Novel Therapeutic Approaches Targeting L-Type Amino Acid Transporters for Cancer Treatment", World Journal of Gastrointestinal Oncology, Jan. 15, 2017, 9(1):21-29.

Heinrich et al., "Comparison of the Results Obtained by ELISA and Surface Plasmon Resonance for the Determination of Antibody Affinity", Journal of Immunological Methods, Jan. 2010, 352(1-2):13-22.

Henderson et al., "CD98hc (SLC3A2) Interaction with β1 Integrins Is Required for Transformation", Journal of Biological Chemistry, Dec. 24, 2004, 279(52):54731-54741.

Henikoff et al., "Amino Acid Substitution Matrices from Protein Blocks", Proceedings of the National Academy of Sciences, Nov. 1992, 89(22):10915-10919.

Holliger et al., "Engineered Antibody Fragments and the Rise of Single Domains", Nature Biotechnology, Oct. 2005, 23(9):1126-1135.

Ikotun et al., "Imaging the L-Type Amino Acid Transporter-1 (LAT1) with Zr-89 ImmunoPET", PlosOne, Oct. 2013, 8(10):e77476:9 pages.

Isoda et al., "Expression of L-Type Amino Acid Transporter 1 (LAT1) as a Prognostic and Therapeutic Indicator in Multiple Myeloma", Cancer Science, Nov. 2014, 105(11):1496-1502.

Ji et al., "xCT (SLC7A11)-Mediated Metabolic Reprogramming Promotes Non-Small Cell Lung Cancer Progression", Oncogene, 2018, 37:5007-5019.

Johnson et al., "Kabat Database and Its Applications: 30 Years After the First Variability Plot", Nucleic Acids Research, Jan. 2000, 28(1):214-218.

Kabsch et al., "XDS", Acta Crystallographica Section D Biological Crystallography, 2010, D66:125-132.

Kaira et al., "CD98 Expression Is Associated with Poor Prognosis in Resected Non-Small-Cell Lung Cancer with Lymph Node Metastases", Annals of Surgical Oncology, Sep. 2009, 16:3473-3481.

Kaira et al., "Expression of 4F2hc (CD98) in Pulmonary Neuroendocrine Tumors", Oncology Reports, 2011, 26:931-937.

Kaira et al., "L-Type Amino Acid Transporter 1 and CD98 Expression in Primary and Metastatic Sites of Human Neoplasms", Cancer Science, 2008, 99(12):2380-2386.

Kaira et al., "Prognostic Significance of L-Type Amino Acid Transporter 1 (LAT1) and 4F2 Heavy Chain (CD98) Expression in Surgically Resectable Stage III Non-Small Cell Lung Cancer", Experimental and Therapeutic Medicine, 2010, 1:799-808.

Kanai et al., "Expression Cloning and Characterization of a Transporter for Large Neutral Amino Acids Activated by the Heavy Chain of 4F2 Antigen (CD98)", Journal of Biological Chemistry, Sep. 11, 1998, 273(37):23629-23632.

Koide et al., "The Fibronectin Type III Domain as a Scaffold for Novel Binding Proteins", Journal of Molecular Biology, 1998, 284(4):1141-1151.

Konermann et al., "Bispecific Antibodies", Drug Discovery Today, 2015, 20(7):838-847.

Krause et al., "PET Imaging of Gliomas Using Novel Tracers: A Sleeping Beauty Waiting to Be Kissed", Expert Review of Anticancer Therapy, 2010, 10:609-613.

Lee et al., "Design of a Binding Scaffold Based on Variable Lymphocyte Receptors of Jawless Vertebrates by Module Engineering", Proceedings of the National Academy of Sciences, Feb. 28, 2012, 109(9):3299-3304.

Matasci et al., "Recombinant Therapeutic Protein Production in Cultivated Mammalian Cells: Current Status and Future Prospects", Drug Discovery Today: Technologies, 2008, 5(2-3):e37-e42.

Matthews et al., "Enhanced Protein Thermostability from Site-Directed Mutations That Decrease the Entropy of Unfolding", Proceedings of the National Academy of Sciences, Oct. 1987, 84:6663-6667.

Mendler et al., "Zr-Labeled Versus [124]I-Labeled αHER2 Fab with Optimized Plasma Half-Life for High-Contrast Tumor Imaging In Vivo", Journal of Nuclear Medicine, Jul. 2015, 56(7):1112-1118.

Miyamoto et al., "Physical Association and Functional Interaction Between Beta1 Integrin and CD98 on Human T Lymphocytes", Molecular Immunology, Jan. 2003, 39(12):739-751.

Mourato et al., "Ribosome Display for the Selection of Sac7d Scaffolds", Methods in Molecular Biology, 2012, 805:315-331.

(56) References Cited

OTHER PUBLICATIONS

Murshudov et al., "REFMAC5 for the Refinement of Macromolecular Crystal Structures", Acta Crystallographica Section D Biological Crystallography, 2011, D67:355-367.

Nakamura et al., "4F2 (CD98) Heavy Chain Is Associated Covalently with an Amino Acid Transporter and Controls Intracellular Trafficking and Membrane Topology of 4F2 Heterodimer*", Journal of Biological Chemistry, Jan. 29, 1999, 274(5):3009-3016.

Nakanishi et al., "Expression of LAT1 Predicts Risk of Progression of Transitional Cell Carcinoma of the Upper Urinary Tract", Virchows Archiv, 2007, 451:681-690.

Nicklin et al., "Bidirectional Transport of Amino Acids Regulates mTOR and Autophagy", Cell, Feb. 6, 2009, 136(3):521-534.

Nielsen et al., "Therapeutic Efficacy of Anti-ErbB2 Immunoliposomes Targeted by a Phage Antibody Selected for Cellular Endocytosis", Biochimica et Biophysica Acta, 2002, 1591(1-3):109-118.

Orr et al., "Elucidating the Multi-Targeted Anti-Amyloid Activity and Enhanced Islet Amyloid Polypeptide Binding of β-Wrapins", Computers & Chemical Engineering, Aug. 2018, 116:322-332.

Owens et al., "Identification of Two Short Internal Ribosome Entry Sites Selected from Libraries of Random Oligonucleotides", Proceedings of the National Academy of Sciences, Feb. 13, 2001, 98(4):1471-1476.

Painter et al., "TLSMD Web Server for the Generation of Multi-Group TLS Models", Journal of Applied Crystallography, 2006, 39:109-111.

Papetti et al., "Controlling Tumor-Derived and Vascular Endothelial Cell Growth Role of the 4F2 Cell Surface Antigen", American Journal of Pathology, Jul. 2001, 159(1):165-178.

Pearson et al., "Improved Tools for Biological Sequence Comparison", PNAS, Apr. 1988, 85(8):2444-2448.

Pham et al., "Large-Scale Transfection of Mammalian Cells for the Fast Production of Recombinant Protein", Molecular Biotechnology, 2006, 34:225-237.

Pineda et al., "Identification of a Membrane Protein, LAT-2, That Co-Expresses with 4F2 Heavy Chain, an L-Type Amino Acid Transport Activity with Broad Specificity for Small and Large Zwitterionic Amino Acids", Journal of Biological Chemistry, 1999, 274(28):19738-19744.

Prager et al., "CD98hc (SLC3A2), a Novel Marker in Renal Cell Cancer", European Journal of Clinical Investigation, 2009, 39(4):304-310.

Rauth et al., "High-Affinity Anticalins with Aggregation-Blocking Activity Directed Against the Alzheimer β-Amyloid Peptide", Biochemical Journal, 2016, 473(11):1563-1578.

Richter et al., "Anticalins Directed Against Vascular Endothelial Growth Factor Receptor 3 (VEGFR-3) with Picomolar Affinities Show Potential for Medical Therapy and in Vivo Imaging", Biological Chemistry, 2017, 398(1):39-55.

Richter et al., "Anticalins: Exploiting a Non-Ig Scaffold with Hypervariable Loops for the Engineering of Binding Proteins", FEBS Letters, 2014, 588:213-218.

Rietbergen et al., "Cancer Stem Cell Enrichment Marker CD98: A Prognostic Factor for Survival in Patients with Human Papillomavirus-Positive Oropharyngeal Cancer", European Journal of Cancer, Dec. 2013, 50(4):765-773.

Rothe et al., "Anticalin® Proteins as Therapeutic Agents in Human Diseases", BioDrugs, 2018, 32:233-243.

Salisbury et al., "The Regulation and Function of the L-Type Amino Acid Transporter 1 (LAT1) in Cancer", International Journal of Molecular Sciences, Aug. 2018, 19(2373):10 pages.

Salter et al., "Prognostic Significance of Activation and Differentiation Antigen Expression in B-Cell Non-Hodgkin's Lymphoma", The Journal of Pathology, 1989, 159(3):211-220.

Sato et al., "Cloning and Expression of a Plasma Membrane Cystine/Glutamate Exchange Transporter Composed of Two Distinct Proteins", Journal of Biological Chemistry, 1999, 274(17):11455-11458.

Schiefner et al., "Anticalins Reveal High Plasticity in the Mode of Complex Formation with a Common Tumor Antigen", Structure, Apr. 3, 2018, 26:649-656.

Schiefner "The Menagerie of Human Lipocalins: A Natural Protein Scaffold for Molecular Recognition of Physiological Compounds", Accounts of Chemical Research, Mar. 10, 2015, 48(4):976-985.

Schlapschy et al., "PASylation: A Biological Alternative to PEGylation for Extending the Plasma Half-Life of Pharmaceutically Active Proteins", Protein Engineering, Design & Selection, 2013, 26(8):489-501.

Schlatter et al., "Generation, Characterization and Structural Data of Chymase Binding Proteins Based on the Human Fyn Kinase SH3 Domain", MAbs, Jul./Aug. 2012, 4(4):497-508.

Schlehuber et al., "Tuning Ligand Affinity, Specificity, and Folding Stability of an Engineered Lipocalin Variant—a So-Called 'Anticalin'—Using a Molecular Random Approach", Biophysical Chemistry, May 2, 2002, 96(2-3):213-228.

Singh et al., "Insights into the Structure, Function, and Ligand Discovery of the Large Neutral Amino Acid Transporter 1, LAT1", International Journal of Molecular Sciences, 2018, 19(5): 1278.

Strohl William R., "Optimization of Fc-Mediated Effector Functions of Monoclonal Antibodies", Current Opinion in Biotechnology, 2009, 20(6):685-691.

Sugano et al., "Expression of xCT as a Predictor of Disease Recurrence in Patients with Colorectal Cancer", Anticancer Research, Feb. 2015, 35(2):677-682.

Summer et al., "Cyclic versus Noncyclic Chelating Scaffold for 89Zr-Labeled ZEGFR:2377 Affibody Bioconjugates Targeting Epidermal Growth Factor Receptor Overexpression", Molecular Pharmaceutics, 2018, 15:175-185.

Summer et al., "Exploiting the Concept of Multivalency with 68Ga- and 89Zr-Labelled Fusarinine C-Minigastrin Bioconjugates for Targeting CCK2R Expression", Contrast Media & Molecular Imaging, 2018, 2018(3171794):12 pages.

Thompson et al., "CLUSTAL W: Improving the Sensitivity of Progressive Multiple Sequence Alignment Through Sequence Weighting, Position-Specific Gap Penalties and Weight Matrix Choice", Nucleic Acids Research, 1994, 22(22):4673-4680.

Tiede et al., "Adhiron: A Stable and Versatile Peptide Display Scaffold for Molecular Recognition Applications", Protein Engineering, Design & Selection, 2014, 27(5):145-155.

Tiede et al., "Affimer Proteins Are Versatile and Renewable Affinity Reagents", eLife, 2017, 35 pages.

Torrents et al., "Identification and Characterization of a Membrane Protein (y+L Amino Acid Transporter-1) That Associates with 4F2hc to Encode the Amino Acid Transport Activity y+L. a Candidate Gene for Lysinuric Protein Intolerance", Journal of Biological Chemistry, 1998, 273(49):32437-32445.

Toyoda et al., "CD98 as a Novel Prognostic Indicator for Patients with Stage III/IV Hypopharyngeal Squamous Cell Carcinoma", Nov. 2015, 37(11):1569-1574.

Vosjan et al., "Conjugation and Radiolabeling of Monoclonal Antibodies with Zirconium-89 for PET Imaging Using the Bifunctional Chelate P-Isothiocyanatobenzyl-Desferrioxamine", Nature Protocols, 2010, 5:739-743.

Wang et al., "L-Type Amino Acid Transport and Cancer: Targeting the MTORC1 Pathway to Inhibit Neoplasia", American Journal of Cancer Research, 2015, 5(4):1281-1294.

Wang et al., "Targeting Amino Acid Transport in Metastatic Castration-Resistant Prostate Cancer: Effects on Cell Cycle, Cell Growth, and Tumor Development", Journal of the National Cancer Institute, 2013, 105(19):1463-1473.

Weidle et al., "The Emerging Role of New Protein Scaffold-based Agents for Treatment of Cancer", Cancer Genomics Proteomics, 2013, 10(4):155-168.

Weidle et al., "The Intriguing Options of Multispecific Antibody Formats for Treatment of Cancer", Cancer Genomics Proteomics, Feb. 2013, 10:1-18.

Wollscheid et al., "Mass-Spectrometric Identification and Relative Quantification of N-Linked Cell Surface Glycoproteins", Nature Biotechnology, Apr. 2009, 27(4):378-386.

(56) References Cited

OTHER PUBLICATIONS

Wurm F.M. "Production of Recombinant Protein Therapeutics in Cultivated Mammalian Cells", Nature Biotechnology, 2004, 22:1393-1398.

Yang et al., "Bridge Linkage Role Played by CD98hc of Anti-Tumor Drug Resistance and Cancer Metastasis on Cisplatin-Resistant Ovarian Cancer Cells", Cancer Biology & Therapy, Jun. 2007, 6(6):942-947.

Yoshida Go J. "Metabolic Reprogramming: The Emerging Concept and Associated Therapeutic Strategies", Journal of Experimental & Clinical Cancer Research, 2015, 34(111):11 pages.

Zent et al., "Class- and Splice Variant-Specific Association of CD98 with Integrin Beta Cytoplasmic Domains", Journal of Biological Chemistry, 2000, 275(7):5059-5064.

Zuchero et al., "Discovery of Novel Blood-Brain Barrier Targets to Enhance Brain Uptake of Therapeutic Antibodies", Neuron, Jan. 6, 2016, 70-82.

Hacker et al., "Polyethyleneimine-Based Transient Gene Expression Processes for Suspension-Adapted HEK-293E and CHO-DG44 Cells", Protein Expression and Purification, 2013, 92(1):67-76.

Hayes et al., "Antitumor Activity of an anti-CD98 Antibody", International Journal of Cancer, 2015, 137(3):710-720.

Hutterer et al., "[18F]-Fluoro-Ethyl-L-Tyrosine PET: A Valuable Diagnostic Tool in Neuro-Oncology, but Not All That Glitters Is Glioma", Neuro-Oncology, 2013, 15(3):341-351.

Li et al., "Metastasis-Associated in Colon Cancer 1: A Promising Biomarker for the Metastasis and Prognosis of Colorectal Cancer", Oncology Letters, 2017, 14(4):3899-3908.

McCoy et al., "Phaser Crystallographic Software", Journal of Applied Crystallography, 2007, 40(Pt 4):658-674.

Mendler et al., "High Contrast Tumor Imaging with Radio-Labeled Antibody Fab Fragments Tailored for Optimized Pharmacokinetics via PASylation", MAbs, 2015, 7(1):96-109.

Mueller et al., "Facilities for macromolecular crystallography at the Helmholtz-Zentrum Berlin", Journal of Synchrotron Radiation, 2012, 19(Pt 3):442-449.

UniProt "Neutrophil Gelatinase-Associated Lipocalin", UniProtKB—P80188, 10 pages downloaded Jul. 10, 2024.

A

Figure 1 – continued
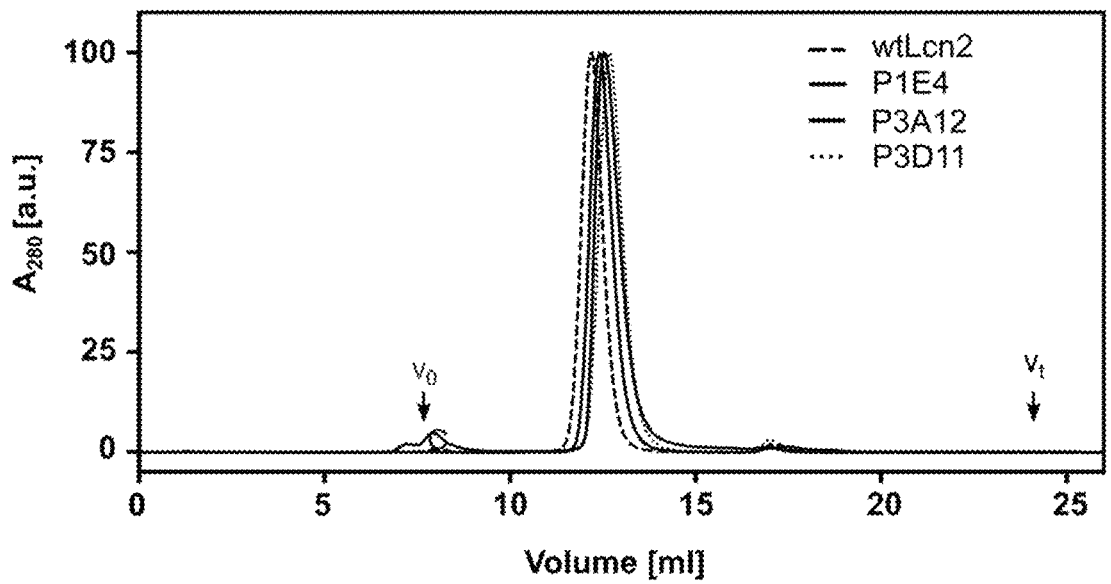
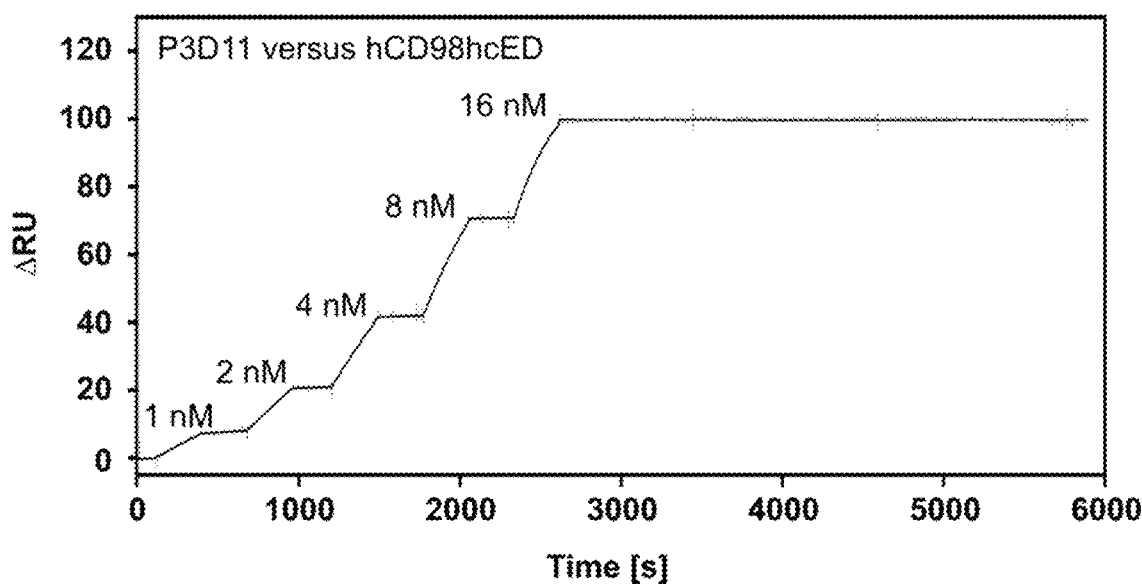

A

B

C

Figure 4:
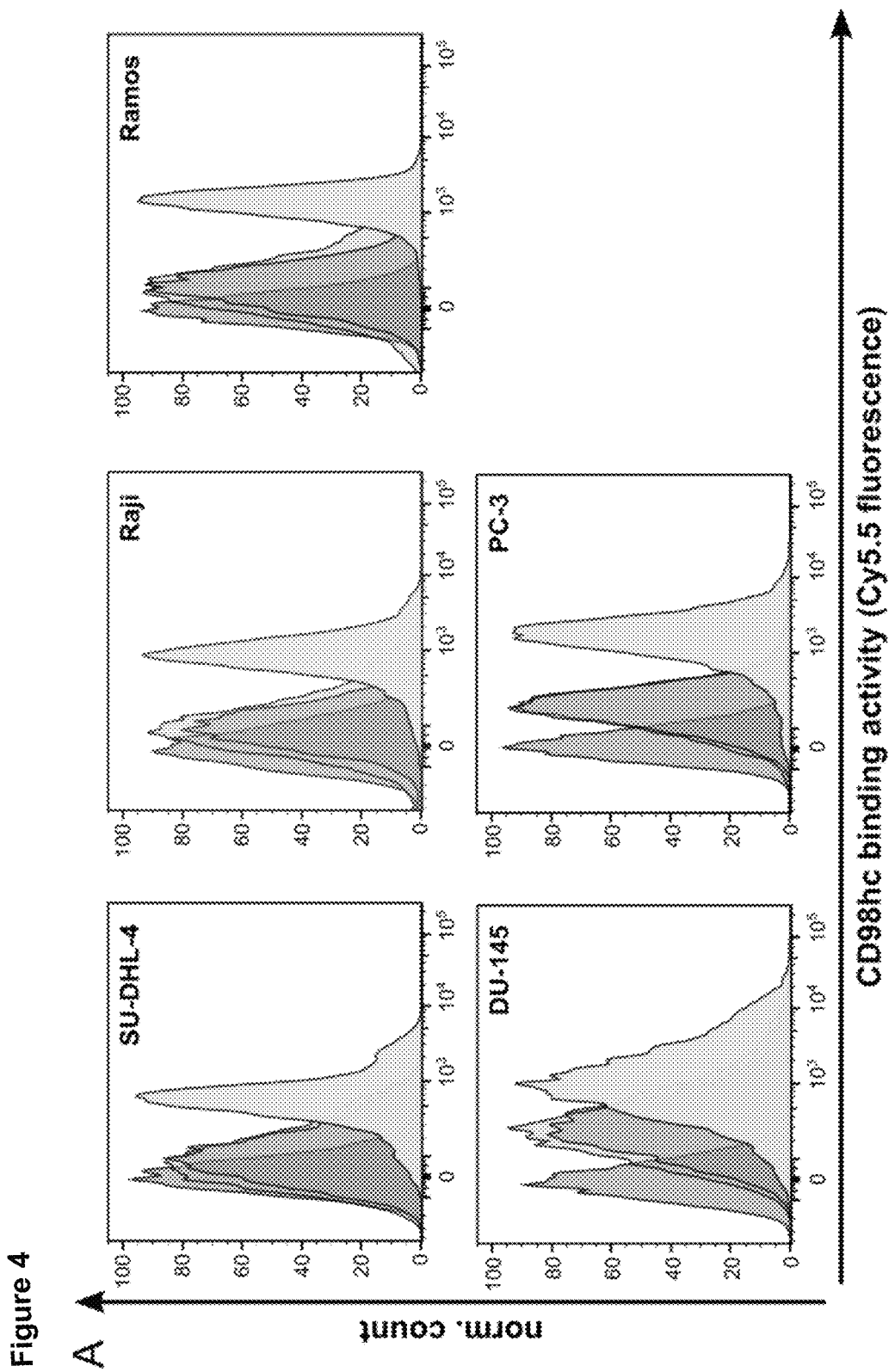

Figure 4 – continued
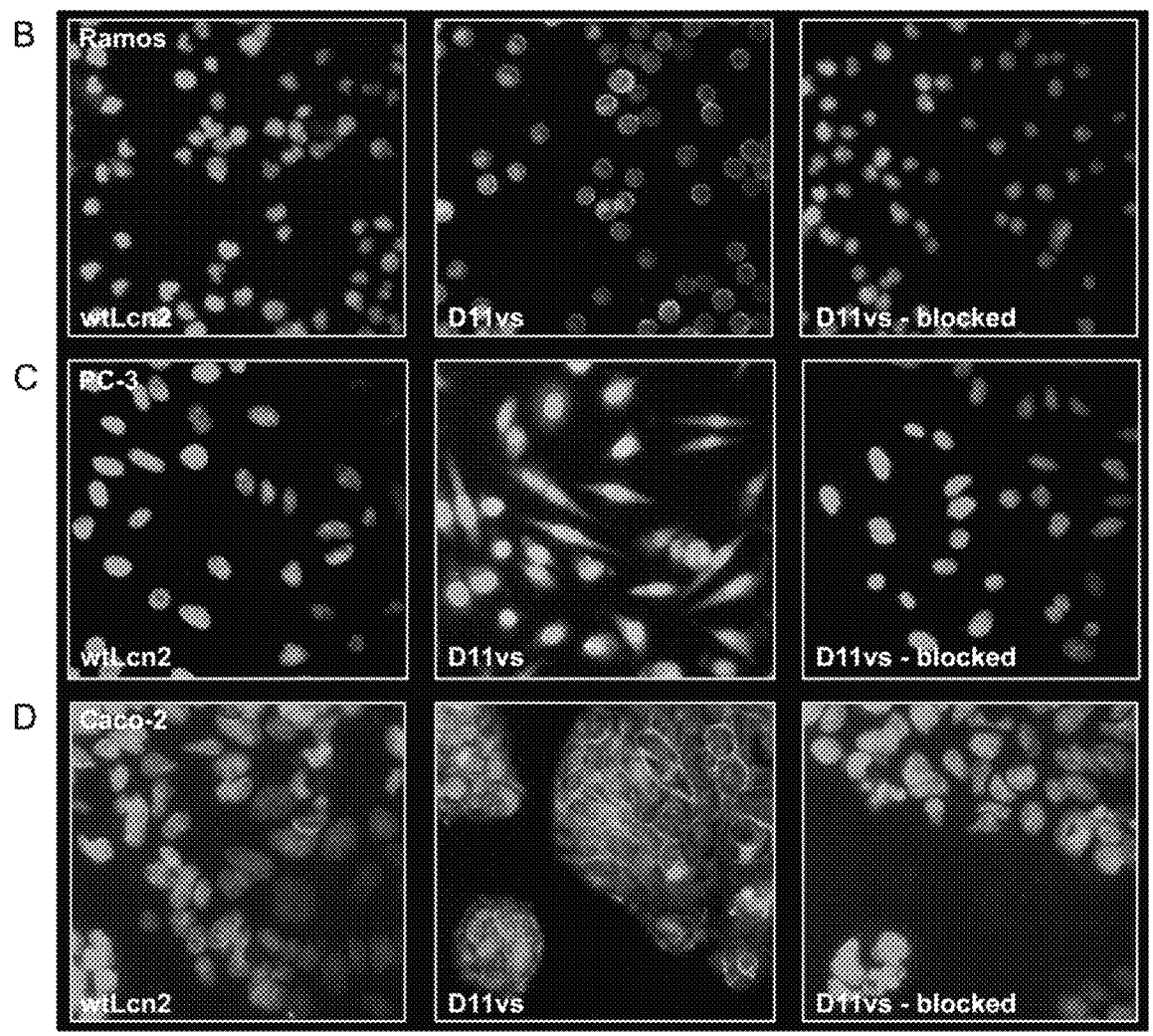

Figure 5:
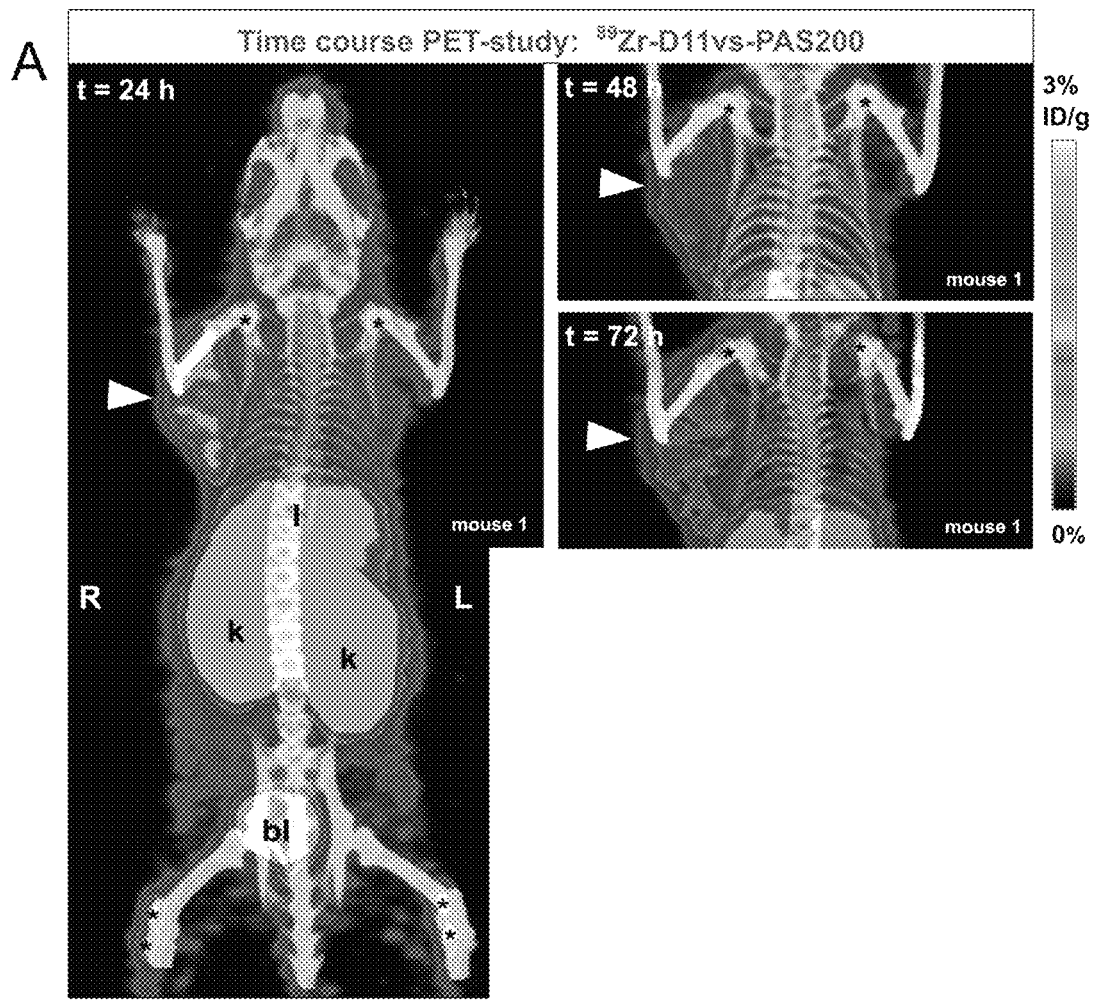
Figure 5:
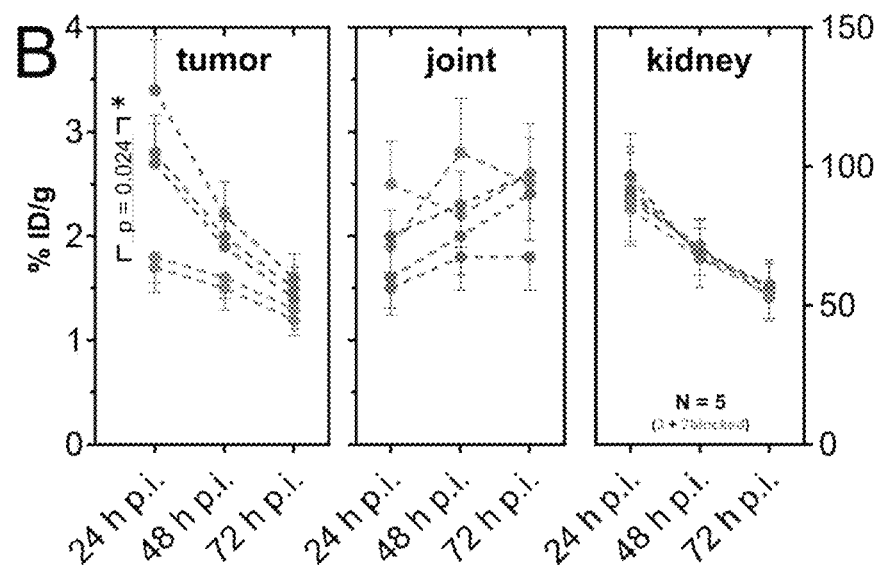

Figure 5 - continued
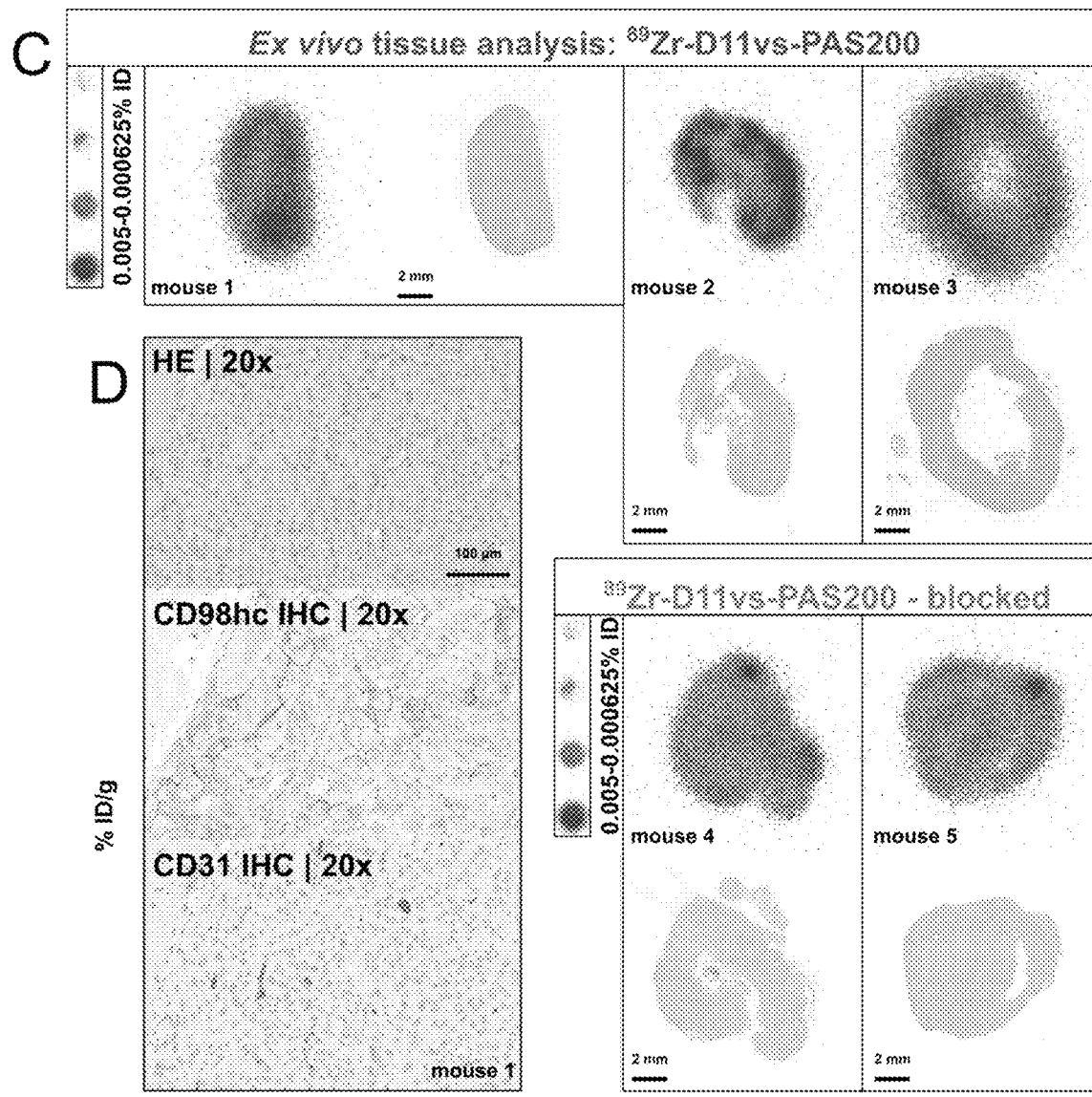

Figure 6:
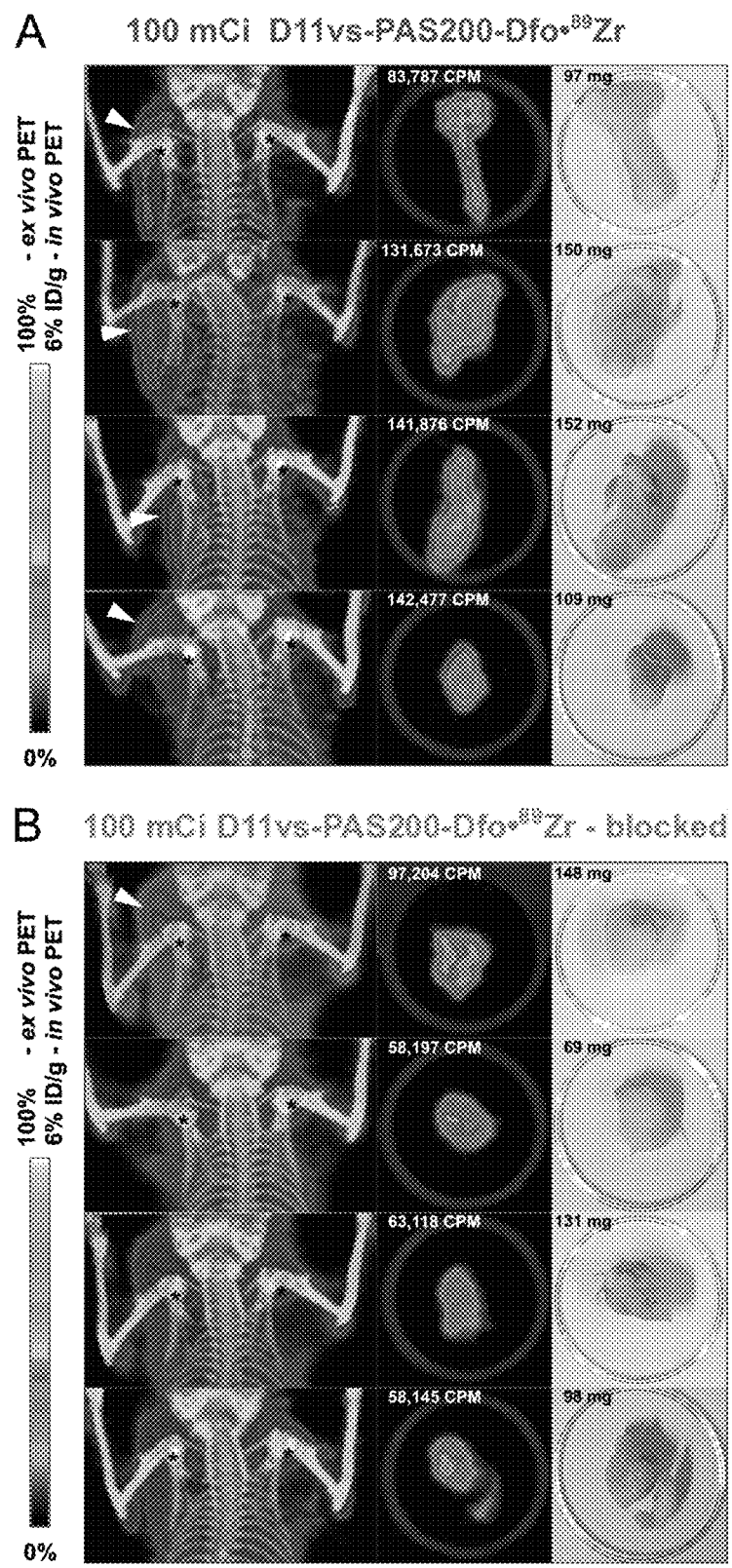

Figure 6 – continued
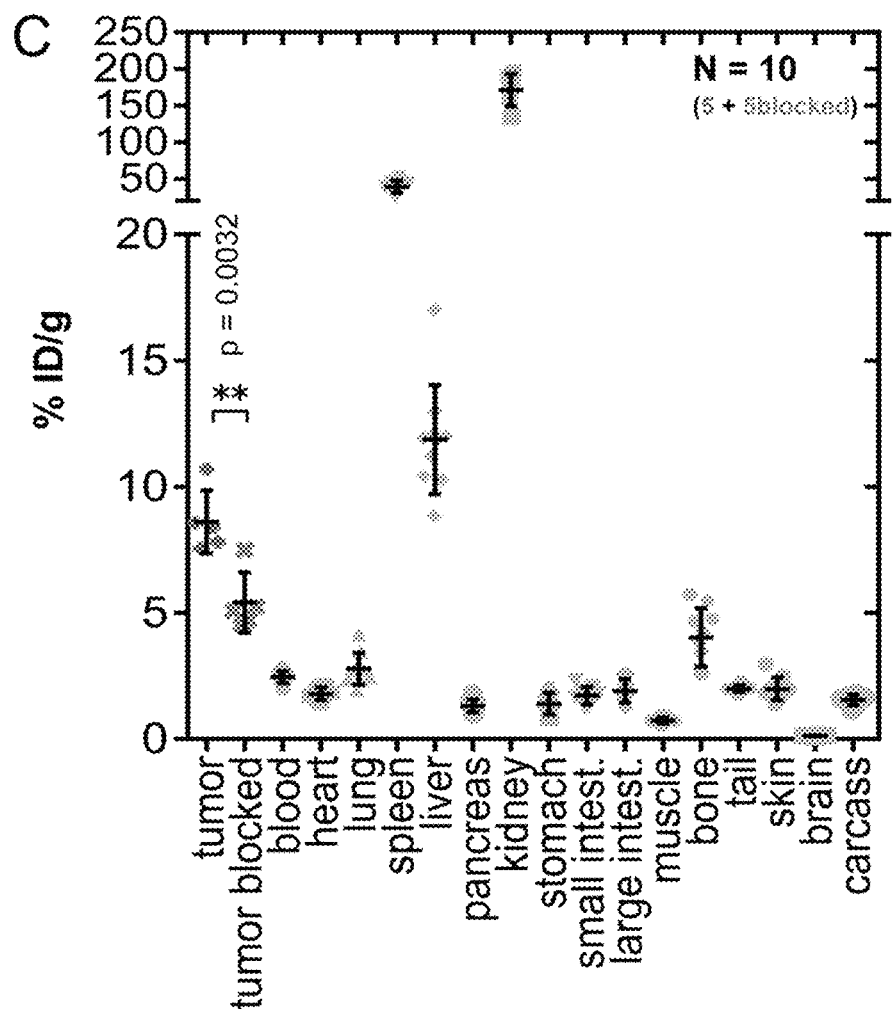

Figure 7:
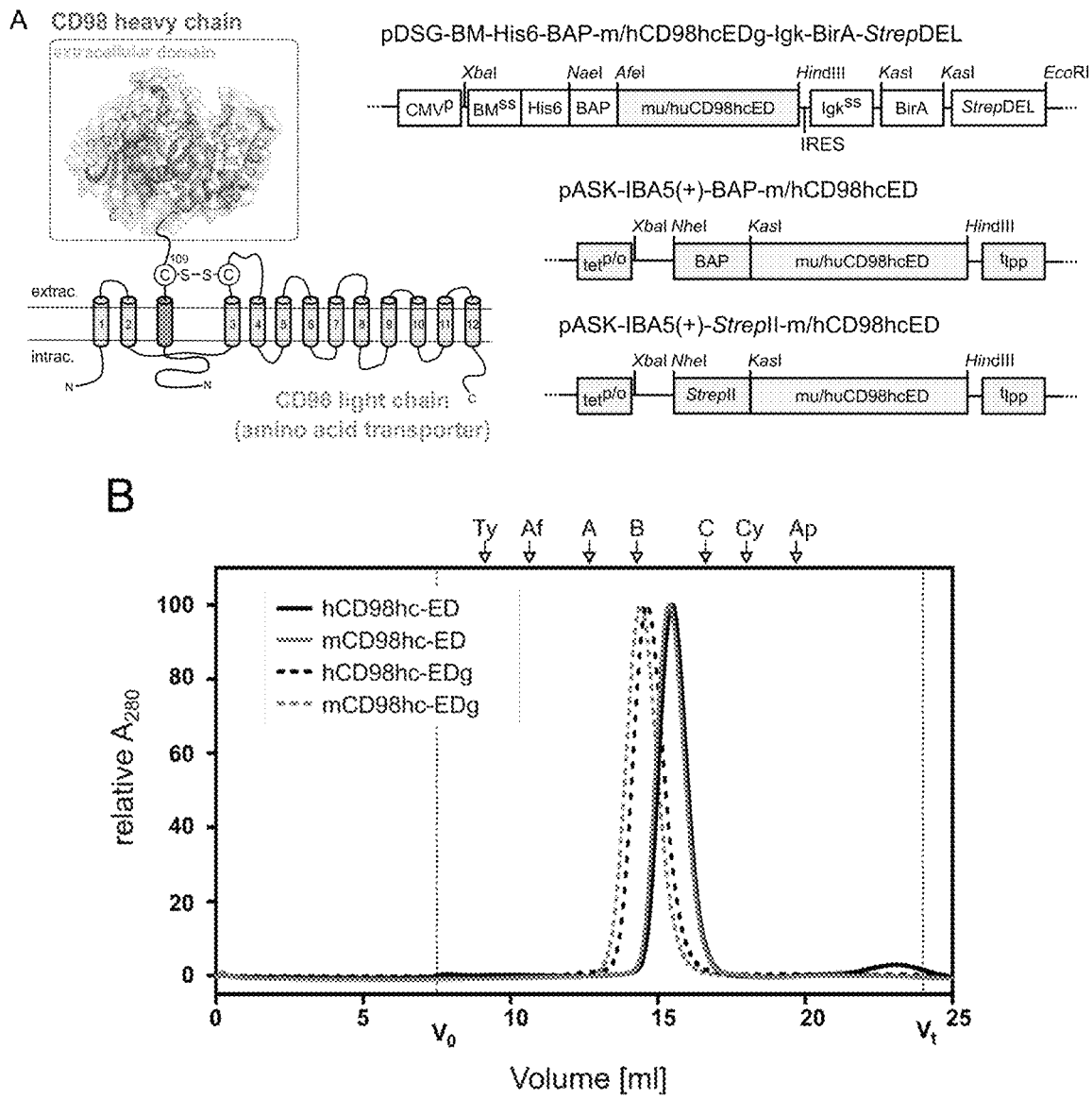

Figure 7 – continued
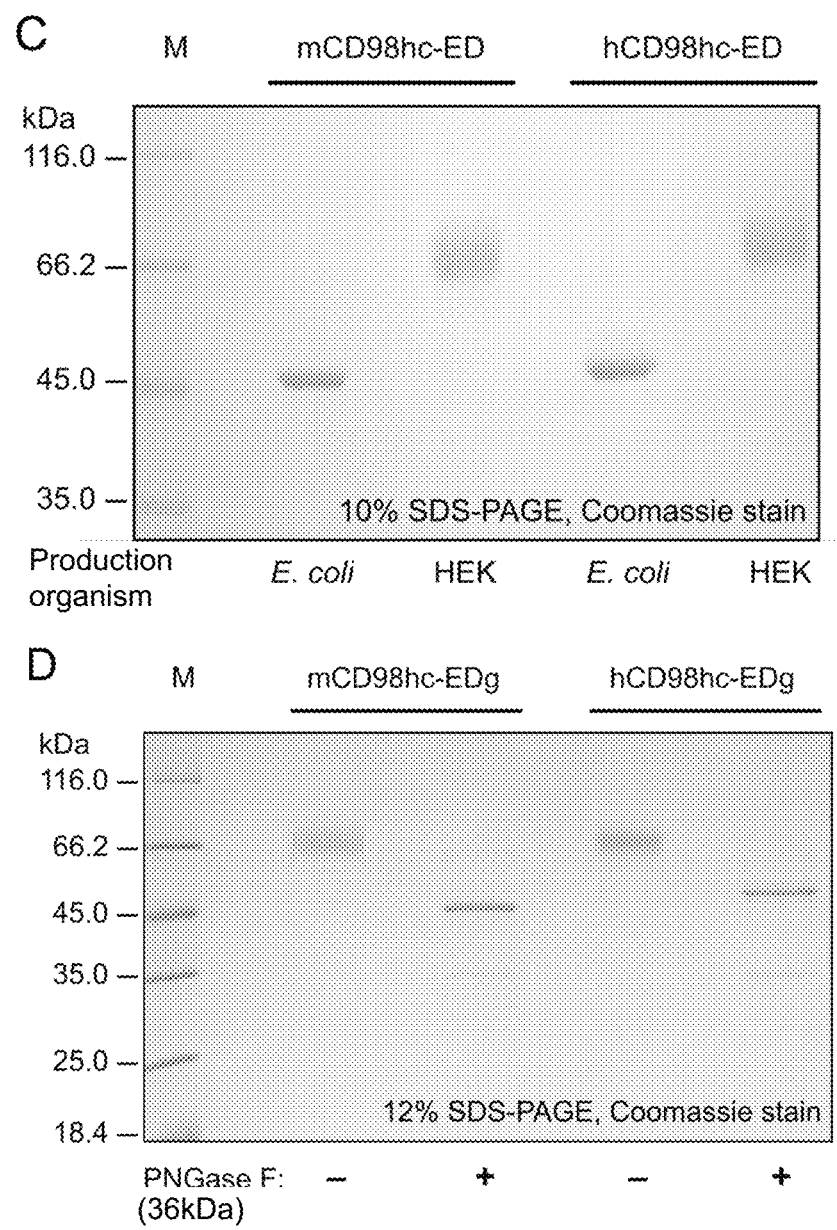

Figure 8:
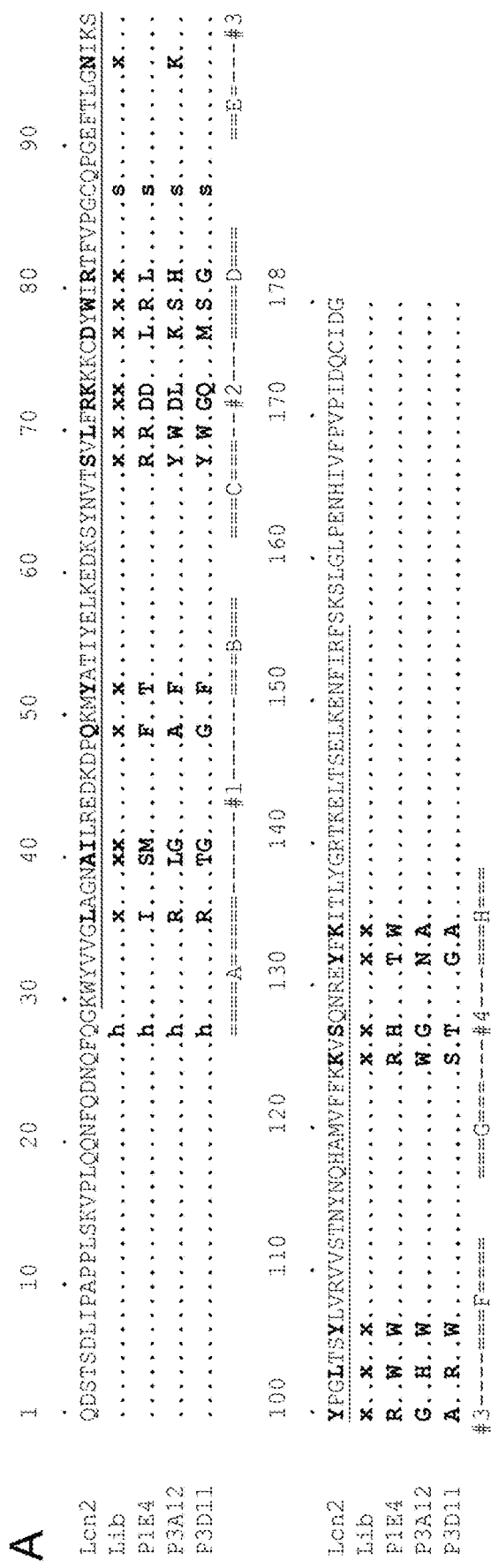

Figure 8 – continued
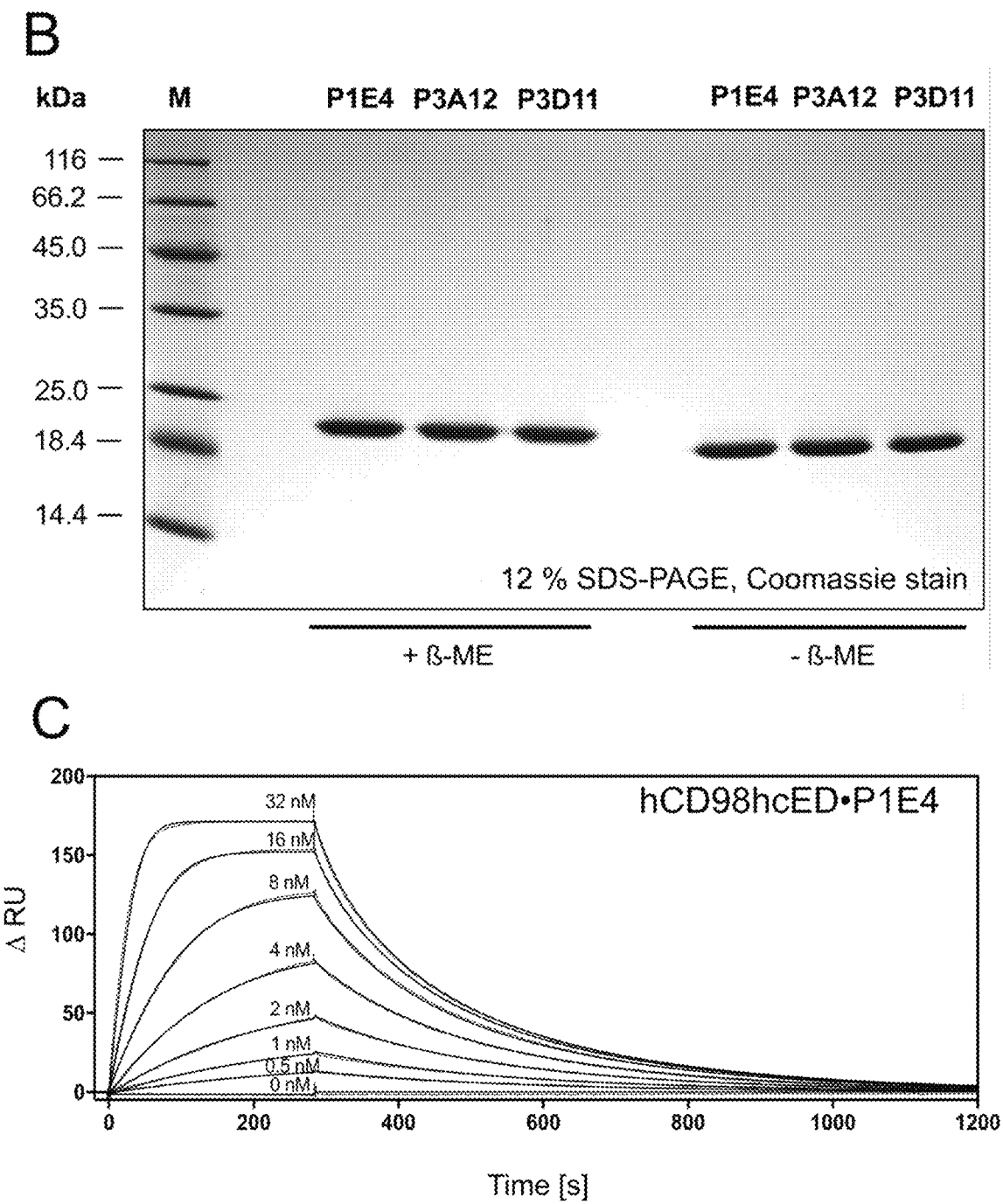

Figure 8 – continued
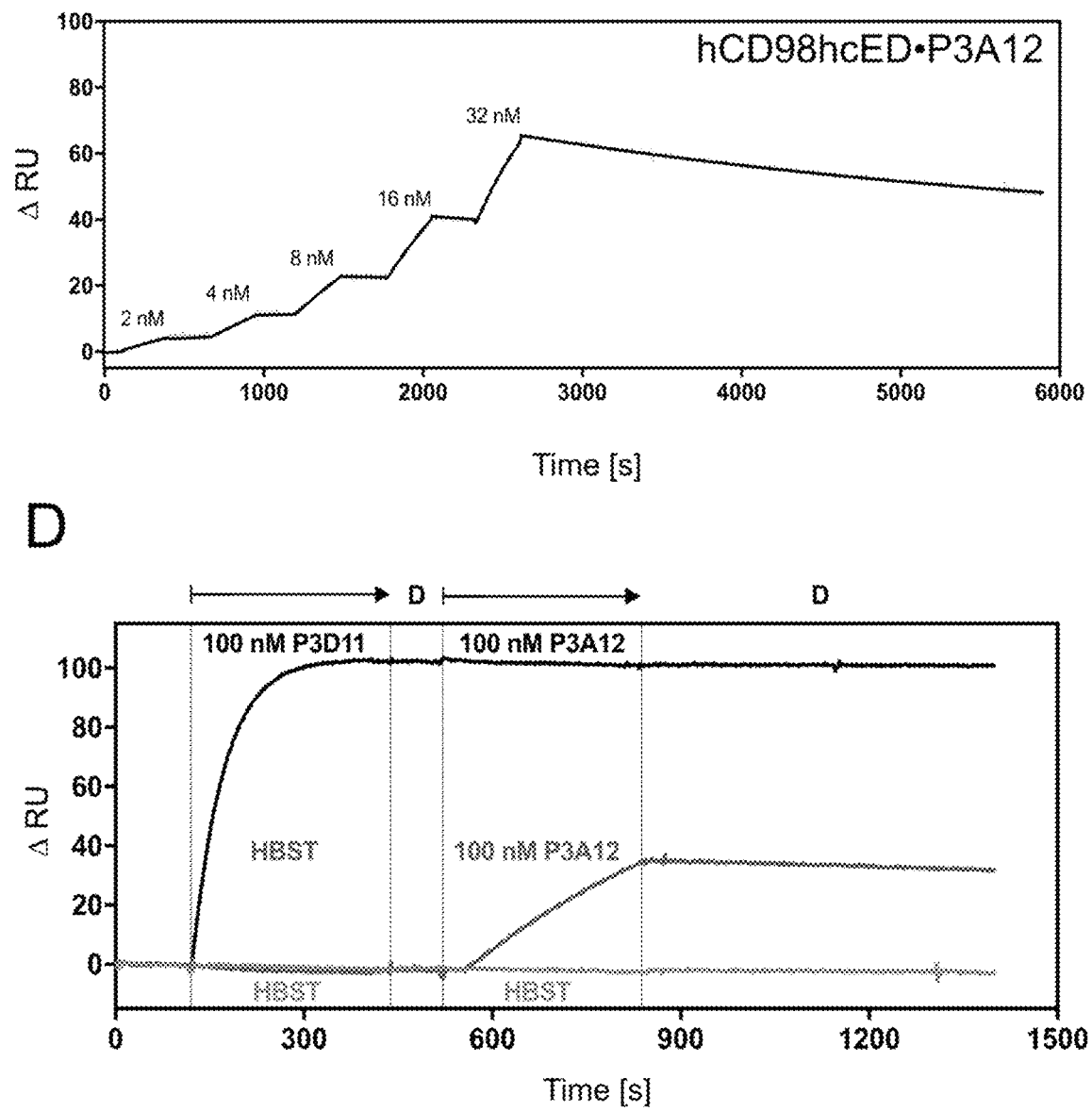

A

B

C

18 % (w/v) PEG3350
100 mM Na-malonate pH 4.75

D

Figure 11:
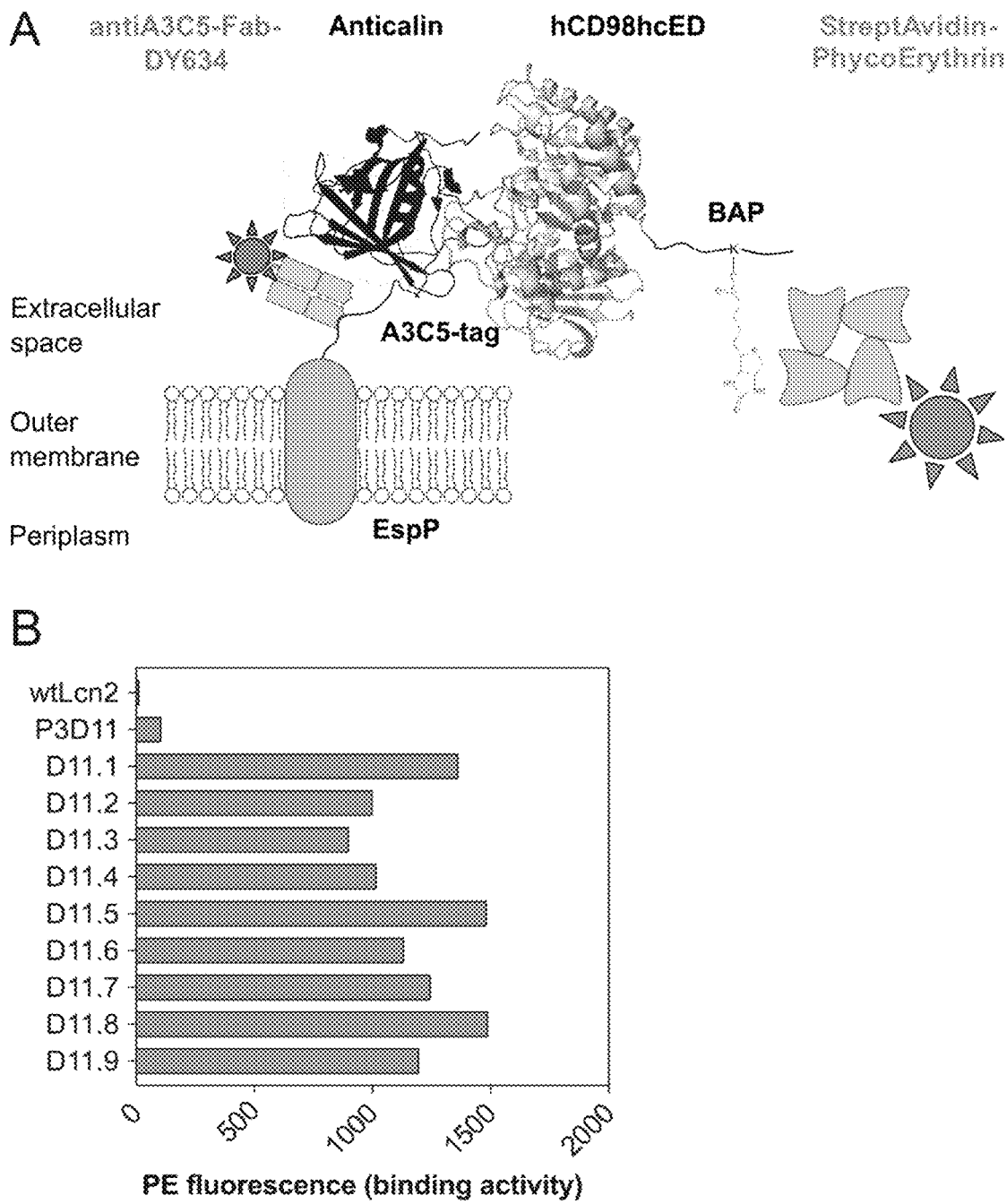

Figure 11 – continued
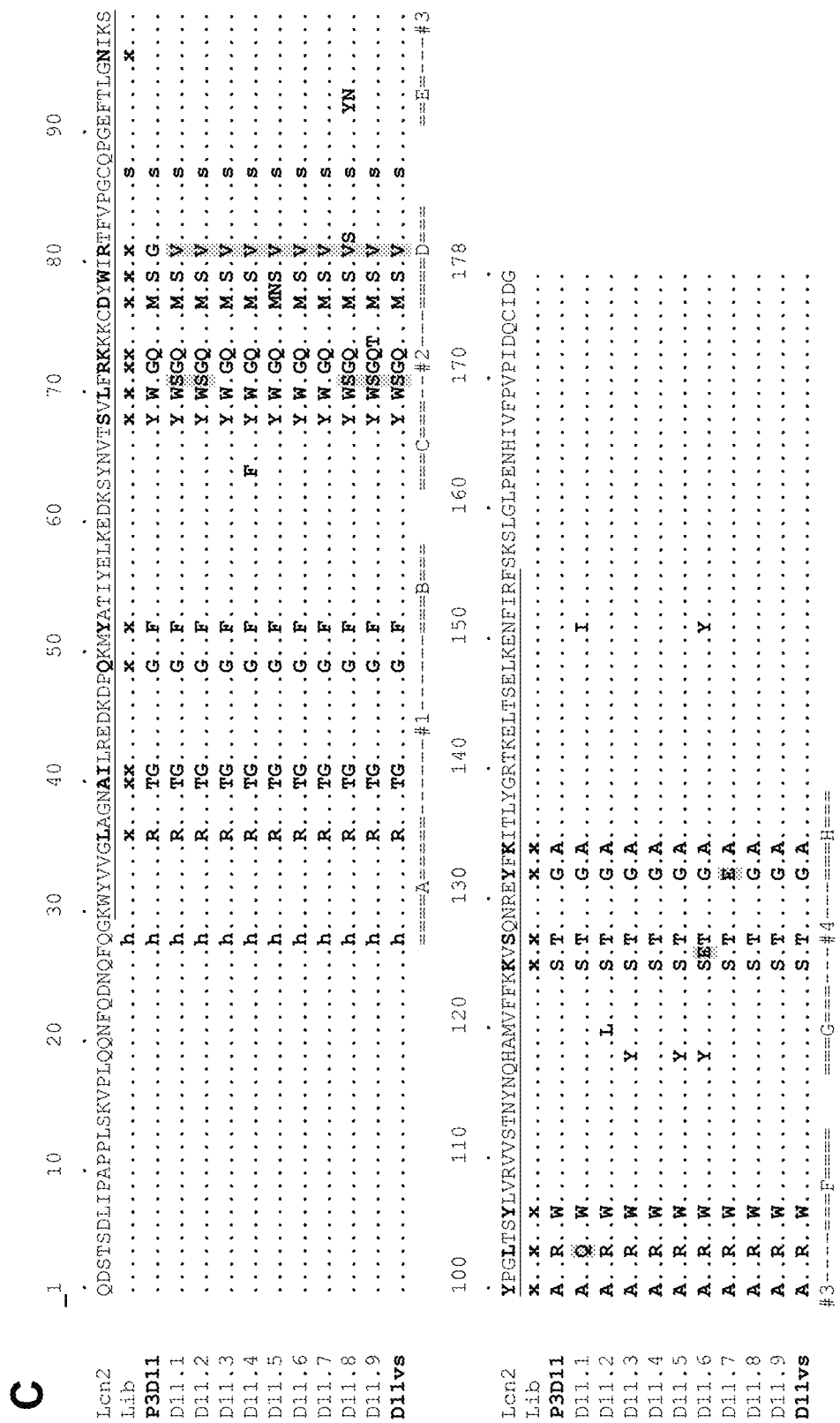

Figure 11 – continued
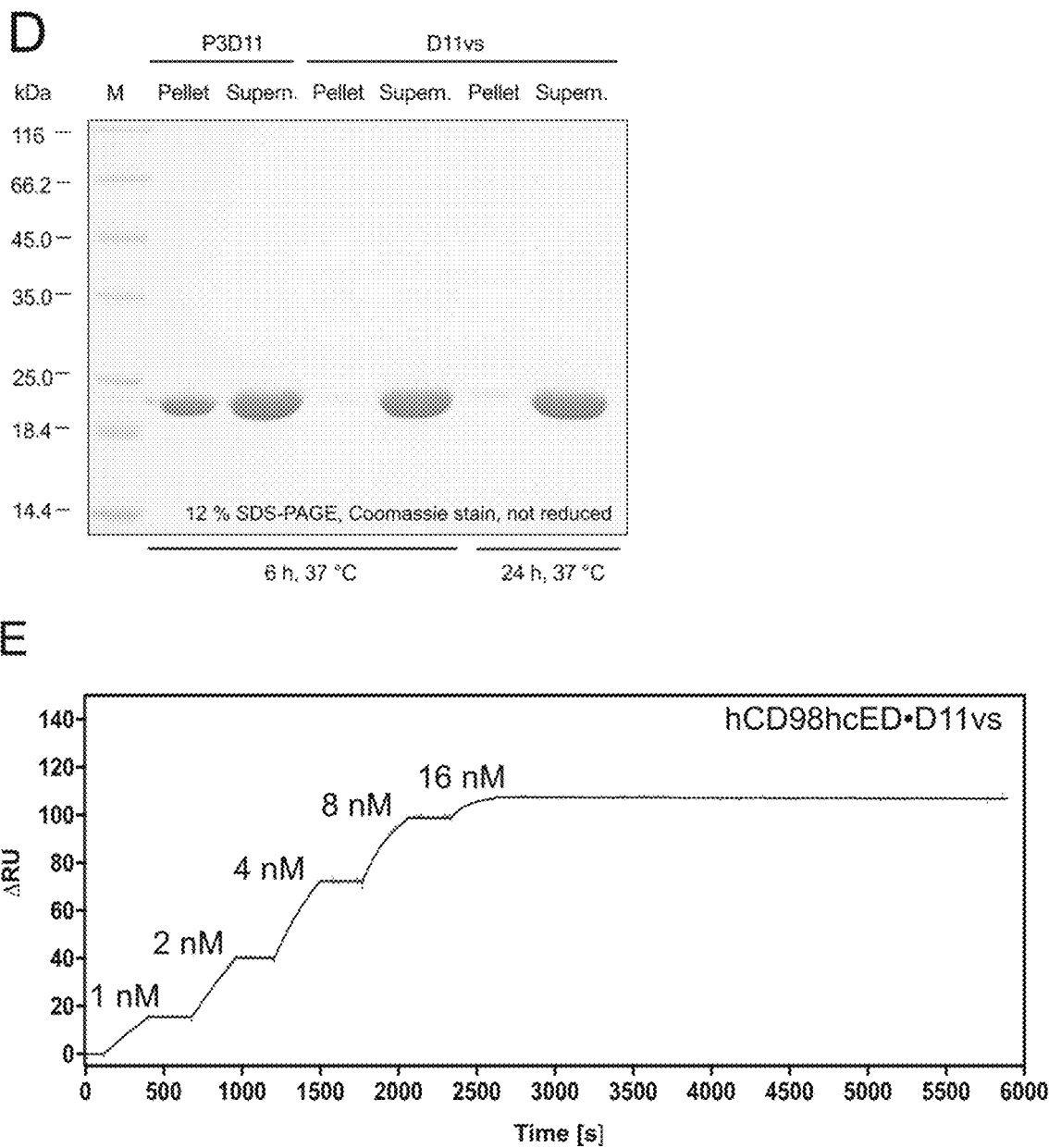

A

B

Figure 17:
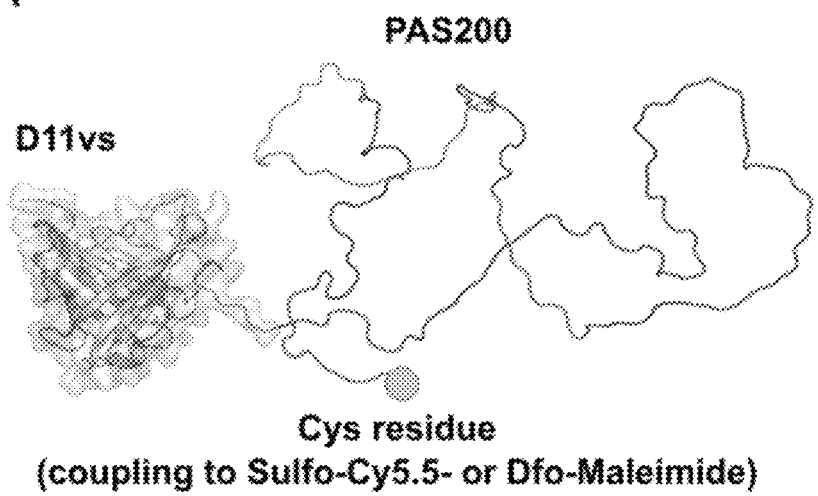
Figure 17:
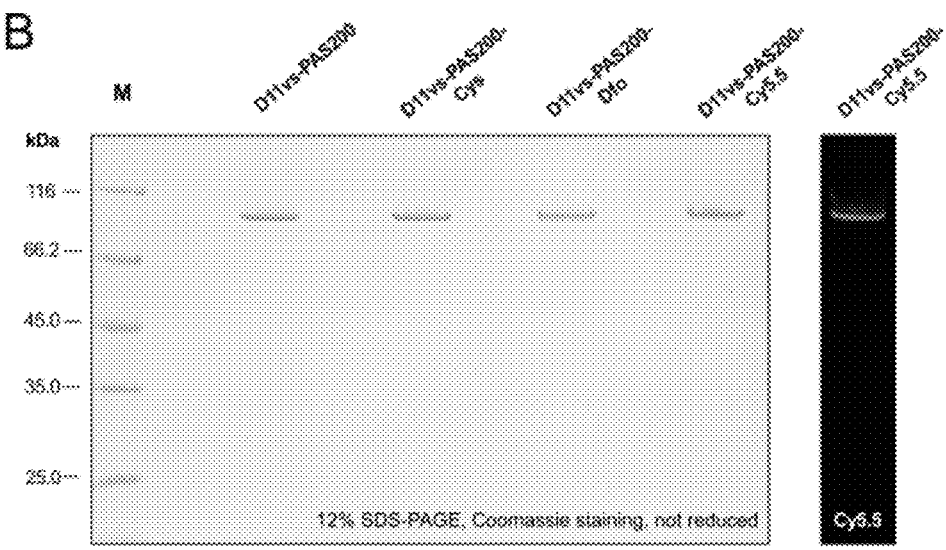

Figure 17 –
continued
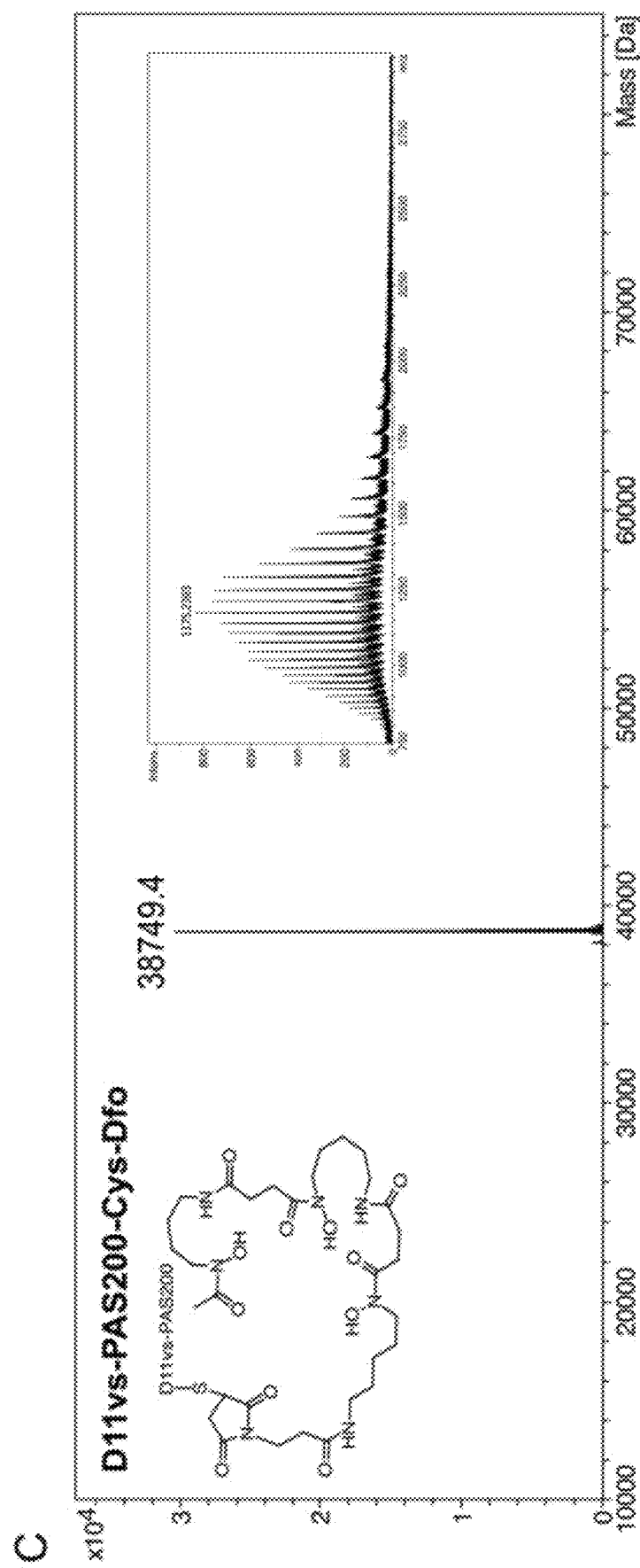

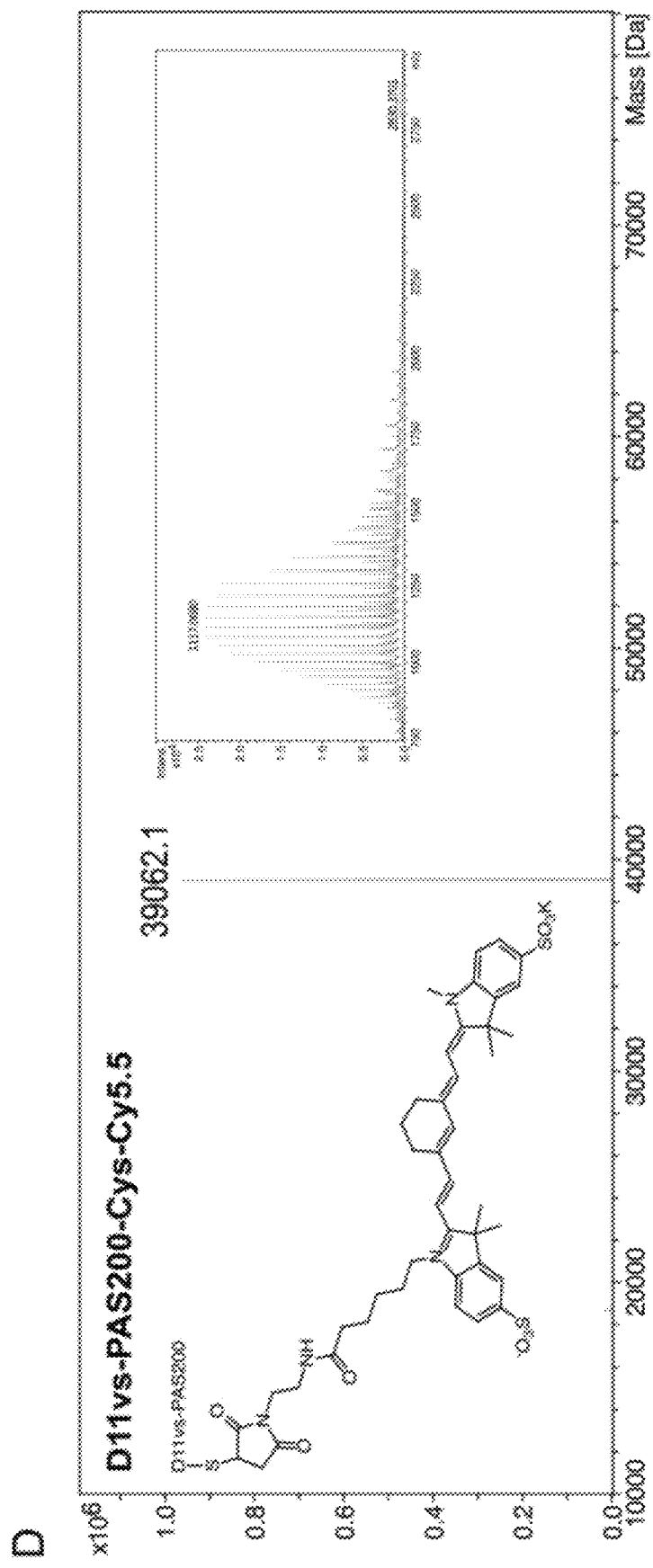
Figure 17 – continued

HIGH AFFINITY ANTICALINS DIRECTED AGAINST HUMAN CD98HC

RELATED PATENT APPLICATIONS

This patent application is a 35 U.S.C. 371 national phase patent application of PCT/EP2020/057469 filed on Mar. 18, 2020, entitled "HIGH AFFINITY ANTICALINS DIRECTED AGAINST HUMAN CD98hc", naming Arne SKERRA et al. as inventors, which claims priority to European Application No. 19165966.3 filed on Mar. 28, 2019, entitled "HIGH AFFINITY ANTICALINS DIRECTED AGAINST HUMAN CD98hc" naming Arne SKERRA et al. as inventors. The entire content of the foregoing patent applications is incorporated herein by reference, including all text, tables and drawings.

SEQUENCE LISTING

The instant application contains a Sequence Listing which has been submitted electronically in ASCII format and is hereby incorporated by reference in its entirety. Said ASCII copy is named Sequence Listing and is 42 kilobytes in size.

The present invention relates to a cluster of differentiation 98 heavy chain (CD98hc)-specific binding protein, wherein the CD98hc-specific binding protein is a lipocalin 2 (Lcn2)-derived binding protein and binds to CD98hc with a $K_D$ of 200 nM or lower.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Elevated amino acid supply and altered adhesive signaling both constitute crucial factors for cancer development and growth and also play a critical role for metastatic transformation of cells. Since the cluster of differentiation 98 heavy chain (CD98hc, also known as 4F2hc and FRP-1) is involved in both pathophysiological processes [1], its dysregulation contributes to cancer etiology.

In line with its important role in cellular metabolism and adhesive signaling, overexpression of CD98hc has been detected in solid and hematological human malignancies, including colorectal cancer [18], non-small cell lung cancer (NSCLC) [19, 20], triple-negative breast cancer [21, 22], metastatic prostate cancer [23] as well as lymphoma [24] and leukemia [17, 20]. Recent studies have indicated that clinically abundant expression of CD98hc is associated with poor prognosis [18, 19], treatment response [25, 26] or short overall survival in several cancers [22, 27, 28]. Furthermore, high CD98hc expression is linked to a progressive and metastatic phenotype in some human neoplasms; consequently, assessment of CD98hc expression allows cancer staging [29-32].

Likewise, elevated expression of the covalently associated CD98 light chains (lc's), in particular Lat-1 [33, 34], Lat-2 [35] and xCT [36, 37], have been observed in human cancers, with Lat-1 being the most abundant tumor marker. In fact, cancers from several tissues highly express both CD98hc and Lat-1, suggesting that this heterodimer possesses the highest oncogenic potential. Interestingly, in some cancers a positive cooperative overexpression of CD98hc and Lat-1, but not of Lat-1 alone, has emerged as an independent factor for poor prognosis in patients [22, 38, 39].

Therefore, the specific recognition and/or targeting of CD98hc by appropriately engineered proteins bear great potential for cancer theranostics. To date, the most advanced protein reagent is the humanized anti-hCD98hc monoclonal antibody (mAb) IGN523, which has shown robust preclinical anti-tumor activity in patient-derived lymphoma as well as non-small cell lung carcinoma (NSCLC) xenograft tumor models and, moreover, favorable safety profile in a phase I clinical study in humans [20, 40]. However, no molecular tools for non-invasive diagnostic imaging specific for the heavy chain of the heterodimeric CD98 membrane protein target have been described to date.

On the other hand, several reagents are available to target Lat-1: (i) small molecule inhibitors with proven preclinical antitumor activity in different cancer types [41]; (ii) radiolabeled amino acids such as $^{18}$F-fluoroethyl-L-tyrosine (FET) for PET imaging, effective and clinically used for the diagnosis of brain tumors in patients [42]; (iii) A $^{89}$Zr-labeled anti-Lat-1 mAb, which has shown high tumor uptake in a colorectal cancer xenograft model [43]. Nevertheless, detection and therapy of tumors using small molecule inhibitors or amino acid derivatives often lack specificity [43-45]. Also, mAbs suffer from drawbacks as imaging reagents, due to poor tissue penetration and unfavorable (slow) pharmacokinetics, which causes low imaging contrast [46].

Hence, there is a need for novel compounds being capable of specific recognition and/or targeting of CD98hc, in particular those being suitable for cancer theranostics. This need is addressed by the present invention.

Accordingly, the present invention relates in a first aspect to a cluster of differentiation 98 heavy chain (CD98hc)-specific binding protein, wherein the CD98hc-specific binding protein is a lipocalin 2 (Lcn2)-derived binding protein and binds to CD98hc with a $K_D$ of 200 nM or lower.

Cluster of differentiation 98 heavy chain (CD98hc; also known as 4F2hc and FRP-1) structurally is a type-II-transmembrane glycoprotein which is disulfide-linked to one of in total six known multi-pass CD98 light chains (CD98lc), all of which are permease-type amino acid transporters with different specificities [2], namely Lat-1 [3], Lat-2 [4], y+Lat-1 [5], y+Lat-2 [6], asc-1 [7] and xCT [8]. CD98 has two major biochemical functions (FIG. 1A): First, it acts as a molecular chaperon needed for membrane trafficking, stabilization and proper function of the CD98lc (light chain) [9], thus boosting the transport of several essential amino acids and contributing to cell survival and growth. Of note, beside serving as building blocks for protein synthesis, the transported amino acids and their metabolites can exert further important cellular functions, as known for L-leucine (mTOR1 pathway activation [10]) and L-cystine (regulation of redox homeostasis [11]), which are transported via the CD98hc/Lat-1 and CD98hc/xCT heterodimers, respectively [12]. Second, CD98hc participates in adhesive cellular signaling through interaction with the cytoplasmic part of β1-and β2-integrins, thereby influencing cell growth, survival, spreading and migration [13-15]. In fact, CD98hc contributes to intracellular α/β-integrin signaling [16] and is a key driver of integrin-mediated cell to cell interactions via cellular adhesion molecules like VCAM-1 [17].

CD98hc is preferably human CD98hc and more preferably the human CD98hc comprising or consisting of the amino acid of SEQ ID NO: 1. SEQ ID NO: 1 is encoded by the nucleic acid sequence of SEQ ID NO: 15.

Accordingly, the CD98hc-specific binding protein of the first aspect of the invention preferably specifically binds to human CD98hc.

The term "(poly)peptide" in accordance with the present invention describes a group of molecules which comprises the group of peptides, consisting of up to 30 amino acids, as well as the group of polypeptides, consisting of more than 30 amino acids. Also encompassed by the term "(poly)peptide" are proteins as well as fragments of proteins. (Poly)peptides may further form dimers, trimers and higher oligomers, i.e. consisting of more than one (poly)peptide molecule. (Poly) peptide molecules forming such dimers, trimers etc. may be identical or non-identical. The corresponding higher order structures are, consequently, termed homo- or heterodimers, homo- or heterotrimers etc. Homo- or heterodimers etc. also fall under the definition of the term "(poly)peptide". The terms "polypeptide" and "protein" are used interchangeably herein and also refer to naturally modified polypeptides wherein the modification is effected e.g. by glycosylation, acetylation, phosphorylation and the like. Such modifications are well known in the art.

The term "CD98hc-specific binding protein" relates to a molecule that specifically binds to (also referred to herein as "specifically interacts with") CD98hc but does not or essentially does not cross-react with a different protein of similar tertiary structure. Cross-reactivity of a panel of molecules under investigation may be tested, for example, by assessing binding of said panel of molecules to CD98hc as well as to a number of more or less (structurally and/or functionally) closely related proteins. Only those molecules that bind to CD98hc but do not or do not essentially bind to any of the other proteins are considered specific for CD98hc. Corresponding methods of measuring cross-reactivity/binding specificity are described e.g. in Harlow & Lane [1988] Antibodies: A Laboratory Manual, Cold Spring Harbor Laboratory Press; Harlow & Lane [1999] Using Antibodies: A Laboratory Manual, Cold Spring Harbor Laboratory Press.

The term "a molecule that essentially does not cross-react", as used herein, refers to a molecule that binds to CD98hc with at least 5-times higher affinity as compared to a different protein of similar structure, more preferably at least 10-times higher affinity, such as e.g. at least 50-times higher affinity, more preferably at least 100-times higher affinity, such as e.g. at least 250-times higher affinity. Even more preferably, it binds with at least 500-times higher affinity to CD98hc than to a different protein of similar structure and most preferably with at least 1.000-times higher affinity.

In accordance with the present invention, the CD98hc-specific binding protein is a lipocalin 2 (Lcn2)-derived binding protein. Lipocalin-derived binding proteins, also referred to as Anticalins, represent a class of non-immunoglobulin binding proteins based on the human lipocalin scaffold. Lipocalins comprise a diverse family of small (20 kDa) extracellular proteins that occur in many species ranging from bacteria to humans and serve for the transport or scavenging of physiological compounds. Despite mutually low sequence homology, the three-dimensional fold of lipocalins is highly conserved (Schiefner, A. & Skerra, A. [2015] Acc. Chem. Res. 48,976-985).

Their single chain molecular architecture is dominated by a compact eight-stranded anti-parallel β-barrel. At the open end of the barrel there are four loops connecting each pair of β-strands (see e.g. FIG. 2). The four structurally variable loops are referred to herein as "loop regions", whereas the remainder of the protein makes up the framework or "frame regions". Thus, similar to the structure of antibodies, the CD98hc-specific binding proteins of the present invention are essentially made of conserved framework regions that are generally not directly involved in the binding to the target molecule, i.e. CD98hc, as well as hypervariable, specificity-determining segments with amino acid residues being involved in the binding to the target molecule (here the loop regions, which might be seen as resembling the CDRs in antibodies).

Hence, lipocalin 2 and also lipocalin 2 (Lcn2)-derived binding proteins consist of frame regions and loop regions according to the following scheme: Frame 1-Loop 1-Frame 2-Loop 2-Frame 3-Loop 3-Frame 4-Loop 4-Frame 5

This scheme is further illustrated on the basis of the exemplified CD98hc-specific binding protein of SEQ ID NO: 2 (also designated D11vs herein):

QDSTSDLIPAPPLSKVPLQQNFQDNQFHGKWYVVGRAGNTGLREDKDPG

KMFATIYELKEDKSYNVTYVWSGQKKCMYSIVTFVPGSQPGEFTLGNIK

SAPGRTSWLVRVVSTNYNQHAMVFFKSVTQNREGFAITLYGRTKELTSE

LKENFIRFSKSLGLPENHIVFPVPIDQCIDG

The four loop regions comprise the underlined and double-underlined amino acid positions, further noting that each loop region comprises the loop as such (underlined) and flanking sequence stretches of the β-barrel on both sides (double-underlined). The five regions outside the loop regions are the five framework regions. This loop-framework scheme applies mutatis mutandis to the wild-type Lcn2 and the Lcn2 variants of SEQ ID NOs 3 to 14.

Lipocalin-2 (Lcn2), also known as oncogene 24p3 or neutrophil gelatinase-associated lipocalin (NGAL), is a protein that in humans is encoded by the LCN2 gene. Human LCN2 mRNA is, for example, represented by the NCBI Reference Sequence: NM_005564.5 (as available on Mar. 12, 2019) and human Lcn2 protein is, for example, represented by the UniProt ID P80188 (sequence version 2 as available on Nov. 1, 1995).

The CD98hc-specific binding protein of the present invention has been developed by structural modification of the Lcn2 molecule, i.e. it is a "lipocalin 2 (Lcn2)-derived binding protein". Preferably, the CD98hc-specific binding protein of the present invention is a binding protein derived from human lipocalin 2 (Lcn2).

In accordance with the present invention, the CD98hc-specific binding protein binds to CD98hc with a $K_D$ of 200 nM or lower.

In this respect it is of note that CD98hc can be glycosylated or non-glycosylated (also referred to herein as unglycosylated). As used herein, the glycosylated form of CD98hc has covalently attached at least one carbohydrate to the side chain to at least one amino acid of CD98hc.

Glycosylation is a complex enzymatic process leading to the post-translational modification of proteins. Indeed, glycosylation is thought to be the most complex post-translational modification, because of the large number of enzymatic steps involved. The glycosylation comprises or is preferably N-linked glycosylation. With respect to the human CD98hc of SEQ ID NO: 1 the glycosylation more preferably is N-linked glycosylation at Asn264, 280, 323 and 405 (according to UniProt entry P08195-2, Feb. 22, 2012) which is also referred to herein as fully glycosylated CD98hc or as CD98hcEDg (further noting that ED means the extracellular domain of the membrane receptor).

In the appended examples, the CD98hc-specific binding proteins of SEQ ID NOs 2 to 14 are illustrated. All of SEQ ID NOs 2 to 14 bind to non-glycosylated as well as glycosylated CD98hc with a $K_D$ of 200 nM or lower. The binding affinity of all of SEQ ID NOs 2 to 14 to non-glycosylated CD98hc is even higher with a $K_D$ of 5 nM or lower.

Hence, in accordance with the first aspect of the invention the CD98hc-specific binding protein preferably binds the glycosylated and the non-glycosylated form of CD98hc.

More preferably, the CD98hc-specific binding proteins of the present invention are capable of binding glycosylated CD98hc with a $K_D$ of 200 nM or lower and non-glycosylated CD98hc with a $K_D$ of 5 nM or lower.

Preferably, the CD98hc-specific binding protein binds with increasing preference to glycosylated CD98hc with a $K_D$ of 150 nM or lower, 100 nM or lower, 50 nM or lower, 5 nM or lower, 0.5 nM or lower, 250 pM or lower, 150 pM or lower, and 50 pM or lower. Also preferably, the CD98hc-specific binding protein binds with increasing preference to non-glycosylated CD98hc with a $K_D$ of 3 nM or lower, 1 nM or lower, 0.5 nM or lower, 250 pM or lower, 150 pM or lower, and 50 pM or lower.

The term "$K_D$" refers to the equilibrium dissociation constant (the reciprocal of the equilibrium binding constant) and is used herein according to the definitions provided in the art.

The $K_D$ value with which the CD98hc-specific binding protein binds to CD98hc can be determined by well known methods including, without being limiting, fluorescence titration, competition ELISA, calorimetric methods, such as isothermal titration calorimetry (ITC), flow cytometric titration analysis (FACS titration) and surface plasmon resonance spectroscopy (BIAcore). Such methods are well known in the art and have been described e.g. in De Jong, L. A. A. et al. [2005] J. Chromatogr. B 829(1-2):1-25; Heinrich, L. et al. [2010] J. Immunol. Methods 352(1-2): 13-22; Williams, M. A. & Daviter, T. (Eds.) [2013] Protein-Ligand Interactions, Methods and Applications, Springer, New York, N.Y. as well as in the examples herein below.

Preferably, ELISA or competition ELISA or surface plasmon resonance (BIAcore) is employed to ensure that the $K_D$ of the CD98hc-specific binding protein of the present invention is 200 nM or lower or 5 nM or lower. Even more preferably, the $K_D$ is determined by surface plasmon resonance (BIAcore).

As discussed herein above, mAbs against CD98hc are available in the art. However, such antibodies suffer from severe drawbacks as imaging agents, for example poor tissue penetration and long circulation times. These characteristics of mAbs cause significant background signal within the blood pool and non-target tissues and, consequently, provide poor contrast when employed for imaging purposes. In particular, no molecular tools including antibodies for the non-invasive diagnostic of CD98hc tissue expression in vivo have been described to date.

As also discussed, the CD98hc-specific binding proteins of the present invention are Anticalins. Anticalins constitute an emerging class of artificial binding proteins obtained by combinatorial design based on the compact and robust human lipocalin scaffold [47]. By contrast to antibodies, the CD98hc-specific binding proteins of the present invention advantageously show good tissue penetration as well as a tunable plasma half-life, thereby overcoming the drawbacks associated with antibodies. Due to their human origin, the CD98hc-specific binding proteins of the present invention have low immunogenic potential, and in several clinical trials Anticalins with different target specificities have demonstrated safety.

Moreover, these CD98hc-specific binding proteins show remarkable target specificity, with dissociation constants in the nanomolar and even picomolar range. Anticalins are particularly well suited for applications in cancer therapy and diagnostics due to their small size and good tissue penetration, tunable pharmacokinetics (i.e. via PEGylation or PASylation [46, 49]), the possibility for site-specific labeling (i.e. with PET/SPECT radioisotopes or optical imaging probes) or drug conjugation (i.e. toxins) and generally flexible formatting options [48].

It is shown in the appended examples that the CD98hc binding proteins of the invention strongly bind CD98hc on living human cells (FIG. 4). By labeling a CD98hc binding protein of the invention with the radioisotope $^{89}$Zr it is shown that the CD98hc binding protein of the invention specifically accumulates in CD98hc expressing tumors in vivo (FIG. 5). These data demonstrate that the CD98hc-specific binding proteins of the present invention show pharmacokinetics being more similar to that of small-molecules that are currently preferred in clinical practice, while at the same time exhibiting high specificity just like mAbs.

Thus, the present CD98hc-specific binding proteins provided herein are in several aspects superior to antibody-based CD98hc binders for biomedical applications, including the diagnosis of tumors, and in particular for the in vivo imaging of diseases. At the same time the CD98hc binding proteins of the invention bind to the target CD98hc at least as specifically and as strongly as an anti-CD98hc antibody.

In accordance with a preferred embodiment of the first aspect of the present invention, the CD98hc-specific binding protein specifically binds to an epitope of CD98hc comprising one or more amino acids from amino acid positions 128 to 137 of SEQ ID NO: 1 and/or one or more amino acids from amino acid positions 374 to 404 of SEQ ID NO: 1.

In this respect it is preferred that the epitope comprises two or more, preferably three or more, more preferably four or more and most preferably five or more amino acids from amino acid positions 128 to 137 of SEQ ID NO: 1 and/or two or more, preferably three or more, more preferably four or more and most preferably five or more amino acids from amino acid positions 374 to 404 of SEQ ID NO: 1.

As discussed above, in connection with the present invention the CD98hc-specific binding proteins of SEQ ID NOs 2 to 14 were developed. As will be further discussed herein below, the CD98hc-specific binding proteins of SEQ ID NOs 2 to 13 are structurally related with respect to the amino acid residues conferring CD98hc-specific binding. While the amino acid residues conferring CD98hc-specific binding of SEQ ID NO:00000 14 are not structurally related to these amino acid residues in SEQ ID NOs 2 to 13 it was surprisingly found that all of SEQ ID NOs 2 to 14 specifically bind to the same epitope area of human CD98hc (FIG. 8 and Table 6). Said epitope area comprises amino acids from amino acid positions 128 to 137 of SEQ ID NO: 1 and amino acids from amino acid positions 374 to 404 of SEQ ID NO: 1. The epitope can be found in the membrane-distal part of CD98hc.

As is exemplarily shown in the below examples for the Lnc2-variant of SEQ ID NO: 12 (P3D11), the contact interface between the Anticalins of the invention and CD98hc is among the largest known interfaces observed for Anticalins/protein complexes so far (Table 5). This kind of interface in turn explains why all of SEQ ID NOs 2 to 14 bind to CD98hc highly specifically and with a very strong binding affinity.

Hence, even though SEQ ID NOs 12 to 14 (further noting that SEQ ID NOs 2 to 11 are affinity maturated forms of SEQ ID NO: 12) were isolated by phage display selection from a prior art library of Lcn2 variants [50], it could not be expected beforehand that CD98hc-specific binding proteins can be obtained which bind so specifically and so strongly as the CD98hc-specific binding proteins of the invention. It is believed that this is due to the recognition of the discussed common epitope area of CD98hc.

In addition, it is of note that in the phage display selection the selection was done against the non-glycosylated form of CD98hc but that advantageously the CD98hc-specific binding proteins of the invention also bind the fully glycosylated form of CD98hc. Also this further advantage is due to the recognition of the discussed epitope area of CD98hc. To explain further, it is known that glycosylation effects the folding and stability of glycoproteins, so that it could not be expected beforehand that the epitope is an epitope which is maintained in the glycosylated form of CD98hc, so that it still can be specifically bound by the CD98hc-specific binding proteins of the invention.

In accordance with a further preferred embodiment of the first aspect of the present invention, the CD98hc-specific binding protein (a) comprises or consists of an amino acid sequence as represented in formula I:

QDSTSD($X_1$)($X_2$)PAPPLSKVPLQQNFQDNQF(Q/H)GKVVY($X_3$)VG ($X_4$)AG($X_5$)($X_6$)($X_7$)($X_8$)($X_9$)E($X_{10}$)($X_{11}$)($X_{12}$)($X_{13}$)

($X_{14}$)($X_{15}$)M($X_{16}$)ATIYELKEDKS(Y/F)NVT($X_{17}$)V($X_{18}$)

($X_{19}$)($X_{20}$)($X_{21}$)(K/T)KC($X_{22}$)(Y/N)($X_{23}$)($X_{24}$)($X_{25}$)

(T/S)($X_{26}$)VPG(C/S)QPGE(F/Y)(T/N)($X_{27}$)G(N/K)I($X_{28}$)

S(Y/R/G/A)P($X_{29}$)($X_{30}$)($X_{31}$)S($X_{32}$)L($X_{33}$)RVVSTNYNQ (H/Y)A(M/L)VF($X_{34}$)K($X_{35}$)(V/E)($X_{36}$)($X_{37}$)N($X_{38}$)E ($X_{39}$)($X_{40}$)($X_{41}$)I($X_{42}$)L($X_{43}$)GRTKELTSELKE(N/I/Y)FIR

FSKSLGLPE($X_{44}$)($X_{45}$)IVFPVPIDQCIDG, wherein
($X_1$) is L;
($X_2$) is I;
($X_3$) is V;
($X_4$) is R;
($X_5$) is N;
($X_6$) is L or T, preferably T;
($X_7$) is G;
($X_8$) is L;
($X_9$) is R;
($X_{10}$) is D;
($X_{11}$) is K;
($X_{12}$) is D;
($X_{13}$) is P;
($X_{14}$) is A or G, preferably G;
($X_{15}$) is K;
($X_{16}$) is F;
($X_{17}$) is Y;
($X_{18}$) is W;
($X_{19}$) is F or S, preferably S;
($X_{20}$) is D or G, preferably G;
($X_{21}$) is L or Q, preferably Q;
($X_{22}$) is K or M, preferably M;
($X_{23}$) is S;
($X_{24}$) is I;
($X_{25}$) is H, G or V, preferably V;
($X_{26}$) is F;
($X_{27}$) is L;
($X_{28}$) is K;
($X_{29}$) is G;
($X_{30}$) is H, R or Q, preferably R;
($X_{31}$) is T;
($X_{32}$) is W;
($X_{33}$) is V;
($X_{34}$) is F;
($X_{35}$) is W or S, preferably S;
($X_{36}$) is G or T, preferably T;
($X_{37}$) is Q;
($X_{38}$) is R;
($X_{39}$) is N, G or E, preferably G;
($X_{40}$) is F;
($X_{41}$) is A;
($X_{42}$) is T;
($X_{43}$) is Y;
($X_{44}$) is N; and
($X_{45}$) is H;

(b) an amino acid sequence which is at least 80% identical to the amino acid sequence of (a), provided that amino acid positions ($X_1$) to ($X_{45}$) are maintained as defined in item (a); (c) an amino acid sequence which is at least 80% identical to the amino acid sequence of (a), provided that amino acid positions ($X_1$) to ($X_{45}$) are maintained as defined in item (a) or are changed by one or more conservative amino acid substitutions; or (d) an amino acid sequence which is at least 80% identical to the amino acid sequence of (a), provided that no more than ten amino acid positions of ($X_1$) to ($X_{45}$) as defined in item (a) are changed by amino acid substitutions, wherein the amino acid substitutions are preferably conservative amino acid substitutions.

For the avoidance of doubt in all the above preferred embodiments as well as later discussed preferred embodiments, the binding specificity and affinity described for the first embodiment are of course retained.

The term "comprising", as used in accordance with the present invention, denotes that further sequences/components can be included in addition to the specifically recited sequences and/or components. However, this term also encompasses that the claimed subject-matter consists of exactly the recited sequences and/or components.

In those embodiments where the CD98hc-specific binding protein includes more than the recited amino acid sequence, additional amino acids extend over the specific sequence of formula (I) either at the N-terminal end or the C-terminal end or both. Additional sequences may include, for example, sequences introduced for purification or detection, as discussed in detail herein below.

It is a prerequisite that the binding affinity of the CD98hc-specific binding protein to CD98hc in the presence of these additional amino acids is retained or essentially retained. In accordance with the present invention, the binding affinity to CD98hc is considered to be essentially retained if the difference or the ratio between the $K_D$ of the CD98hc-specific binding protein comprising such additional amino acids and the $K_D$ of the same CD98hc-specific binding protein without such additional amino acids is within two orders of magnitude (i.e. within a factor of 100), more preferably within one order of magnitude (i.e. within a factor of 10), even more preferably within a factor of 3, and yet more preferably within a factor of 2. Most preferred is that the binding affinity is fully retained, i.e. the $K_D$ of the CD98hc-specific binding protein comprising such additional amino acids is equal or lower than the $K_D$ of the same CD98hc-specific binding protein without such additional amino acids. Generally, a lower $K_D$ value corresponds to a higher or better affinity as is well known in the art. Therefore, also in accordance with the invention are CD98hc-specific binding proteins having an increased binding affinity compared to the CD98hc-specific binding protein without such additional amino acids.

Methods of assessing the binding affinity have been described herein above in connection with the discussion of the term "$K_0$" and include, without being limiting, fluorescence titration, ELISA or competition ELISA, calorimetric methods, such as isothermal titration calorimetry (ITC), flow cytometric titration analysis (FACS titration) and surface plasmon resonance spectroscopy (BIAcore).

In accordance with the present invention, the term "% sequence identity" describes the number of matches ("hits") of identical amino acids of two or more aligned amino acid sequences as compared to the number of amino acid residues making up the overall length of the amino acid sequences (or the overall compared part thereof). Percent identity is determined by dividing the number of identical residues by the total number of residues and multiplying the product by 100. In other terms, using an alignment, the percentage of amino acid residues that are the same (e.g., 80% identity) may be determined for two or more sequences or sub-sequences when these (sub)sequences are compared and aligned for maximum correspondence over a window of comparison, or over a designated region as measured using a sequence comparison algorithm as known in the art, or when manually aligned and visually inspected.

Those having skills in the art know how to determine percent sequence identity between/among sequences using, for example, algorithms such as those based on the NCBI BLAST algorithm (Altschul, S. F. et al. [1997] Nucleic Acids Res. 25:3389-3402), CLUSTALW computer program (Tompson, J. D. et al. [1994] Nucleic Acids Res. 22:4673-4680) or FASTA (Pearson, W. R. & Lipman, D. J. [1988] Proc. Natl. Acad. Sci. U.S.A. 85:2444-2448). The NCBI BLAST algorithm is preferably employed in accordance with this invention. For amino acid sequences, the BLASTP program uses as default a word length (W) of 3, and an expectation (E) of 10. The BLOSUM62 scoring matrix (Henikoff, S. & Henikoff, J. G. [1992] Proc. Natl. Acad. Sci. U.S.A. 89:10915-10919) uses alignments (B) of 50, expectation (E) of 10, M=5, N=4, and a comparison of both strands. Accordingly, all the proteins or (poly)peptides having a sequence identity of at least 80% as determined with the NCBI BLAST program fall under the scope of the invention.

The at least 80% identity as referred to herein is with increasing preference at least 85%, at least 90%, at least 95%, at least 97%, at least 98% and at least 99% identity.

The term "provided that amino acid positions ($X_1$) to ($X_{45}$) are maintained as defined in item (a)" and related terms herein mean that no amino acid changes can be made with respect to these amino acid positions. Amino acid changes, while maintaining the required at least 80% identity, may only be introduced outside these amino acid positions. With respect to the identity of at least 80% it is preferred with increasing preference that no more than 10 amino acid positions, no more than 9 amino acid positions, no more than 8 amino acid positions, no more than 7 amino acid positions, no more than 6 amino acid positions, no more than 5 amino acid positions, no more than 4 amino acid positions, no more than 3 amino acid positions, no more than 2 amino acid positions, and 1 amino acid position is/are changed.

Amino acid changes, for each change independently, can be additions, deletions or substitutions and are preferably substitutions. An "addition" is the introduction of an additional amino acid into an amino acid sequence, for example, the sequence of formula I. Accordingly, a "deletion" is the removal of an amino acid from an amino acid sequence, for example, the sequence of formula I. The term "substitution" as used herein refers to the replacement of a particular amino acid with another amino acid. Thus, the total number of amino acids remains the same. In those cases where more than one amino acid is to be substituted, each amino acid is independently replaced with another amino acid, i.e. for each amino acid that is removed a different amino acid is introduced at the same position. The deletion of one or more amino acids at (a) certain position(s) and the introduction of one or more amino acids at (a) different position(s) is explicitly not encompassed by the term "substitution".

Substitutions can be conservative amino acid substitutions or non-conservative amino acid substitutions.

The term "conservative amino acid substitution" refers to the replacement of an amino acid with a different amino acid having similar structural and/or chemical properties. Such similarities include e.g. a similarity in polarity, charge, solubility, hydrophobicity, hydrophilicity, and/or the amphipathic nature of the residues involved. For example, nonpolar (hydrophobic) amino acids include alanine, valine, leucine, isoleucine, proline, phenylalanine, tyrosine, tryptophan, and methionine; polar neutral amino acids include glycine, serine, threonine, cysteine, asparagine, and glutamine; positively charged (basic) amino acids include arginine, lysine, and histidine; and negatively charged (acidic) amino acids include aspartic acid and glutamic acid.

Non-conservative amino acid substitutions can be introduced in order to introduce new reactive groups, for example, for the conjugation to other compounds, such as polyethylene glycol (PEG), hydroxyethyl starch (HES), biotin, peptides or proteins, toxins, dyes, fluorescent groups, metal-chelating groups or for the formation of non-naturally occurring intermolecular disulphide linkages. To this end, for example, cysteine may be introduced into the amino acid sequence, preferably at a position that corresponds to the position 14, 21, 60, 84, 87, 88, 114, 116, 117, 141, 143, 145, 146 or 158 of the wild-type (wt) Lcn2 sequence, which correspond to positions 14, 21, 60, 84, 141, 143, 145, 146 or 158 of the amino acid sequences of SEQ ID NOs 2 to 14. The thiol moiety thus generated can then be used for the conjugation to other compounds, for example, in order to increase the serum half-life of the respective CD98hc-specific binding protein or to functionalize it for diagnostic and/or therapeutic use. Accordingly, it is preferred, in accordance with the present invention, that in those cases where the substitution is a non-conservative amino acid substitution, it is a substitution that introduces a cysteine at one or more of the above described positions.

The "no more than 10 amino acid positions" of item (d) of the embodiments as referred to herein are with increasing preference no more than 9 amino acid positions, no more than 8 amino acid positions, no more than 7 amino acid positions, no more than 6 amino acid positions, no more than 5 amino acid positions, no more than 4 amino acid positions, no more than 3 amino acid positions, no more than 2 amino acid positions, and 1 amino acid position.

The amino acid sequence as represented in formula I is also reflected in SEQ ID NO: 16. Formula I is based on the CD98hc-specific binding proteins of SEQ ID NOs 2 to 13. As mentioned, the CD98hc-specific binding proteins of SEQ ID NOs 2 to 13 are structurally related with respect to the amino acid residues conferring CD98hc-specific binding activity.

In greater detail, the CD98hc-specific binding proteins of SEQ ID NOs 12 and 13 were isolated from a library of Lnc2-variants. In this library a total of 20 amino acids in the four loops of Lnc2 were randomized, noting that the 20 amino acids were initially selected on the basis of the contact area of Lnc2-variants binding to proteins other than CD98hc. Hence, while it was by no means obvious that the library comprises any binders to CD98hc, let alone the highly specific CD98hc binding proteins of the invention binding to CD98hc in the nanomolar or sub-nanomolar range, it is remarkable that 8 of these 20 amino acids are the same between SEQ ID NOs 12 (P3D11) and 13 (P3A12) and that these 8 amino acids are not shared by SEQ ID NO: 14 (P1E4), which has a lower binding affinity to CD98hc than SEQ ID NOs 12 and 13. SEQ ID NOs 2 to 12 are affinity matured versions of SEQ ID NO: 12, wherein even 9 of the discussed 20 amino acids are the same as in SEQ ID NO: 13.

Moreover, an analysis of the contact surface of SEQ ID NO: 12 with CD98hc revealed that 2 of the 20 amino acids do not contribute to the binding of CD98hc. As expected, several further amino acids within the loops are also part of the contact surface. On the other hand, it was surprisingly found that 2 amino acid positions each located within the most N-terminal and the most C-terminal framework region also contribute to the binding of CD98hc. Since the contact area of Anticalins is generally found within the loop regions, the contribution of further amino acids clearly outside of these loop regions was unexpected and may explain the superior binding specificity of SEQ ID NO: 12 and the related SEQ ID NOs 2 to 11 and 13 towards CD98hc. Moreover, in view of the structural relatedness of SEQ ID NOs 2 to 13 it can be expected that the epitope-contact area in SEQ NOs 2 to 11 and 13 is the same or essentially the same as in SEQ ID NO: 12.

Figure 16:
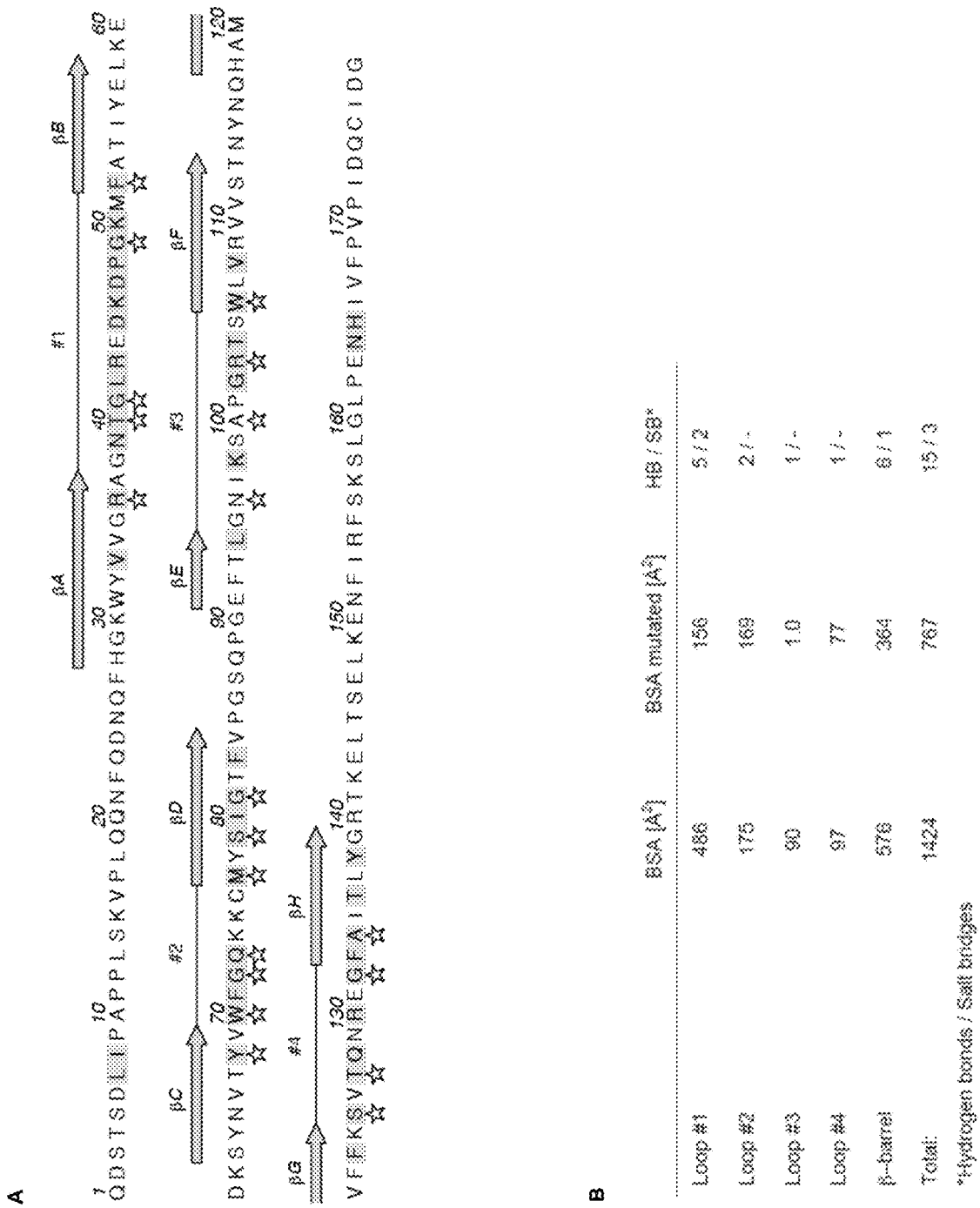

With one exception, the 45 amino acids positions marked as $X_1$ to $X_{45}$ in formula I are the amino acids which are responsible for the binding to CD98hc, similarly to CDR sequences of an antibody (FIG. 16). The one exception is amino acid position 71 ($X_{19}$ in formula I), wherein the preferred amino acid serine confers the additional advantage of a higher temperature stability. It is therefore generally preferred for all binding proteins of the invention that amino acid position 71 is serine. The amino acids listed as $X_1$ to $X_{45}$ are those that can be found at the corresponding positions in SEQ ID NOs 2 to 13. The preferred amino acids listed for as $X_1$ to $X_{45}$ are those that can be found at the corresponding positions in SEQ ID NO: 2 (D11vs). SEQ ID NO: 2 is the affinity matured version of SEQ ID NO: 12 with the highest binding affinity to CD98hc and the mentioned higher temperature stability. SEQ ID NO: 2 even has a binding affinity to CD98hc even in the lower picomolar range ($K_D$=50 pM for unglycosylated CD98hc).

In formula I also certain amino acids outside $X_1$ to $X_{45}$ may be selected from two, three or four different amino acids (e.g. Q/H or N/I/Y or Y/R/G/A). As discussed, SEQ ID NOs 2 to 11 are affinity matured versions of SEQ ID NO: 12. In the affinity maturation process additional amino acid mutations were introduced into SEQ ID NO: 12 and, after subsequent selection, the affinity matured versions SEQ ID NOs 2 to 11 were obtained. In SEQ ID NOs 2 to 11 also certain substitutions outside $X_1$ to $X_{45}$ were introduced. These amino acid changes neither specifically contribute to the binding to CD98hc nor do they diminish the binding to CD98hc. Accordingly, at these position any one of the amino acids as indicated in formula I can be present without substantially affecting the binding affinity to CD98hc. It is, though, preferred that at these amino acid positions the amino acids in the corresponding positions of SEQ ID NO: 2 are present.

In accordance with a further preferred embodiment of the first aspect of the present invention, the CD98hc-specific binding protein (a) comprises or consists of the amino acid sequence of (SEQ ID NO: 14)
QDSTSDLIPAPPLSKVPLQQNFQDNQF<u>HGKWYVVGIAGNSMLREDKDPF</u>

KMTATIYELKEDK<u>SYNVTRVRFDDKKCLYRILTF</u>VPGSQPGEFTLGNIK

SRPGWTSWLVRVVSTNYNQ<u>HAMVFFKRVHQNRETFWITLYG</u>RTKELTSE

LKENFIRFSKSLGLPENHIVFPVPIDQCIDG (b) an amino acid sequence which is at least 80% identical to the amino acid sequence of (a), provided that the underlined amino acids are maintained as defined in item (a); (c) an amino acid sequence which is at least 80% identical to the amino acid sequence of (a), provided that the underlined amino acids are maintained as defined in item (a) or are changed by one or more conservative amino acid substitutions; or (d) an amino acid sequence which is at least 80% identical to the amino acid sequence of (a), provided that no more than ten of the underlined amino acids as defined in item (a) are changed by amino acid substitutions, wherein the amino acid substitutions are preferably conservative amino acid substitutions.

As discussed above, although all of SEQ ID NOs 2 to 14 bind to the same epitope area, the CD98hc binding surface of the Lnc2-variant of SEQ ID NO: 14 is not structurally related to those of in SEQ ID NOs 2 to 13. For this reason, the above preferred embodiment is based on the structure of SEQ ID NO: 14. While the exact epitope-contact area of SEQ ID NO: 14 with CD98hc is yet to be determined it can be assumed that in particular the amino acids in the four loop regions (underlined) determine the specific binding of SEQ ID NO: 14 to CD98hc. For this reason, in accordance with this embodiment the amino acids in the loop regions of SEQ ID NO: 14 are either maintained (item (b)) or only changed within narrow limitations (items (c) and (d)).

In accordance with a further preferred embodiment of the first aspect of the present invention, the CD98hc-specific binding protein comprises or consists of (a) the amino acid sequence of any one of SEQ ID NOs 2 to 14; or (b) an amino acid sequence which is at least 80% identical to the amino acid sequence of (a).

The amino acid sequence of any one of SEQ ID NOs 2 to 14 is with increasing preference any one of SEQ ID NOs 2 to 13, any one of SEQ ID NOs 2 to 12, any one of SEQ ID NOs 2 to 11 and most preferably of SEQ ID NO: 2. As discussed, SEQ ID NOs 2 to 13 have a higher binding affinity than SEQ ID NOs 2 to 14 whereas SEQ ID NOs 2 to 12 have a higher binding affinity than SEQ ID NOs 2 to 13. SEQ ID NOs 2 to 11 are affinity matured versions of SEQ ID NO: 12 and among them SEQ ID NO: 2 is the best performer.

Among SEQ ID NOs 2 to 11, SEQ ID NOs 2, 3, 4, 10 and 11 are particularly preferred since at amino acid position 71 of these Lnc2-variants the serine residue is present which was found to provide the additional advantage of a higher temperature stability.

The present invention relates in a second aspect to a nucleic acid molecule encoding the CD98hc-specific binding protein of the first aspect.

The definitions and preferred embodiments of the first aspect of the invention apply mutatis mutandis to the second aspect of the invention. The Lcn2-variants of SEQ ID NOs 2 to 14 are encoded by SEQ ID NO: 17 to 29, respectively.

The term "nucleic acid molecule", also referred to as nucleic acid sequence or polynucleotide herein, as used herein includes DNA, such as cDNA or genomic DNA, and RNA. It is understood that the term "RNA" as used herein comprises all forms of RNA including mRNA. Both, single-strand as well as double-strand nucleic acid molecules are encompassed by this term. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA), peptide nucleic acid (PNA) and locked nucleic acid (LNA) (see Braasch, D. A. & Corey, D. R. [2001] Chem. Biol. 8:1-7). PNA is a synthetic DNA-mimic with an amide backbone in place of the sugar-phosphate backbone of DNA or RNA. As a consequence, certain components of DNA, such as phosphorus, phosphorus oxides, or deoxyribose derivatives, are not present in PNAs. LNA is an RNA derivative in which the ribose ring is constrained by a methylene linkage between the 2'-oxygen and the 4'-carbon. They may contain additional non-natural or derivatised nucleotide bases, as will be readily appreciated by those skilled in the art.

The nucleic acid molecules of the invention can e.g. be synthesized by standard chemical synthesis methods or isolated from natural sources or produced semi-synthetically, i.e. by combining chemical synthesis and isolation from natural sources. Ligation of the coding sequences to transcriptional regulatory elements and/or to other amino acid encoding sequences can be carried out using established methods, such as restriction digest, ligation and molecular cloning.

The present invention relates in a third aspect to a vector comprising the nucleic acid molecule of the second aspect.

The definitions and preferred embodiments of the above aspects of the invention apply mutatis mutandis to the third aspect of the invention.

Usually, the vector is a plasmid, cosmid, virus, bacteriophage or another vector used conventionally e.g. in genetic engineering. Preferably, the vector is a plasmid, more preferably a plasmid based on the generic E. coli expression vector pASK75, such as e.g. the vector pNGAL98. Such vectors that were specifically developed for Anticalin expression but also Anticalin production by e.g. periplasmic secretion in E. coli have been described in the art, e.g. in (Gebauer, M. & Skerra, A. [2012] Meth. Enzymol. 503:157-188).

Alternative vectors including, without being limiting, plasmid vectors, such as pQE-12, the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for Pichia pastoris comprise e.g. the plasmids pAO815, pPIC9K and pPIC3.5K (all Invitrogen). Another vector suitable for expressing proteins in Xenopus embryos, zebrafish embryos as well as a wide variety of mammalian and avian cells is the multipurpose expression vector pCS2+.

Generally, vectors can contain one or more origins of replication (on) and inheritance systems for cloning or expression, one or more markers for selection in the host, e.g., antibiotic resistance, and one or more expression cassettes. In addition, the coding sequences comprised in the vector can be ligated to transcriptional regulatory elements and/or to other amino acid encoding sequences using established methods. Such regulatory sequences are well known to those skilled in the art and include, without being limiting, regulatory sequences ensuring the initiation of transcription, internal ribosomal entry sites (IRES) (Owens, G. C. et al. [2001] Proc. Natl. Acad. Sci. U.S.A. 98:1471-1476) and optionally regulatory elements ensuring termination of transcription and stabilization of the transcript. Non-limiting examples for such regulatory elements ensuring the initiation of transcription comprise promoters, a translation initiation codon, enhancers, insulators and/or regulatory elements ensuring transcription termination. Further examples include Kozak sequences and intervening sequences flanked by donor and acceptor sites for RNA splicing, nucleotide sequences encoding secretion signals or, depending on the expression system used, signal sequences capable of directing the expressed protein to a cellular compartment or to the culture medium. The vectors may also contain an additional expressible polynucleotide coding for one or more chaperones to facilitate correct protein folding. Suitable bacterial expression hosts comprise e. g. strains derived from JM83, W3110, KS272, TG1, BL21 (such as BL21(DE3), BL21 (DE3)PlysS, BL21(DE3)RIL, BL21(DE3)PRARE) or Rosetta. For vector modification, PCR amplification and ligation techniques, see Sambrook & Russel [2001], Molecular cloning a laboratory manual (Cold Spring Harbor Laboratory, NY).

Vector elements that have been optimized for the expression of Anticalins have been described in the art, e.g. in (Gebauer, M. & Skerra, A. [2012] Meth. Enzymol. 503:157-188) and include the tetracycline promoter/operator (tet$^{o/o}$), which is chemically inducible with anhydrotetracycline, an N-terminal OmpA signal for periplasmic secretion in E. coli, an affinity tag, such as e.g. Strep-tag II or the A3C5 tag, the rho-independent lpp terminator as well as an ampicillin-resistance gene (β-lactamase), a truncated ColEI origin of replication, and, optionally, the intergenic region of the filamentous phage f1 for the biosynthesis of phagemid particles upon co-infection of E. coli with a helper phage.

Additional examples of suitable origins of replication include, for example, the full length ColE1, the SV40 viral and the M13 origins of replication, while additional examples of suitable promoters include, without being limiting, the cytomegalovirus (CMV) promoter, SV40-promoter, RSV-promoter (Rous sarcoma virus), the lacZ promoter, chicken β-actin promoter, CAG-promoter (a combination of chicken β-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the T7 or T5 promoter, the lacUV5 or ara promoter, the *Autographa californica* multiple nuclear polyhedrosis virus (AcMNPV) polyhedral promoter or a globin intron in mammalian and other animal cells. One example of an enhancer is e.g. the SV40-enhancer. Non-limiting additional examples for regulatory elements ensuring transcription termination include the SV40-poly-A site, the tk-poly-A site or the AcMNPV polyhedral polyadenylation signals. Further non-limiting examples of selectable markers include dhfr, gpt, neomycin, hygromycin, blasticidin or geneticin. Preferably, the vector of the present invention is an expression vector. An expression vector according to this invention is capable of directing the replication and the expression of the nucleic acid molecule of the invention and, accordingly, of the CD98hc-specific binding proteins of the present invention encoded thereby.

The nucleic acid molecules and/or vectors of the invention as described herein above may be designed for introduction into cells by e.g. non-chemical methods (electroporation, sonoporation, optical transfection, gene electrontransfer, hydrodynamic delivery or naturally occurring transformation upon contacting cells with the nucleic acid molecule of the invention), chemical-based methods (calcium phosphate, liposomes, DEAE-dextrane, polyethylenimine, nucleofection), particle-based methods (gene gun, magnetofection, impalefection) phage vector-based methods and viral methods including infection. For example, expression vectors derived from viruses such as retroviruses, vaccinia virus, adeno-associated virus, herpes viruses, Semliki Forest Virus or bovine papilloma virus, may be used for delivery of the nucleic acid molecules into targeted cell population. Additionally, baculoviral systems can also be used as vectors in a eukaryotic expression system for the nucleic acid molecules of the invention.

Preferably, the nucleic acid molecules and/or vectors of the invention are designed for transformation of electrocompetent *E. coli* by electroporation or for stable transfection of CHO cells by calcium phosphate-, polyethylenimine- or lipofectamine-transfection (Pham, P. L. et al. [2006] Mol. Biotechnol. 34:225-237; Geisse, S. & Voedisch, B. [2012] Methods Mol. Biol. 899:203-219; Hacker, D. L. et al. [2013] Protein Expr. Purif. 92:67-76).

The present invention relates in a fourth aspect to a host cell transformed with the vector of the third aspect.

The definitions and preferred embodiments of the above aspects of the invention apply mutatis mutandis to the fourth aspect of the invention.

The host cell is preferably a non-human host cell. It will be appreciated that the term "host cell or a non-human host transformed with the vector of the third aspect", in accordance with the present invention, relates to a host cell or a non-human host that comprises the vector of invention.

Suitable prokaryotic hosts comprise e.g. bacteria of the species *Escherichia*, *Corynebacterium* (*glutamicum*), *Pseudomonas* (*fluorescens*), *Lactobacillus*, *Streptomyces*, *Salmonella* or *Bacillus*.

Typical mammalian host cells include, Hela, HEK293, H9, Per.C6 and Jurkat cells, mouse NIH3T3, NS0 and C127 cells, COS 1, COS 7 and CV1, quail QC1-3 cells, mouse L cells, mouse sarcoma cells, Bowes melanoma cells and Chinese hamster ovary (CHO) cells. Most preferred mammalian host cells in accordance with the present invention are CHO cells.

Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells), human dermal and pulmonary fibroblasts, human epithelial cells (nasal, tracheal, renal, placental, intestinal, bronchial epithelial cells), human secretory cells (from salivary, sebaceous and sweat glands), human endocrine cells (thyroid cells), human adipose cells, human smooth muscle cells, human skeletal muscle cells, human leucocytes such as B-cells, T-cells, NK-cells or dendritic cells and stable, immortalized cell lines derived thereof (for example hTERT or oncogene immortalized cells). Appropriate culture media and conditions for the above described host cells are known in the art.

Other suitable eukaryotic host cells are e.g. chicken cells, such as e.g. DT40 cells, or yeasts such as *Saccharomyces cerevisiae, Pichia pastoris, Schizosaccharomyces pombe* and *Kluyveromyces lactis*. Insect cells suitable for expression are e.g. *Drosophila* S2, *Drosophila* Kc, *Spodoptera* Sf9 and Sf21 or *Trichoplusia* Hi5 cells. Suitable zebrafish cell lines include, without being limiting, ZFL, SJD or ZF4.

Appropriate culture media and conditions for the above described host cells are known in the art.

Preferably, the host cell transformed with the vector of the invention is *E. coli*, most preferably *E. coli* selected from *E. coli* supE strain TG1/F$^-$, *E. coli* W3110, *E. coli* JM83, *E. coli* KS272, or *E. coli* BL21. These host cells as well as suitable media and cell culture conditions have been described in the art, e.g. in Gebauer, M. & Skerra, A. [2012] (Meth. Enzymol. 503:157-188).

The host cells in accordance with this embodiment may, e.g., be employed to produce large amounts of the CD98hc-specific binding proteins of the present invention.

The present invention relates in a fifth aspect to a method for the production of the CD98hc-specific binding protein of the first aspect, the method comprising culturing the host cell of the fourth aspect under suitable conditions and isolating the CD98hc-specific binding protein produced.

The definitions and preferred embodiments of the above aspects of the invention apply mutatis mutandis to the fifth aspect of the invention.

In accordance with this embodiment, the vector present in the host of the invention is either an expression vector, or the vector mediates the stable integration of the nucleic acid molecule encoding the CD98hc-specific binding protein of the present invention into the genome of the host cell in such a manner that expression of the protein is ensured. Means and methods for the selection a host cell in which the nucleic acid molecule encoding the CD98hc-specific binding protein of the present invention has been successfully introduced such that expression of the protein is ensured are well known in the art and have been described (Browne, S. M. & Al-Rubeai, M. [2007] Trends Biotechnol. 25:425-432; Matasci, M et al. [2008] Drug Discov. Today: Technol. 5:e37-e42; Wurm, F. M. [2004] Nat. Biotechnol. 22:1393-1398).

Suitable conditions for culturing prokaryotic or eukaryotic host cells are well known to the person skilled in the art. For example, bacteria such as e.g. *E. coli* can be cultured under aeration in Luria Bertani (LB) medium, typically at a temperature from 4 to about 37° C. To increase the yield and the solubility of the expression product, the medium can be buffered or supplemented with suitable additives known to enhance or facilitate both. In those cases where an inducible promoter controls the nucleic acid molecule of the invention in the vector present in the host cell, expression of the polypeptide can be induced by addition of an appropriate inducing agent, such as e.g. anhydrotetracycline as employed in the appended examples. Suitable expression protocols and strategies have been described in the art, e.g. in (Gebauer, M. & Skerra, A. [2012] Meth. Enzymol. 503:157-188) and can be adapted to the needs of the specific host cells and the requirements of the protein to be expressed, if required.

Depending on the cell type and its specific requirements, mammalian cell culture can e.g. be carried out in RPMI, Williams' E or DMEM medium containing 10% (v/v) FCS, 2 mM L-glutamine and 100 U/ml penicillin/streptomycin. The cells can be kept e.g. at 37° C. or at 41° C. for DT40 chicken cells, in a 5% $CO_2$, water-saturated atmosphere. A suitable medium for insect cell culture is e.g. TNM+10% FCS, SF900 or HyClone SFX-Insect medium. Insect cells are usually grown at 27° C. as adhesion or suspension cultures. Suitable expression protocols for eukaryotic or vertebrate cells are well known to the skilled person and can be retrieved e.g. from Sambrook, J & Russel, D. W. [2001], Molecular cloning a laboratory manual (Cold Spring Harbor Laboratory, NY).

Preferably, the method is carried out using either bacterial cells, such as e.g. *E. coli* cells, or mammalian cells, such as e.g. CHO cells. More preferably, the method is carried out using *E. coli* cells or CHO cells and most preferably, the method is carried out using *E. coli* cells.

Methods of isolation of the protein, either from the culture medium and/or from a cell lysate or extract, produced comprise, without limitation, purification steps such as affinity chromatography (preferably using a fusion-tag such as the Strep-tag II or the $His_6$ tag), gel filtration (size exclusion chromatography), anion exchange chromatography, cation exchange chromatography, hydrophobic interaction chromatography, high pressure liquid chromatography (HPLC), reversed phase HPLC or immunoprecipitation. These methods are well known in the art and have been generally described, e.g. in Sambrook, J & Russel, D. W. [2001], Molecular cloning a laboratory manual (Cold Spring Harbor Laboratory, NY), more specifically for Anticalins in e.g. Gebauer, M. & Skerra, A. [2012] (Meth. Enzymol. 503:157-188).

In accordance with the present invention, the term "isolating the CD98hc-specific binding protein produced" refers to the isolation of the CD98hc-specific binding proteins of the present invention.

The present invention relates in a sixth aspect to a protein conjugate or fusion protein comprising the CD98hc-specific binding protein of any one of the first aspect.

The definitions and preferred embodiments of the above aspects of the invention apply mutatis mutandis to the sixth aspect of the invention.

The term "protein conjugate", as used herein, relates to the CD98hc-specific binding protein of the invention to which one or more compounds are coupled (i.e. conjugated).

The compound may be selected from the group consisting of a pharmaceutically active compound, a diagnostically active compound and/or a component modulating serum half-life. The compound may either be a proteinaceous compound or a non-proteinaceous compound. In case the compound is a proteinaceous compound (e.g. a cytokine or chemokine as described herein below), the compound of the sixth aspect is a fusion protein. In case the compound is a non-proteinaceous compound (e.g. radionuclide as described herein below), the compound of the sixth aspect is a protein conjugate.

In the case of a "fusion protein" conjugation may be carried out by recombinant DNA technology using well established techniques. As a result, the conjugate is created as one continuous polypeptide chain through the joining of two or more genes that originally code for separate molecules. Translation of this fusion gene results in a fusion protein with functional properties derived from each of the original molecules. Suitable vectors are known in the art and have been described herein above. It will be appreciated that if the fusion protein of the invention is produced by recombinant DNA technology and may comprise a linker, which linker is preferably a peptide linker as defined further below.

Alternatively, the two (or more) molecules to be conjugated may also be provided separately and linked by chemical methods, as e.g. described in (Hermanson, G. T. [2013] Bioconjugate Techniques, Academic Press, 3rd Ed), either by direct coupling of the molecules via functional or functionalized groups or by indirect coupling employing a linker. In this case, the second (and any further) molecule does not necessarily have to be a protein but may also be e.g. a nucleic acid molecule, a lipid, a non-peptidic ligand, a small molecule drug, a toxic compound or diagnostically and therapeutically relevant radioactive moiety, including metal chelator, and fluorescent tracer.

The term "linker", as used in accordance with the present invention, preferably relates to peptide linkers, i.e. a sequence of amino acids, as well as to non-peptide linkers.

A peptide linker as envisaged by the present invention is a (poly)peptide linker of at least 1 amino acid in length. Preferably, the linker is 1 to 100 amino acids in length. More preferably, the linker is 5 to 50 amino acids in length and even more preferably, the linker is 10 to 20 amino acids in length. Preferably, the linker is a flexible linker using e.g. the amino acids glycine and/or serine. Preferably, the linker sequences are $(Gly_4Ser)_3$, or $(Gly_4Ser)_2$. The length and sequence of a suitable linker depends on the composition of the respective protein conjugate. Methods to test the suitability of different linkers are well known in the art and include e.g. the comparison of the binding affinity or the protein stability or the production yield of the protein conjugate comprising the CD98hc-specific binding protein of the invention to protein conjugates comprising different linkers as well as to the respective CD98hc-specific binding protein of the present invention without a conjugation partner.

As is evident from the above, the linker may in certain embodiments, in particular for protein conjugates, be a non-peptide linker.

The term "non-peptide linker", as used in accordance with the present invention, refers to linkage groups having two or more reactive groups but excluding peptide linkers as defined above. For example, the non-peptide linker may be a polymer having reactive groups at both ends, which individually bind to reactive groups of the molecules of the protein conjugate, for example, an amino terminus, a lysine residue, a histidine residue or a cysteine residue. Suitable reactive groups of polymers include an aldehyde group, a propionic aldehyde group, a butyl aldehyde group, a maleimide group, a ketone group, a vinyl sulfone group, a thiol group, a hydrazide group, a carbonylimidazole group, an imidazolyl group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide linker may be the same or different. For example, the non-peptide linker may have a maleimide group at one end and an aldehyde group at the other end.

Such conjugates can be suitable to confer new characteristics on the CD98hc-specific binding proteins of the present invention.

For example, conjugation can be employed to modify or enhance the solubility of the resulting protein conjugate, to modify or enhance their stability, or to facilitate the purification of said molecules.

Solubility and stability can, for example, be affected by conjugation to larger molecules capable of modulating serum half-life, such as e.g. molecules selected from the group consisting of polyethylene glycol (PEG), immunoglobulin, albumin and albumin-binding peptides.

Purification can be simplified by conjugating the CD98hc-specific binding proteins of the present invention with one or more peptide sequences that confer on the resulting protein conjugate an affinity to certain chromatography column materials. Typical examples for such sequences include, without being limiting, oligohistidine-tags, Strep-tag, glutathione S-transferase, maltose-binding protein or the albumin-binding domain of protein G.

Conjugation may further be employed to functionalize the CD98hc-specific binding proteins of the present invention such that they can be employed as imaging agents in diagnostics. The CD98hc-specific binding protein confers binding specificity to diseased body sites expressing CD98hc, such a cancerous tissue and the imaging agent allows the imaging of the diseased body site. Suitable conjugation partner such as fluorescent dyes or certain enzymes will be discussed herein below.

In addition, conjugation may confer a therapeutic or prophylactic efficacy to the CD98hc-specific binding proteins of the present invention. This aspect is discussed in more detail herein below.

Furthermore, the CD98hc-specific binding proteins of the present invention (or the CD98hc-specific binding protein produced by the method of the invention) can be employed as part of a chimeric antigen receptor (CAR) for T-cell therapy by replacing the tumor antigen-specific single-chain variable fragment (scFv) within the fusion protein e.g. with the CD3-zeta transmembrane and endodomain (Baas, T. [2014] SciBX 7:1-7).

Further non-limiting examples of suitable conjugation partners include chelators such as 1,4,7,10-tetraazacyclodo-decane-1,4,7,10-tetraacetic acid (DOTA) or diethylene triamine pentaacetic acid (DTPA) or their activated derivatives, nanoparticles and liposomes (Nielsen, U. B. et al. [2002] Biochim. Biophys. Acta 1591:109-118).

In accordance with a preferred embodiment of the sixth aspect of the invention, the CD98hc-specific binding protein is conjugated to or is part of a fusion protein wherein the fusion partner is (a) a fluorescent dye or a fluorescent protein,
(b) a radionuclide,
(c) a toxic compound,
(d) a photosensitizer,
(e) an enzyme or truncated version thereof,
(f) a membrane protein or functional fragment thereof retaining the enzyme function,
(g) a contrast agent,
(h) a cytokine,
(i) a chemokine,
(j) a pro-coagulant factor,
(k) an acetylcholineesterase inhibitor,
(l) an inhibitor of Aβ aggregation,
(m) a nucleic acid molecule, or
(n) a nanoparticle.

The fluorescent dye is preferably a component selected from Alexa Fluor, Cy dyes and Fluorescein. Non-limiting further examples of fluorescent proteins are green fluorescent protein (GFP), yellow fluorescent protein (YFP), red fluorescent protein (RFP), cyan fluorescent protein (CFP) and infrared fluorescent protein (IFP).

The radionuclide is preferably either selected from the group of gamma-emitting isotopes, more preferably $^{99}$mTc, $^{123}$I, or $^{111}$In, and/or from the group of positron emitters, more preferably $^{18}$F, $^{64}$Cu, $^{68}$Ga, $^{86}$Y, 89Zr, or $^{124}$I, an d/or from the group of beta-emitter, more preferably $^{131}$I, $^{90}$Y, $^{177}$Lu, or $^{67}$Cu, or from the group of alpha-emitter, preferably $^{213}$Bi, or $^{211}$At. The radionuclide is more preferably a positron emitter since they are particularly suitable for diagnostics, e.g. via positron emission tomography imaging. The radionuclide is most preferably the positron emitter $^{89}$Zr as illustrated in the appended examples.

The toxic compound is preferably a small organic compound or a polypeptide, more preferably a toxic compound selected from the group consisting of calicheamicin, maytansinoid, neocarzinostatin, esperamicin, dynemicin, kedarcidin, maduropeptin, doxorubicin, daunorubicin, auristatin, Ricin-A chain, modeccin, truncated *Pseudomonas* exotoxin A, diphtheria toxin and gelonin.

The photosensitizer is preferably the phototoxic red fluorescent protein KillerRed, haematoporphyrin or bis(triethanolamine)Sn(IV)chlorin $e_6$ (SnChe$_6$).

An enzyme is a protein that catalyzes a particular chemical or biochemical reaction. Antibody-enzyme fusion proteins have been used, for example, to target tumors for cancer therapy in two ways. In one system, an antibody-enzyme is pretargeted to the tumor followed by administration of an inactive prodrug that is converted to its active form by the pretargeted enzyme. This system has been described as antibody-directed enzyme prodrug therapy (ADEPT). Suitable enzymes for prodrug activation will be further discussed herein below in the section on enzymes. The other system uses antibody-enzyme fusion proteins as direct therapeutics, where the enzyme is toxic by itself. The key feature in this approach is that the antibody is used to target and subsequently internalize the toxic enzyme into the tumor cell, which activates cell-death processes. This antibody-enzyme system has been largely applied to deliver ribonucleases. Instead of the discussed antibodies the CD98hc specific binding proteins of the invention are used in accordance with the invention.

Enzymes may also be used for imaging in diagnostics. Conjugation partners in this regard include enzymes capable of catalyzing chromogenic, chemiluminescent or fluorescent reactions, such as e.g. horseradish peroxidase (HRP), luciferase, alpha-galactosidase and alkaline phosphatase (AP). For example, the conjugation partner can also be an enzyme capable of liberating or activating cytotoxic agents that have been brought into the vicinity of the targeted tissue, for example an enzyme for prodrug activation, such as e.g. an enzyme selected from the group consisting of carboxypeptidases, glucuronidases and glucosidases (Bagshawe, K. D. [2009] Curr. Drug Targets 10:152-157; Chen, K.-C. [2011] Bioconjugate Chem. 22:938-948.). For certain applications a truncated version of an enzymes is preferred, for example by omitting a binding domain, provided that the truncated version retains or essentially retains the enzymatic activity of the full-length enzyme. Thus, with respect to the truncated version of the enzymes it is to be understood that they retain or essentially retain the enzymatic activity of the full-length enzyme.

Membrane proteins are proteins that are attached to, or are part of, biological membranes. They include integral membrane proteins, which are permanently anchored or part of the membrane and peripheral membrane proteins, which are only temporarily attached to the lipid bilayer or to other integral proteins. The integral membrane proteins are classified as transmembrane proteins that span across the membrane and proteins that are attached to only one side of the membrane. Membrane proteins are a common type of proteins along with soluble globular proteins, fibrous proteins, and disordered proteins.

A contrast agent as used herein is a substance used to enhance the contrast of structures or fluids within the body in medical imaging. Common contrast agents work based on X-ray attenuation or magnetic resonance signal enhancement.

The cytokine is preferably selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1beta. As it is well known in the art, cytokines may favour a pro-inflammatory or an anti-inflammatory response of the immune system. Thus, depending on the disease to be treated either fusion constructs with a pro-inflammatory or an anti-inflammatory cytokine may be favored. For example, for the treatment of inflammatory diseases in general fusion constructs comprising anti-inflammatory cytokines are preferred, whereas for the treatment of cancer in general fusion constructs comprising pro-inflammatory cytokines are preferred.

The chemokine is preferably selected from the group consisting of IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, eotaxin, Eotaxin-2, 1-309, MPIF-1, 6Ckine, CTACK, MEC, lymphotactin and fractalkine.

A pro-coagulant favours the process by which blood changes from a liquid to a gel, thereby forming a blood clot. The pro-coagulant factor is preferably a tissue factor. The main role of the tissue factor pathway in coagulation is to generate a "thrombin burst", a process by which thrombin, the most important constituent of the coagulation cascade in terms of its feedback activation roles, is released very rapidly.

Acetylcholinesterase (HGNC symbol ACHE; EC 3.1.1.7), also known as AChE or acetylhydrolase, is the primary cholinesterase in the body. It is an enzyme that catalyzes the breakdown of acetylcholine and of some other choline esters that function as neurotransmitters. Inhibitors that reversibly inhibit acetylcholine esterase are explored as treatments for Alzheimer's disease and myasthenia gravis, among others. Non-limiting examples include tacrine and donepezil.

Amyloid beta (Aβ or Abeta) denotes peptides of 36-43 amino acids that are crucially involved in Alzheimer's disease (AD) as the main component of the amyloid plaques found in the brains of Alzheimer patients. The peptides derive from the amyloid precursor protein (APP), which is cleaved by beta secretase and gamma secretase to yield A. Aβ molecules can aggregate to form flexible soluble oligomers which may exist in several forms. Therefore, blocking the initial stages of Aβ peptide aggregation, for example, with small molecules, peptides, peptidomimetics or nanoparticles holds considerable promise as the starting point for the development of new therapies for AD.

The term "nucleic acid molecule" has been defined herein above. It is preferred that the nucleic acid molecule forming part of the protein conjugate of the invention does not encode the CD98hc specific binding protein of the invention.

The term "nanoparticle" as used herein designates particles, generally between 1 and 100 nanometres (nm) in size, with a surrounding interfacial layer. The interfacial layer is an integral part of nanoscale matter, fundamentally affecting its properties. The interfacial layer typically consists of ions, inorganic and organic molecules. Organic molecules coating inorganic nanoparticles are known as stabilizers, capping and surface ligands, or passivating agents. Nanoparticles often possess unexpected optical properties as they are small enough to confine their electrons and produce quantum effects. For example, gold nanoparticles appear deep-red to blue in solution. Nanoparticles of yellow gold and grey silicon are red in color. Hence, nanoparticles are of particular interest for diagnostic applications.

In accordance with another preferred embodiment of the sixth aspect of the invention, the CD98hc-specific binding protein is conjugated to a binding protein, wherein the binding protein is preferably selected from an antibody or immunoglobulin, an antibody fragment and an antibody mimetic, wherein the antibody mimetic is preferably selected from the group consisting of an Anticalin different from the CD98hc-specific binding proteins of the present invention, Affibody, Adnectin, DARPin, Avimer, Nanofitin, Affilin, β-Wrapin, ADAPT, Monobody, Resin, FingR, Pronectin, Centyrin, Affimer, Adhiron, Affitin, αRep, Repebody, body, Fynomer and Kunitz domain protein.

In accordance with this preferred embodiment, the CD98hc-specific binding proteins of the present invention are conjugated to at least one other binding protein that either targets a different epitope on CD98hc or that targets a molecule other than CD98hc, such as e.g. other proteins, macromolecules or low molecular weight ligands, thereby creating bi-specific (or higher) binding molecules. Non-limiting examples of such binding proteins include an antibody or immunoglobulin, an antibody fragment and an antibody mimetic.

The term "antibody", also known as an immunoglobulin (Ig), as used in accordance with the present invention comprises, for example, polyclonal or monoclonal antibodies. Furthermore, comprised in the term "antibody" are fragments or multimeric formats, such as minibodies, diabodies, tribodies or triplebodies, or tetrabodies (see, for example, Harlow and Lane "Antibodies, A Laboratory Manual", Cold Spring Harbor Laboratory Press, 1998; Harlow and Lane "Using Antibodies: A Laboratory Manual" Cold Spring Harbor Laboratory Press, 1999; Altshuler E P, Serebryanaya D V, Katrukha A G. 2010, Biochemistry (Mosc)., vol. 75(13), 1584; Holliger P, Hudson P J. 2005, Nat Biotechnol., vol. 23(9), 1126). The multimeric formats in particular comprise bispecific antibodies that can simultaneously bind to two different types of antigen. The first antigen can be found on the protein of the invention. The second antigen may, for example, be a tumor marker that is specifically expressed on cancer cells or a certain type of cancer cells. Non-limiting examples of bispecific antibodies formats are Biclonics (bispecific, full length human IgG antibodies), DART (Dual-affinity Re-targeting Antibody) and BITE (consisting of two single-chain variable fragments (scFvs) of different antibodies) molecules (Kontermann and Brinkmann (2015), Drug Discovery Today, 20(7):838-847). The term "antibody" also includes embodiments such as chimeric (human constant domain, non-human variable domain), single chain and humanised (human antibody with the exception of non-human CDRs) antibodies.

In accordance with the present invention, antibody fragments comprise, inter alia, Fab or Fab' fragments, F(ab')$_2$, Fv or scFv fragments, single domain VH, VL or V-like domains, such as VhH or V-NAR-domains, as well as multimeric formats such as minibodies, diabodies, tribodies, triplebodies, tetrabodies or chemically conjugated Fab'-multimers (see, for example, Altshuler, E. et al. [2010] Biochem. (Mosc.) 75:1584-1605 or Holliger, P. & Hudson, P. J. [2005] Nat. Biotechnol. 23:1126-1136).

In accordance with the present invention, antibody fragments also comprise Fc domains of an antibody. Preferably, the Fc domain is one or more human functional Fc domain (s) which allow(s) for extending the in vivo half-life of the proteins of the invention and some of which direct a mammal's immune response to a site of specific target binding of the inventive polypeptide component of the fusion protein, e.g. in therapeutic, prophylactic and/or diagnostic applications as described herein below. The proteins of the invention can be fused either to the N- or C-terminus of one or more functional Fc domains or to both the N- and the C-terminus of one or more Fc domains. It is preferred that the fusion proteins of the invention comprise multimers, preferably tetramers, trimers or most preferably dimers of the polypeptides of the invention fused to at least one side, preferably to the N-terminus of one or more, preferably one Fc domain.

A "functional Fc domain" of an antibody is a term well known to the skilled artisan and defined on the basis of papain cleavage of antibodies. Depending on the amino acid sequence of the constant region of their heavy chains, immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called [alpha], [delta], [epsilon], [gamma], and [mu], respectively. The functional Fc domain of an antibody is directly involved in ADCC (antibody-dependent cell-mediated cytotoxicity) and CDC (complement-dependent cytotoxicity) based on complement activation, C1q binding and Fc receptor binding. The four human IgG isotypes bind different receptors, such as the neonatal Fc receptor, the activating Fc gamma receptors, FcγRI, FcγRIIa, and FcγRIIIa, the inhibitory receptor FcγRIIb, and the complement component C1q with different affinities, yielding very different activities. It is known that the affinities to activating and inhibiting receptors of an Fc domain of a human antibody can be engineered and modified (see Strohl W. (2009) Curr Opin Biotechnol, 20, p. 685-691). The invention therefore comprises (a) Fc fusion(s) which contain(s) a functional Fc domain of preferably human origin, preferably (a) human functional Fc domain(s) of an IgG1 antibody which allow(s) for extending the in vivo half-life of the polypeptides of the invention.

In a more preferred embodiment of the present invention, the Fc domain is one or more engineered human functional Fc domains of an IgG1 with activating or silenced effector functions, preferably one or more engineered human functional Fc domains of an IgG1 with silenced effector functions, and even more preferably one or more engineered human functional Fc domains of an IgG1 with silenced effector functions with a mutation in L234 and L235, numbering according to Kabat (see Johnson G. and Wu T. T. (2000) Nucleic Acids Res. 28, 214-218), and most preferred with the mutation L234A and L235A.

As used herein, the term "antibody mimetics" refers to compounds or proteins which, like antibodies, can specifically bind antigens, such as CD98hc in the present case, but which are not structurally related to antibodies. Antibody mimetics are usually artificial peptides or proteins with a molar mass of about 3 to 30 kDa. Non-limiting but preferred examples of an antibody mimetic are an Anticalin, Affibody, Adnectin, DARPin, Avimer, Nanofitin, Affilin, β-Wrapin, ADAPT, Monobody, Resin, FingR, Pronectin, Centyrin, Affilin, Affimer, Adhiron, Affitin, αRep, Repebody, i-body, Fynomer or Kunitz domain protein.

"Anticalins" have already been discussed herein above. In accordance with the present invention, they are an emerging class of clinical-stage biopharmaceuticals with high potential as an alternative to antibodies. Anticalin molecules are generated by combinatorial design from natural lipocalins, which are abundant plasma proteins in humans, and reveal a simple, compact fold dominated by a central β-barrel, supporting four structurally variable loops that form a binding site. Reshaping of this loop region results in Anticalin proteins that can recognize and tightly bind a wide range of medically relevant targets, from small molecules to peptides and proteins, as validated by X-ray structural analysis. Their robust format allows for modification in several ways, both as fusion proteins and by chemical conjugation, for example, to tune plasma half-life. Antagonistic Anticalin therapeutics have been developed for systemic administration (e.g., PRS-080: anti-hepcidin) or pulmonary delivery (e.g. PRS-060/ AZD1402: anti-interleukin [IL]-4-Ra). Moreover, Anticalin proteins allow molecular formatting as bi- and even multi-specific fusion proteins, especially in combination with antibodies that provide a second specificity. For example, PRS-343, which has recently entered clinical-stage development, combines an agonistic Anticalin targeting the costimulatory receptor 4-1BB with an antibody directed against the cancer antigen human epidermal growth factor receptor 2 (HER2), thus offering a novel treatment option in immuno-oncology (Rothe and Skerra (2018) BioDrugs 32, 233-243.).

"Affibodies", in accordance with the present invention, are a family of antibody mimetics derived from the Z-domain of staphylococcal protein A. Affibodies are structurally based on a three-helix bundle domain. An affibody has a molecular mass of around 6 kDa and is stable at high temperatures and under acidic or alkaline conditions. Target specificity is obtained by randomisation of amino acids located in two alpha-helices involved in the binding activity of the parent protein domain (Feldwisch, J & Tolmachev, V. [2012] Methods Mol. Biol. 899:103-126).

"Adnectins" and also "Monobodies", in accordance with the present invention, are based on the 10th extracellular domain of human fibronectin Ill (10Fn3), which adopts an Ig-like sandwich fold with 2 to 3 exposed loops, but lacks the central disulphide bridge (Gebauer, M. & Skerra, A. [2009] Curr. Opin. Chem. Biol. 13:245-255). Adnectins and Monobodies with the desired target specificity can be genetically engineered by introducing modifications into specific loops or other surface areas of the protein.

"DARPins", in accordance with the present invention, are designed ankyrin repeat domains that provide a rigid interface arising from typically three repeats corresponding to an artificial consensus sequence, whereby six positions per repeat are randomised. Consequently, DARPins lack structural flexibility (Gebauer, M. & Skerra, A. [2009] Curr. Opin. Chem. Biol. 13:245-255).

The term "Avimer", as used herein, refers to a class of antibody mimetics which consist of two or more peptide sequences of 30 to 35 amino acids each, which are derived from A-domains of various membrane receptors and which are connected by linker peptides. Binding of target molecules occurs via the A-domain and domains with desired binding specificity can be selected, for example, by phage display techniques. The target specificity of the different A-domains contained in an avimer may, but do not have to be identical (Weidle U H, et al., (2013), Cancer Genomics Proteomics; 10(4):155-68).

"Nanofitins" and also an "Affitins" are antibody mimetic proteins that are derived from the DNA binding protein Sac7d of *Sulfolobus acidocaldarius*. Nanofitins and Affitins usually have a molecular weight of around 7 kDa and are designed to specifically bind a target molecule by randomising the amino acids on the binding surface (Mouratou B, Behar G, Paillard-Laurance L, Colinet S, Pecorari F., (2012) Methods Mol Biol.; 805:315-31 and Koide et al. 1998, J. Mol. Biol. 284:1141-51).

The term "Affilin", as used herein, refers to antibody mimetics that are developed by using either gamma-B crystalline or ubiquitin as a scaffold and modifying aminoacids on the surface of these proteins by random mutagenesis. Selection of affilins with the desired target specificity is effected, for example, by phage display or ribosome display techniques. Depending on the scaffold, affilins have a molecular weight of approximately 10 or 20 kDa. As used herein, the term affilin also refers to di- or multimerised forms of affilins (Weidle U H, et al., (2013), Cancer Genomics Proteomics; 10(4):155-68).

As used herein, the term "β-Wrapins" designates affibody protein homodimers with a disulfide bond between the pair of Cys28 residues connecting the two identical monomer subunits, referred to as subunits 1 and 2. The scaffold used in engineering β-wrapins is ZAβ$_3$, an Aβ-binding affibody protein that not only prohibits the initial aggregation of Aβ monomers into toxic forms, but also dissociates pre-formed oligomeric aggregates by sequestering and stabilizing a β-hairpin conformation of Aβ monomers (Orr et al. (2018), Computers & Chemical Engineering, 116(4):322-332).

As used herein, the term "ABD-Derived Affinity Proteins (ADAPT)" refers to a class of antibody mimetics that has been created using the albumin-binding domain (ABD) of streptococcal protein G as a stable protein scaffold (Garousi et al (2015), Cancer Res.; 75(20):4364-71). By diversifying a surface of the domain that is not directly involved in albumin binding, molecules can be selected to bind a novel target and still retain their ability to bind albumin. This strategy has been used to select binders to a number of proteins, for example, the cancer-related epidermal growth factor receptor 3.

As used herein "Raslns" are 10FnIII-based antibody mimetics. Hence, they use the 10th domain of human fibronectin as their scaffold Raslns are disulfide-free intrabodies. They were shown to be stable inside cells and also when fused with a fluorescent protein label (Cetin eat al. (2017), J Mol Biol.; 429(4):562-573).

As used herein, the trem "FingRs (Fibronectin intrabodies generated with mRNA display)" designates recombinant antibody-like proteins also being based on the 10FnIII scaffold (Gross eat al. (2013), Neuron.; 78(6): 971-985.).

As used herein, the term "Pronectins" designates recombinant antibody-like proteins being based on the fourteenth type-III scaffold of human fibronectin (14Fn3). The well-characterized fibronectin protein is prevalent throughout the human body. Human fibronectin, an extracellular protein, is naturally abundant in human serum. Intelligent loop-diversity has been designed to closely mimic the natural human repertoire and avoid sequence immunogenicity. The intrinsic properties of a Pronectin align with the pharmacological properties needed to make it a successful drug, including high potency, specificity, stability, favorable small size, and high-yield production in *E. coli* and yeast (http://www.protelica.com/pronectin_tech.html).

As used herein, the term "Centyrins" designates recombinant antibody-like proteins being based on the consensus tenascin FN3 framework (Tencon) (Diem et al. (2014), Protein Eng., Des. and Sel. 27, 419-429). Centyrins against different targets, e.g. human c-MET, rTNFα and mIL-17A, were generated.

As used herein, "Affimers" refer to small proteins that bind to target molecules with similar specificity and affinity to that of antibodies. These engineered non-antibody binding proteins are designed to mimic the molecular recognition characteristics of monoclonal antibodies in different applications. In addition, these affinity reagents have been optimized to increase their stability, make them tolerant to a range of temperatures and pH, reduce their size, and to increase their expression in *E. coli* and mammalian cells. Derived from the cysteine protease inhibitor family of cystatins, which function in nature as cysteine protease inhibitors, these 12-14 kDa proteins share the common tertiary structure of an α-helix lying on top of an antiparallel β-sheet (Tiede et al. (2017), eLife.; 6: e24903).

The class of recombinant antibody-like proteins designated as "Adhirons" herein is based on a phytocystatin consensus sequence as the scaffold (Tiede et al. (2014) Protein Eng. Des. Sel. 27, 145-55).

The class of recombinant antibody-like proteins designated as "αRep" herein is derived from alpha-helicoidal HEAT-like repeat protein scaffolds. In more detail, The αRep proteins are derived from a natural family of modular proteins comprising alpha-helical repeats, related to HEAT repeats, named after Huntingtin, the elongation factor 3 (EF3), the protein phosphatase 2A (PP2A), and the yeast kinase TOR. The association of several HEAT repeats forms alpha-solenoids of various lengths, which are naturally found in a number of cellular proteins involved in intracellular transport and protein-protein interaction (Hadpech et al. (2017), Scientific Reports; 7:Article number16335).

As used herein, the term "Repebodies" designates recombinant antibody-like proteins which are composed of leucine-rich repeat (LRR) modules. In more detail, the binding scaffold of Repebodies is based on variable lymphocyte receptors, which are nonimmunoglobulin antibodies composed of LRR modules in jawless vertebrates. A template scaffold was first constructed by joining consensus repeat modules between the N- and C-capping motifs of variable lymphocyte receptors. The N-terminal domain of the template scaffold was redesigned based on the internalin-B cap by analyzing the modular similarity between the respective repeat units using a computational approach (Lee at al. (2012), Proc Natl Acad Sci; 109(9): 3299-3304).

As used herein, the term "i-bodies" refers to recombinant antibody-like proteins built on the scaffold of a human protein and engineered with two loops that mimic the shape of shark antibodies. These loops are responsible for binding or interacting with a particular target (in circulation or on a cell) that is causing disease. The i-body is a human analogue of the antigen binding domain of the shark antibody, which combines the advantages of monoclonal antibodies (high target specificity and affinity) with the beneficial stability features of small molecules (https://www.ibodies.eu/).

As used herein, the term "Fynomer" refers to a non-immunoglobulin-derived binding polypeptide derived from the human Fyn SH3 domain. Fyn SH3-derived polypeptides are well-known in the art and have been described e.g. in Grabulovski et al. (2007) JBC, 282, p. 3196-3204, WO 2008/022759, Bertschinger et al (2007) Protein Eng Des Sel 20(2):57-68, Gebauer and Skerra (2009) Curr Opinion in Chemical Biology 13:245-255, or Schlatter et al. (2012), MAbs 4:4, 1-12).

A "Kunitz domain peptide" is derived from the Kunitz domain of a Kunitz-type protease inhibitor such as bovine pancreatic trypsin inhibitor (BPTI), amyloid precursor protein (APP) or tissue factor pathway inhibitor (TFPI). Kunitz domains have a molecular weight of approximately 6 kDa and domains with the required target specificity can be selected by display techniques such as phage display (Weidle et al., (2013), Cancer Genomics Proteomics; 10(4): 155-68).

The present invention relates in a seventh aspect to a pharmaceutical composition or a diagnostic composition comprising at least one of (i) the CD98hc-specific binding protein of the first aspect; (ii) the nucleic acid molecule of the second aspect; (iii) the vector of the third aspect; (iv) the host cell of the fourth, and/or (v) the protein conjugate or fusion protein of the sixth aspect.

The term "composition", as used in accordance with the present invention, relates to a composition which comprises at least one of the recited compounds. It may, optionally, comprise further molecules capable of altering the characteristics of the compounds of the invention thereby, for example, stabilizing, modulating and/or enhancing their function. The composition may be in solid or liquid form and may be, inter alia, in the form of (a) powder(s), (a) tablet(s) or (a) solution(s).

In one embodiment, the composition is a pharmaceutical composition.

In accordance with the present invention, the term "pharmaceutical composition" relates to a composition for administration to a patient, preferably a human patient. The pharmaceutical composition of the invention comprises the compounds recited above. The pharmaceutical composition of the present invention may, optionally and additionally, comprise a pharmaceutically acceptable carrier. "Pharmaceutically acceptable carrier" means a non-toxic solid, semisolid or liquid filler, diluent, encapsulating material or formulation auxiliary of any type. Examples of suitable pharmaceutically acceptable carriers are well known in the art and include sodium chloride solutions, phosphate buffered sodium chloride solutions, water, emulsions, such as oil/water emulsions, various types of wetting agents, sterile solutions, organic solvents etc. Such pharmaceutically acceptable carriers often contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or further immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as ethylenediaminetetraacetic acid (EDTA); sugar alcohols such as mannitol or sorbitol; counterions such as sodium; and/or nonionic surfactants such as polysorbates, poloxamers, or PEG. The pharmaceutical composition may comprise further agents depending on the intended use of the pharmaceutical composition, such as e.g. antitumoral agents for use in the treatment of tumors.

Administration of pharmaceutical compositions of the invention may be effected by different ways, e.g., by intravenous, intraperitoneal, subcutaneous, intramuscular, intradermal, intranasal or intrabronchial administration. Accordingly, it is preferred that the pharmaceutically acceptable carrier is a carrier suitable for these modes of administration. Most preferably, the carrier is a solution that is isotonic with the blood or tissue fluid of the recipient. Compositions comprising such carriers can be formulated by well known conventional methods. Generally, the formulations are prepared by contacting the components of the pharmaceutical composition uniformly and intimately with liquid carriers or finely divided solid carriers or both. Then, if necessary, the product is shaped into the desired formulation.

The pharmaceutical compositions can be administered to the subject at a suitable dose. The dosage regimen will be determined by the attending physician and clinical factors. As is well known in the medical arts, dosages for a particular patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The pharmaceutical composition may be for administration once or for a regular administration over a prolonged period of time. Generally, the administration of the pharmaceutical composition should be in the range of for example 1 µg/kg of body weight to 50 mg/kg of body weight for a single dose. However, a more preferred dosage might be in the range of 10 µg/kg to 20 mg/kg of body weight, even more preferably 100 µg/kg to 10 mg/kg of body weight and even more preferably 500 µg/kg to 5 mg/kg of body weight for a single dose. Similarly, the administration of the pharmaceutical composition should generally be in the range of for example 1 µg binding protein of the invention/kg of body weight to 50 mg binding protein of the invention/kg of body weight fora single dose. However, a more preferred dosage might be in the range of 10 µg binding protein of the invention/kg to 20 mg binding protein of the invention/kg of body weight, even more preferably 100 µg binding protein of the invention/kg to 10 mg binding protein of the invention/kg of body weight and even more preferably 500 µg binding protein of the invention/kg to 5 mg binding protein of the invention/kg of body weight for a single dose.

The components of the pharmaceutical composition to be used for therapeutic administration must be sterile. Sterility is readily accomplished for example by filtration through sterile filtration membranes (e.g., 0.2 µm membranes).

The pharmaceutical composition may be particularly useful for the treatment of tumors and/or neurological diseases, as disclosed below.

In another embodiment, the composition of the invention is a diagnostic composition.

In accordance with the present invention, the term "diagnostic composition" relates to compositions for diagnosing individual patients for their potential response to or curability by the pharmaceutical compositions of the invention. The diagnostic composition of the invention comprises at least one of the compounds recited above. The diagnostic composition may further comprise appropriate buffer(s) etc.

The components of the pharmaceutical or diagnostic composition can be packaged in a container or a plurality of containers, for example, sealed ampoules or vials, as an aqueous solution or as a lyophilized formulation for reconstitution. As an example of a lyophilized formulation, 10-ml vials are filled with 5 ml of 1% (w/v) or 10% (w/v) of an aqueous solution, and the resulting mixture is lyophilized. A solution for use is prepared by reconstituting the lyophilized compound(s) using either e.g. water-for-injection for therapeutic uses or another desired solvent, e.g. a buffer, for diagnostic purposes. Preservatives and other additives may also be present such as, for example, antimicrobials, antioxidants, chelating agents, and inert gases and the like.

The diagnostic compositions of the present invention can be used in in vivo as well as in in vitro or ex vivo diagnostic methods well known in the art. For example, the above described in vivo imaging methods using fluorescent or radioactive labels can be employed to trace the presence of CD98hc to specific tissues or tumors and/or their metastases. Furthermore, methods carried out outside the patient's body such as e.g. immunohistochemical staining of tissues or cells obtained from the patient can be employed for grading the severity of a particular cancer. In addition, measuring the amount of CD98hc in brain tissue can be of diagnostic value.

The various components of the composition may be packaged as a kit with instructions for use.

The present invention relates in an eighth aspect to the CD98hc-specific binding protein of the first aspect, the nucleic acid molecule of the second aspect, the vector of the third aspect, the host cell of the fourth aspect, or the protein conjugate or fusion protein of any one of the sixth aspect for use in therapy and/or diagnosis, preferably for use in treating or diagnosing a disease in the brain and/or the spinal cord.

CD98hc is highly expressed in various cancer types including NSCLC, prostate cancer, lymphoma, leukemia, gastric cancer, osteosarcoma, renal cell carcinoma, breast cancer and biliary tract cancer (Ansaris et al. (2018), British Journal of Cancervolume, 118:1115-1122). Furthermore, the examination of the expression of CD98hc or CD98 light chains in solid tumors has shown that their expression is correlated with progressive or metastatic tumors. Genetic modulation of CD98 expression in human cell lines and in animal models has established a causal link between CD98 and cancer; CD98 promotes transformation and tumor growth.

Furthermore, CD98 overexpression drives both anchorage independence and tumorigenesis, and the degree of transformation correlates with the level of CD98hc present in the cells.

The blood-brain barrier (BBB) poses a major challenge for developing effective therapies for neurological diseases because drugs such as antibodies are not or not effectively transported across the BBB. Generally, only ~0.1% of circulating antibodies cross the intact BBB, which severely limits the therapeutic utility of antibody therapeutics for CNS disorders. CD98hc has been discovered as providing a robust receptor-mediated transcytosis pathway for enhancing brain uptake of therapeutic antibodies. For example, brain concentrations of anti-CD98hc antibodies were about 9 to 11-fold higher than that of control IgG, respectively, at 24 hr postdose (Zuchero et al. (2016), Neuron, Volume 89(1):70-82). As is commonly known, the central nervous system (CNS) is the part of the nervous system consisting of the brain and the spinal cord. Hence, once a drug has crossed the BBB it can reach diseases being located in the brain and/or the spinal cord.

The present invention relates in a ninth aspect to the CD98hc-specific binding protein of to any one of the first aspect, the nucleic acid molecule of the first aspect, the vector of the first cell of the first aspect, or the protein conjugate or fusion protein of any one of the first aspect for use in the therapy and/or diagnosis of a tumor or a neurological disease, wherein the neurological disease is preferably located in the brain and/or the spinal cord.

As discussed above, CD98hc is in particular a suitable target to treat and diagnose tumors and neurological disease. This is because tumors highly express CD98hc on the one hand and CD98hc-specific binding protein can cross the BBB on the other, thereby in particular reaching neurological diseases in the brain and/or the spinal cord.

The term "tumor", in accordance with the present invention, refers to a class of diseases or disorders characterized by uncontrolled division of cells and encompasses all types of tumors, such as e.g. cancerous tumors and benign tumors as well as solid tumors and non-solid tumors. Cancerous tumors are further characterized by the ability of these tumors to spread, either by direct growth into adjacent tissue through invasion, or by implantation into distant sites by metastasis (where tumor cells are transported through the bloodstream or lymphatic system). Preferably, the tumor is a cancerous tumor or cancer. Non-limiting but preferred examples of tumors are NSCLC, prostate cancer, lymphoma, leukemia, gastric cancer, osteosarcoma, renal cell carcinoma, breast cancer, brain cancer, glioblastoma and biliary tract cancer.

The term "neurological diseases", in accordance with the present invention, refers to disorders that affect the nervous system, i.e. the brain, spinal cord, and the nerves, preferably the brain and/or the spinal cord. Preferably, the neurological diseases are selected from the group consisting of Alzheimer disease (AD), Multiple sclerosis, dementia, stroke, amyotrophic lateral sclerosis (ALS), schizophrenia, diabetic neuropathy, severe head injury (SHI), traumatic brain injury (TBI), neuropathic pain, inflammatory pain, drug addiction, as well as neurodegenerative diseases such as Parkinson's disease and Huntington's disease. For example, AD, Parkinson's disease, and schizophrenia affect the brain.

All the cancer types and neurological diseases referred to herein are well known to the skilled person and are defined in accordance with the pertinent art and the common general knowledge of the skilled person.

Unless otherwise defined, all technical and scientific terms used herein have the same meaning as commonly understood by one of ordinary skill in the art to which this invention belongs. In case of conflict, the patent specification including definitions, will prevail.

All the sequences accessible through the Database Accession Numbers cited herein are within the scope of the present invention and also include potential future updates in the database, in order to account for future corrections and modifications in the entries of the respective databases, which might occur due to the continuing progress of science.

All amino acid sequences provided herein are presented starting with the most N-terminal residue and ending with the most C-terminal residue (N-C), as customarily done in the art, and the one-letter or three-letter code abbreviations as used to identify amino acids throughout the present invention correspond to those commonly used for amino acids.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims.

The figures show.

FIG. 1. Phage Display selection of lipocalin variants with affinity towards the ectodomain of hCD98hc. (A) Graphical depiction of the CD98 heavy chain (CD98hc) covalently linked to a CD98 light chain, illustrating the two main biochemical functions fulfilled by CD98hc. The structure of CD98hc ectodomain used for phage display selection of Anticalins is shown as a molecular surface model. (B) Analytical size exclusion chromatography of the CD98hc-specific lipocalin variants P1E4, P3A12 and P3D11 selected via phage display and wtLcn2, showing a monomeric elution behavior with just minor aggregate formation (eluting at Vo). (C) SPR real-time binding analysis of the picomolar affinity variant P3D11 for hCD98hcED. The deduced kinetic constants are listed in Table 1.

Figure 2:
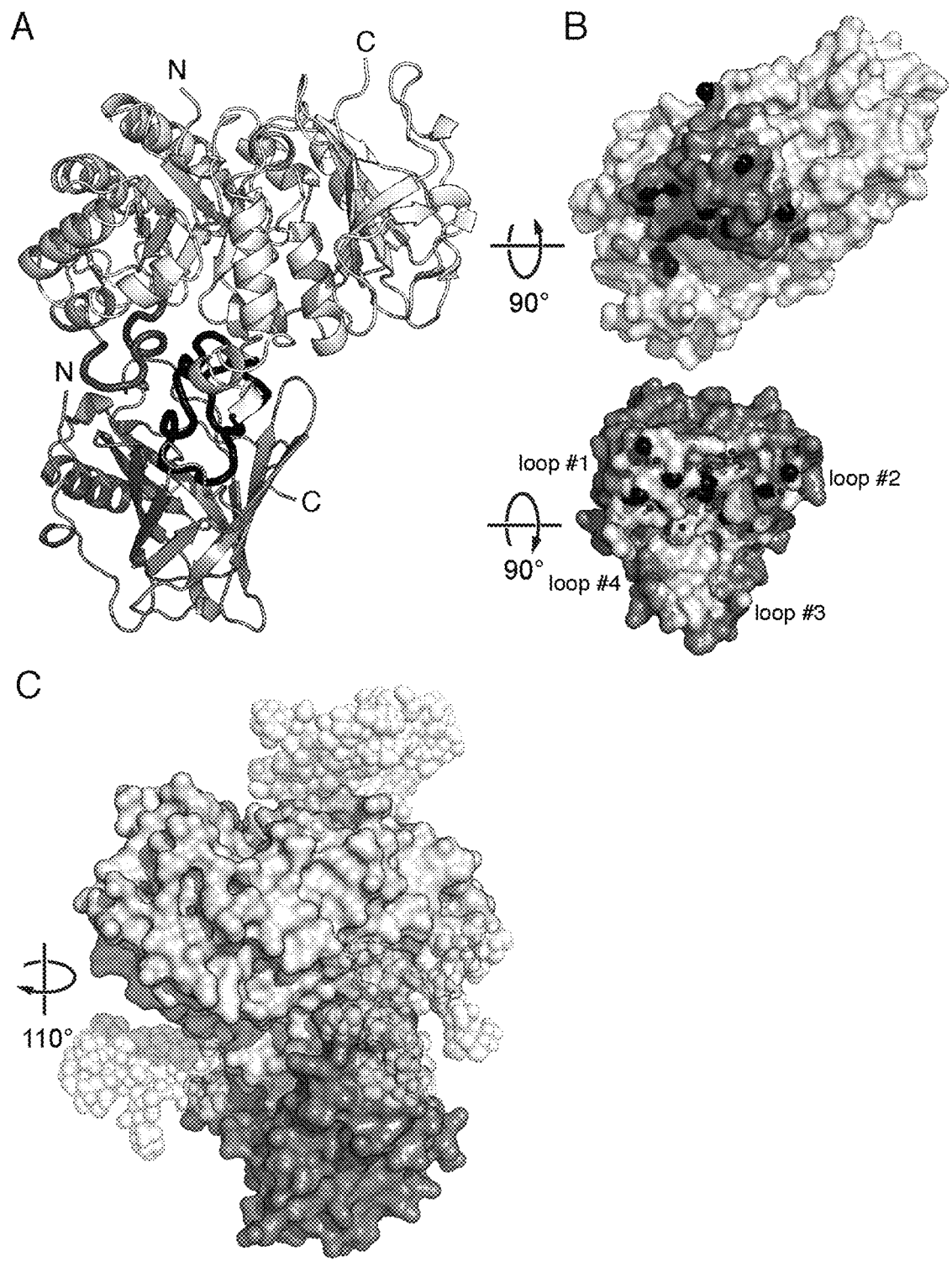

FIG. 2. X-ray structure of Anticalin P3D11 in complex with the human CD98hc ectodomain. (A) Cartoon representation of the P3D11●hCD98hcED complex (P3D11 dark gray, hCD98hcED light gray). The epitope loops L1 and L2 of hCD98hc are highlighted in dark gray and black (both in bold), respectively. (B) Dissection of the contact interface. Both complex components are shown as molecular surface and rotated by 90° in opposite directions to visualize their interface. P3D11 interface residues are colored light grey, in order to indicate contacts with loops L1 and L2 of hCD98hc (see panel A). Contacting residues of hCD98hc with P3D11 are colored dark gray. Hydrogen bond donors and acceptors are indicated in black for both molecules. Water molecules that mediate hydrogen bonds are depicted as dark spheres. (C) Surface representation of P3D11●hCD98hcED complex in context of its four complex N-glycans (spheres), rotated by 110° with regard to panel A.

Figure 3:
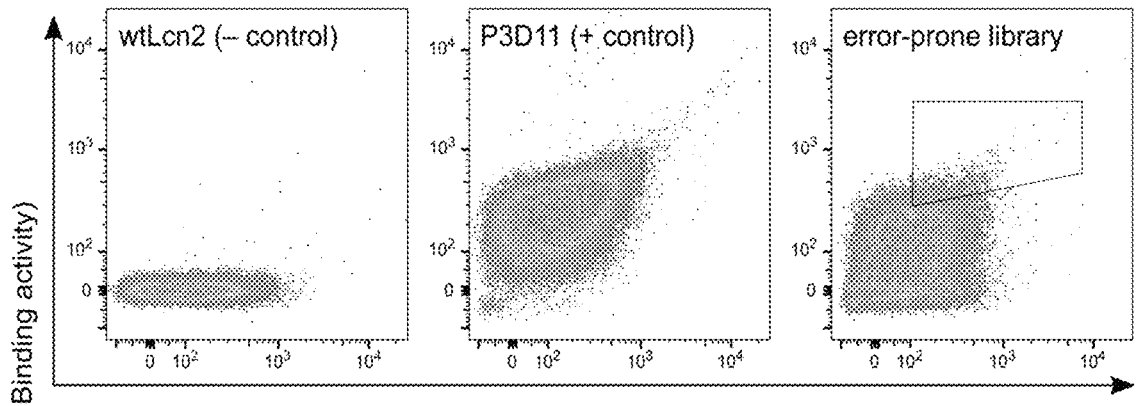
Figure 3:
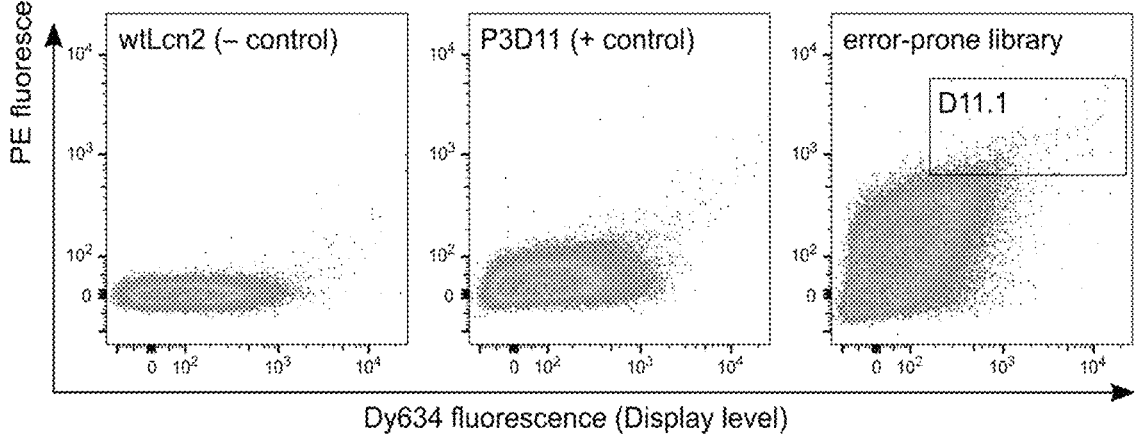
Figure 3:
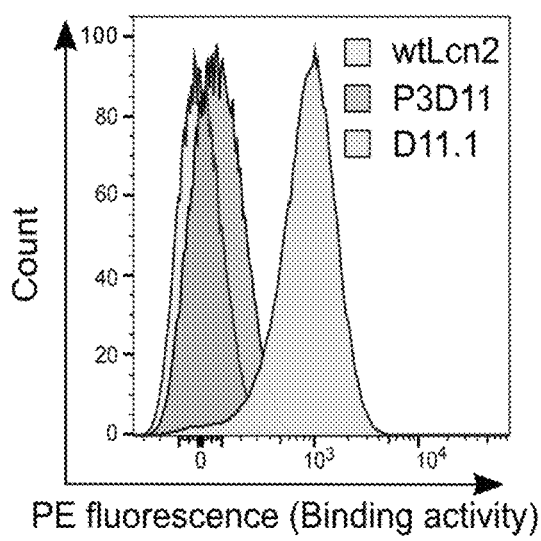
Figure 3:
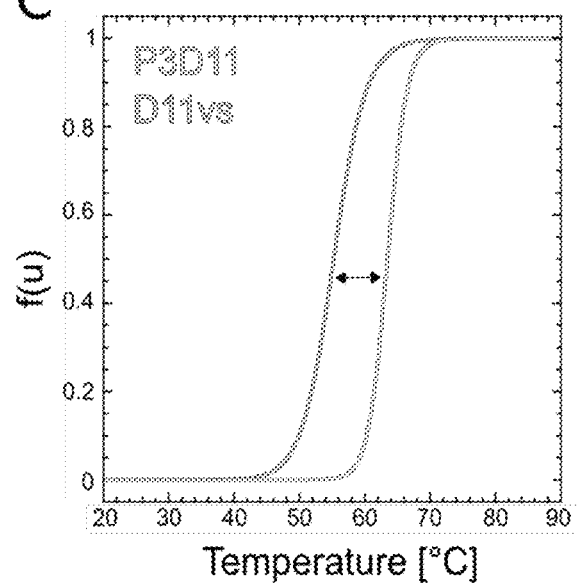

FIG. 3. Affinity and stability engineering of the lipocalin variant P3D11 via bacterial cell surface display. (A) FACS analysis of *E. coli* cells presenting wtLcn2 (left), starting variant P3D11 (middle) or the error-prone library (right) incubated with 100 nM (round 1, upper panel) or 1 nM (round 7, lower panel) biotinylated BAP-huCD98hcED, respectively. (B) Single clone FACS analysis of wtLcn2, P3D11 and an identified variant depicted D11.1 after seven selection cycles using 1 nM BAP-huCD98hcED (FIG. 11). (C) Thermal denaturation of P3D11 and D11vs using CD spectroscopy.

FIG. 4. Cytofluorometry and immunofluorescence microscopy of CD98hc expressing human cancer cell lines using the PASylated lipocalin variant D11vs. (A) Flow cytometry analysis of three B-cell lymphoma (SU-DHL-4, Raji and Ramos) and two prostate carcinoma (DU-145 and PC-3) cell lines with Cy5.5 labeled PASylated D11vs (gray60 histogram). For competition of D11vs binding, a 10-fold molar excess of either unlabeled D11vs-PAS200 or soluble hCD98hcEDg was used (gray80 and gray50 histograms, respectively). The respective cell line without the addition of a labeled binding protein is shown in gray70. Immunocytochemical detection of hCD98hc using Cy5.5 labeled PASylated D11vs is shown for (B) Ramos, (C) PC-3 and (D) Caco-2 cells (middle panel). As controls for specific recognition of hCD98hcED by D11vs, cells were stained with wtLcn2 (left panel) or binding was competed using a 10-fold molar excess of unlabeled D11vs-PAS200 (right panel). Cell nuclei were stained with DAPI.

FIG. 5. In vivo $^{89}$Zr PET/CT imaging study in a prostate carcinoma xenograft model. (A) Mice (♀) bearing PC-3 xenografts were i.v. injected with 2.85±0.15 MBq $^{89}$Zr●D11vs-PAS200-DFO followed by PET/CT imaging 24, 48 and 72 h post injection. Signals were detected in the xenograft tumor (arrowheads), liver (I), kidneys (k), bladder (bl) and the joints (*). (B) PET images were analyzed by threshold-based image segmentation (lower threshold at 50% of the hottest voxel), activity trajectories are depicted. Error bars indicate standard deviation and an unpaired student's t-test was performed between the blocked and non-blocked group (* $p<0.05$). Epitope blocking was achieved by i.v. injection of a 100-fold molar excess of the cold PASylated Anticalin 2 h before $^{89}$Zr-tracer injection. (C) Explanted tumors were split in transversal direction, from one half consecutive cryosections of 10 μm were prepared followed by autoradiography and HE staining. (D) Second half of the tumor was embedded in paraffin and sections were stained for HE, CD31 (blood vessels) and CD98hc using appropriate antibodies.

FIG. 6. In vivo and ex vivo PET/CT imaging and biodistribution analysis. (A) Mice (♂) bearing PC-3 tumors were injected with 3.96±0.12 MBq $^{89}$Zr●D11vs-PAS200 and (B) mice in the blocking group additionally received 250-fold molar excess of unlabeled D11vs-PAS200 2 h before the radiotracer injection. For each mouse in each cohort the in vivo PET/CT (left panel), ex vivo PET/CT (middle panel) and a photograph of the tumors (right panel) are depicted. (C) For biodistribution analysis mice organs were explanted and subsequently weight and radioactivity were determined. Error bars show standard deviation and an unpaired student's t-test was performed between the blocked and unblocked group (** $p<0.005$).

FIG. 7. Biochemical characterization of the monobiotinylated human and murine CD98hc ectodomain soluble produced in *E. coli* or HEK cells. (A) Schematic illustration of the covalently linked CD98hc/CD98lc heterodimer and plasmid constructs used for the soluble expression of unglycosylated and glycosylated m/hCD98hc ectodomain. The extracellular domain of CD98hc soluble expressed and used for Anticalin selection is framed by a rectangle (B) Apparent mass determination of the glycosylated and unglycosylated m/hCD98hcED using analytical SEC (Table 2) verifying a considerable mass increase due to glycosylation. (C) Differences in electrophoretic mobility of unglycosylated and glycosylated m/hCD98hcED during SDS-PAGE, confirming glycosylation after production in eukaryotic HEK cells, while absent after production in E. coli. (D) Enzymatic processing of N-linked sugars from m/hCD98hcEDg by Peptide-N-Glycosidase F (PNGase F) and subsequent comparison with the fully glycosylated ectodomain via SDS-PAGE.

FIG. 8. Sequence analysis, expression and functional characterization of the selected lipocalin variants P1E4, P3A12 and P3D11. (A) Amino acid sequence alignment of the selected lipocalin variants compared to wtLcn2. The central randomized gene cassette flanked by a pair of BstXI sites is underlined, β-stands and structurally hypervariable loops are labeled with letters A-H and numbers 1-4, respectively. (B) Coomassie-stained SDS-PAGE of the recombinant lipocalin variants after production in E. coli. The increased electrophoretic mobility under non-reducing conditions confirms formation of the single structural disulfide bridge in the Lcn2 scaffold. (C) Biomolecular interaction analysis between the immobilized hCD98hc ectodomain produced in E. coli (ARU=225) and the selected lipocalin variants P3A12 and P1E4 via SPR measurement. (D) Competitive binding analysis between the lipocalin variants P3D11 and P3A12 by SPR measurement. Binding sites on hCD98hcEDg were saturated with an injection of 100 nM P3D11 followed by injection of 100 nM P3A12, which did not cause an additive RU signal (black). Injection of 100 nM P3A12 without prior blocking of the hCD98hcED epitope with P3D11 evokes an expected binding signal for P3A12 (grey). Two consecutive buffer injections are shown as a negative control (light grey).

Figure 9:
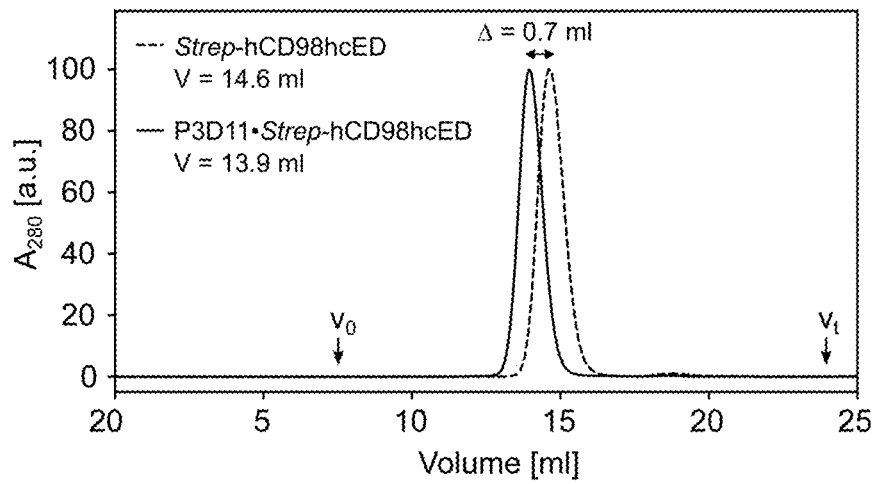
Figure 9:
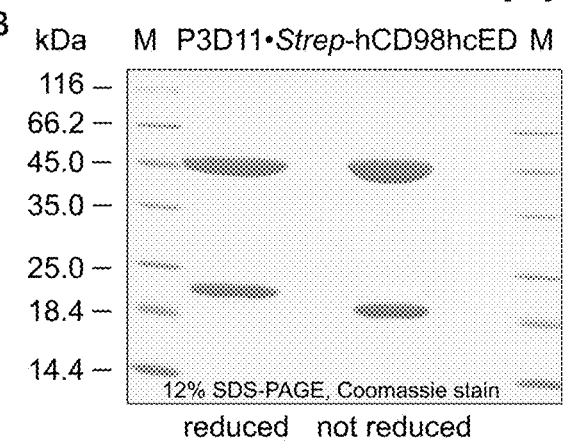
Figure 9:
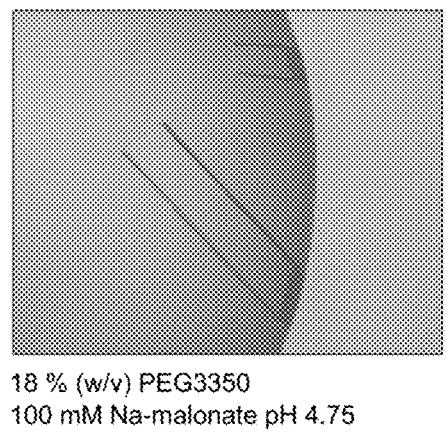
Figure 9:
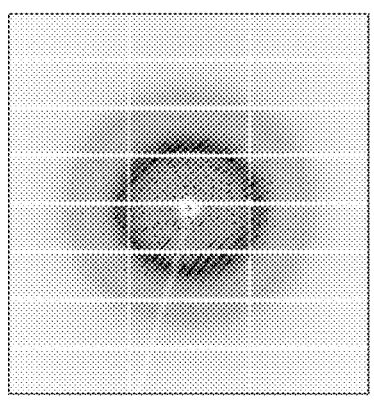

FIG. 9. Crystallization of the P3D11●hCD98hcED complex. (A) SEC purification of the P3D11●hCD98hcED complex. (B) Analytical SDS-PAGE of the purified P3D11●hCD98hcED complex with and without the addition of 2-mercaptoethanol. (C) Diffraction quality crystals obtained by vapor diffusion in hanging drops at 20° C. in 18% (w/v) PEG3350 and 100 mM Na-malonate pH 4.75. (D) Diffraction pattern obtained for the large crystal in (B).

Figure 10:
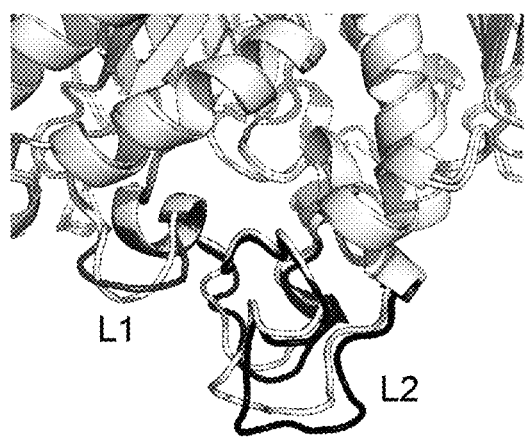
Figure 10:
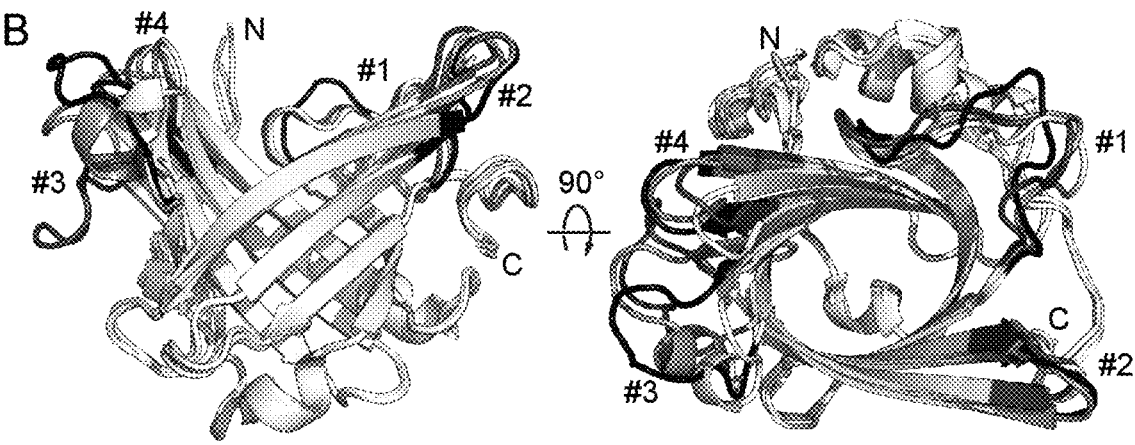

FIG. 10. Conformational differences of the individual complex components. (A) Conformational changes of hCD98hcED loop L1 (dark gray) and L2 (black) upon complex formation with P3D11. (B) Structural superposition of P3D11 with wild-type Lcn2 (PDB code 1L6M), Anticalin N7E (PDB code 5N47) and Anticalin PRS #003 (PDB code 3BX7), using the 58 conserved Cα positions that are conserved among different lipocalins. The structurally variable loops are highlighted for P3D11, wild-type Lcn2, N7E and PRS #003, respectively.

FIG. 11. Engineering of lipocalin variant P3D11 via error prone PCR and bacterial cell surface display. (A) Schematic depiction of surface displayed Lcn2 variants, which are presented by fusion to the engineered β-domain of autotransporter EspP. (B) Single clone FACS analysis after six selection cycles of BCSD in comparison to Lcn2 and the starting variant P3D11 using 1 nM biotinylated hCD98hcED. Additionally, mean intensity of PE fluorescence is shown for the unique lipocalin variants identified during stability and affinity engineering of P3D11. (C) Amino acid sequence alignment of the identified lipocalin variants compared to Lcn2 and the starting variant P3D11. The lipocalin variant D11vs was generated based on the sequence information provided by the selected variants. (D) Thermal stability testing of lipocalin variant P3D11 and its engineered version D11vs incubated at 37° C. for the indicated time points followed by SDS-PAGE analysis. (E) SPR real-time binding analysis of the stability and affinity improved variant D11vs for hCD98hcED. The deduced kinetic constants are listed in Table 1.

Figure 12:
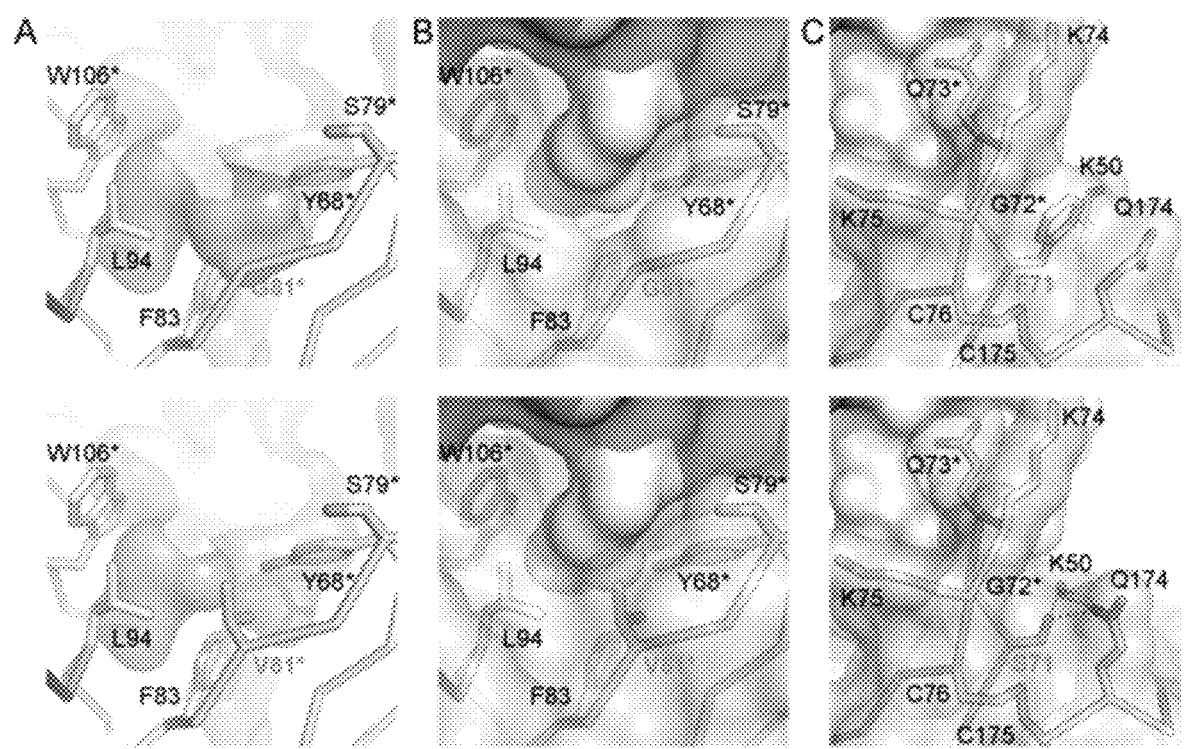

FIG. 12. Structural context of side chain substitutions that increase stability and/or affinity of P3D11. Residues that differ from wild-type Lcn2 are labeled with asterisks. (A) Hydrophobic cavity (surface illustration) lined by residues Tyr68, Gly81, Phe83 and Leu94 (upper panel). Substitution of Gly in position 81 of the Anticalin (translucent surface) with Val fills the cavity (lower panel). (B) In addition, Val81 increases the contact interface with hCD98hc (solid surface). (C) Substitution of Phe71 by Ser disrupts the aromatic stacking between Phe71 and Gln174, but permits hydrogen bond formation of Ser71 with Lys50 and Gln174.

Figure 13:
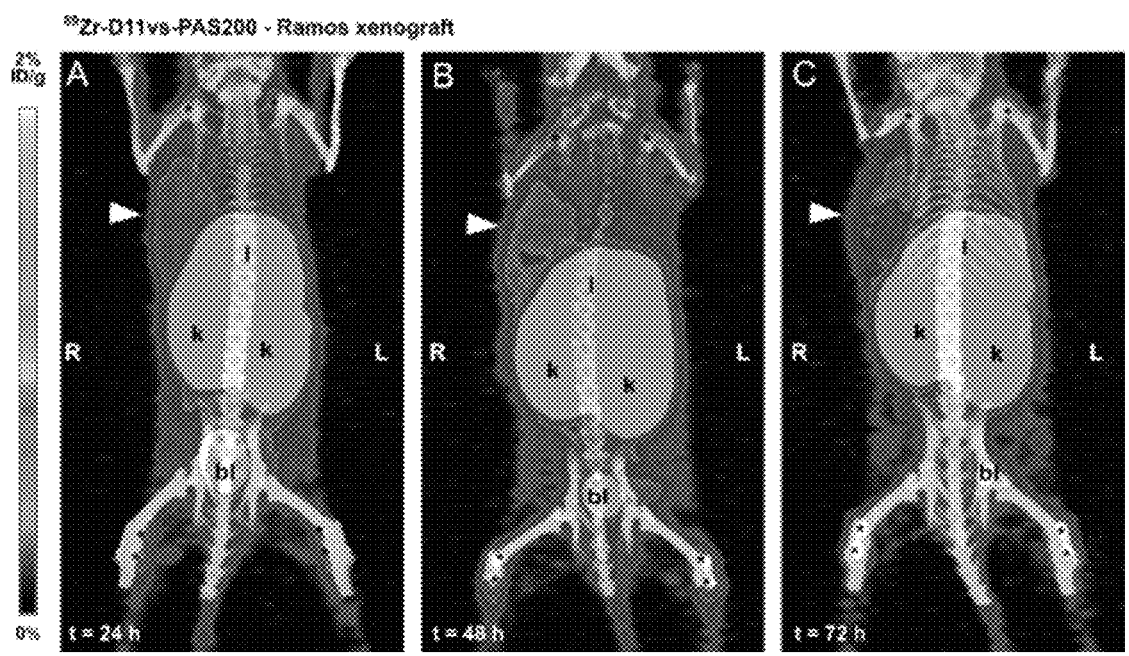

FIG. 13. In vivo $^{89}$Zr PET/CT imaging study in a B-cell Non-Hodgkin's lymphoma xenograft model. Mouse (♀) bearing Ramos xenograft was i.v. injected with 2.9 MBq $^{89}$Zr●D11vs-PAS200-DFO followed by PET/CT imaging 24, 48 and 72 h post injection. Signals were detected in the xenograft tumor (arrowheads), liver (l), kidneys (k), bladder (bl) and the joints (*).

Figure 14:
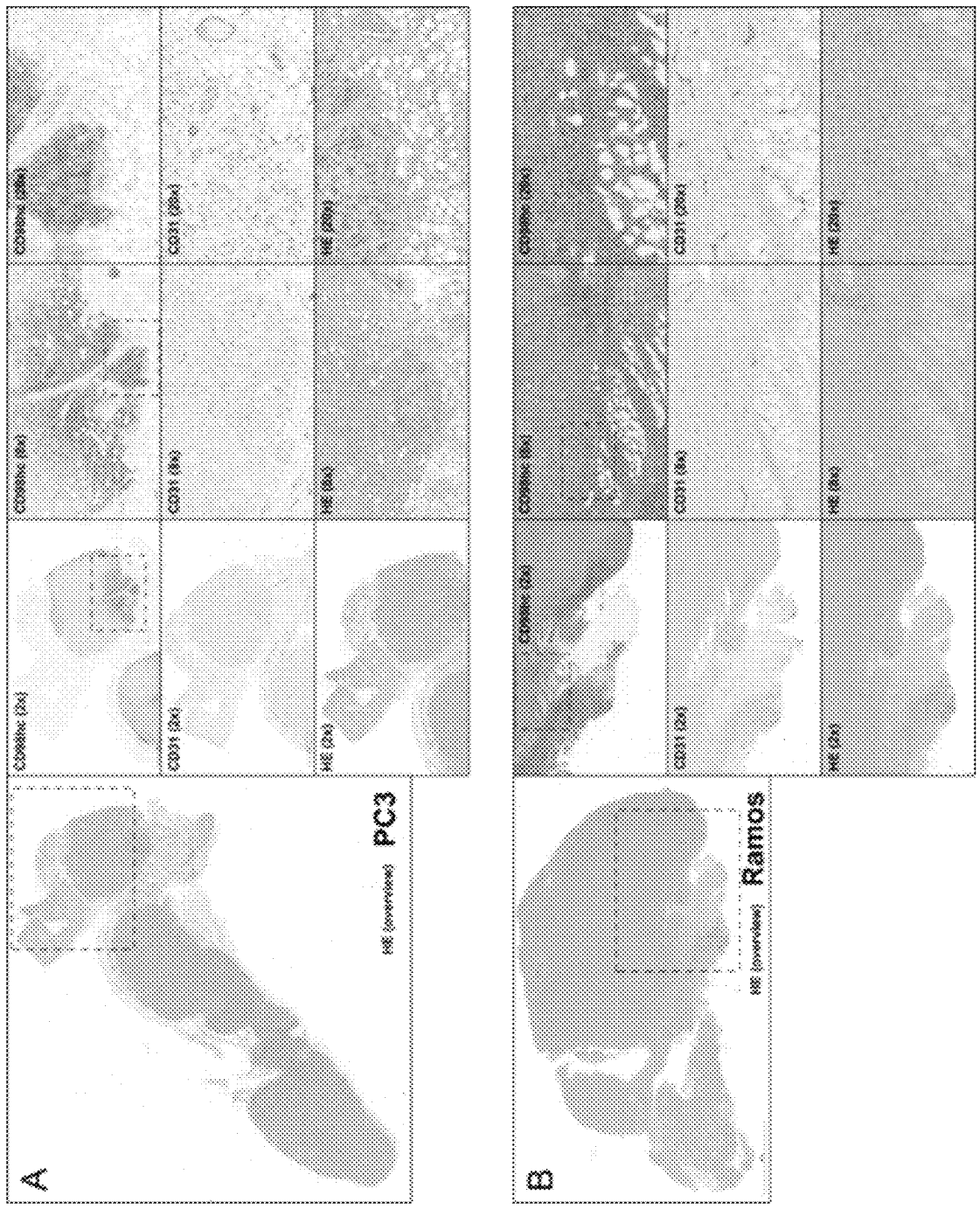

FIG. 14. Immunohistochemical characterization of PC-3 and Ramos tumor sections. Tissue sections of PC-3 (A) and Ramos (B) tumors stained with hematoxylin and eosin (H&E), CD31 (blood vessels) and CD98hc using appropriate antibodies. Order of magnification is indicated.

Figure 15:
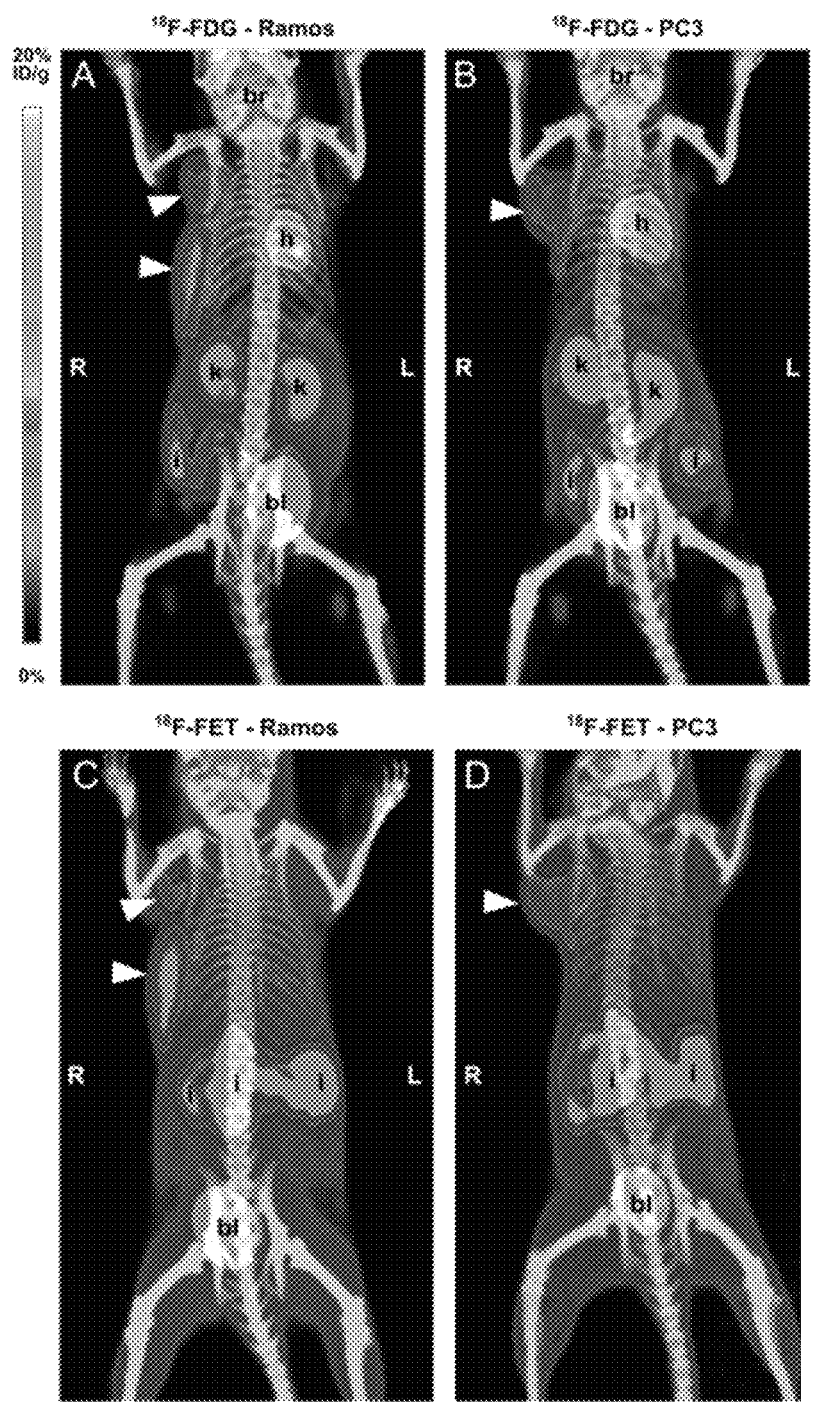

FIG. 15. $^{18}$F-fludeoxyglucose (FDG) and $^{18}$F-fluoroethyl-L-tyrosine (FET) PET/CT imaging. Mice (♀) bearing Ramos/PC-3 xenografts were i.v. injected with 12.3/12.7 MBq $^{18}$F-FDG (Panels A and B) or 11.8/12.1 MBq $^{18}$F-FET (Panels C and D) followed by PET/CT imaging 45 min post injection. Signals were detected in the xenograft tumor (arrowheads), brain (br), heart (h), liver (l), kidneys (k), intestine (i) and the bladder (bl).

FIG. 16. Contact area of P3D11 with CD98hc. (A) Residues of the lipocalin variant P3D11 that interact with hCD98hcED according to PISA analysis. Residues with contact area ≥Å$^2$ are highlighted in gray, whereas randomized positions are indicated with asterisks. (B) Summary of contact area and contact types of the lipocalin variant P3D11.

FIG. 17. Molecular design and characterization of PASylated D11vs. (A) Schematic depiction of Anticalin D11vs with a C-terminally attached PAS200 polypeptide, including an engineered Cys residue at the end. (B) Non-reducing SDS-PAGE of the PASylated D11vs variants used for in vitro and in vivo studies. For the D11vs-PAS200-Cy5.5 conjugate (rightmost lane), fluorescence was detected on a fluorescence scanner. (C and D) ESI-MS measurement (deconvoluted, raw data are shown as inset) for D11vs-PAS200-Cys after coupling to Sulfo-Cyanine5.5 (C) or Dfo (D) via maleimide chemistry, confirming a homogeneous site-specific labelling (Table 7).

TABLE 7

Protein mass determination of PASylated D11vs variants via ESI MS

| Protein | Theoretical mass [Da] | Measured mass [Da] | Mass difference to uncoupled [Da] |
|---|---|---|---|
| D11vs-PAS200 | 37933.5 | 37933.6 (Δ0.1) | — |
| D11vs-PAS200-Cys | 38036.7 | n.d. | — |

TABLE 7-continued

Protein mass determination of PASylated D11vs variants via ESI MS

| Protein | Theoretical mass [Da] | Measured mass [Da] | Mass difference to uncoupled [Da] |
|---|---|---|---|
| D11vs-PAS200-DFO | 38748.5 DFO: 711.8 | 39749.4 (Δ0.9) | 712.7 |
| D11vs-PAS200-Cy5.5 | 39060.9 S-Cy5.5: 1024.3 | 39062.1 (Δ1.2) | 1025.4 |

The examples illustrate the invention.

EXAMPLE 1—MATERIAL AND METHODS

Phage display selection, identification and production of hCD98hcED-specific lipocalin variants Selection of CD98hc-specific lipocalin variants was performed via filamentous phagemid display from a combinatorial library based on Lcn2 randomized at 20 positions within the structurally variable loops comprising $1 \times 10^{10}$ variants [50]. Biotinylated recombinant hCD98hcED (cf. Supplementary Information) was immobilized on streptavidin- or NeutrAvidin-coated paramagnetic beads (Sigma-Aldrich, Munich, Germany and Thermo Fisher Scientific, Waltham, Mass., respectively), incubated with the phagemid library (starting titer $1 \times 10^{12}$), and bound phagemids were eluted under denaturing conditions using 4 M urea. After five consecutive cycles, pooled phasmid DNA from the enriched library was prepared and subcloned on pNGAL98 in order to perform high-throughput ELISA screening from microcultures expressing the soluble lipocalin variants, as previously described [50]. Briefly, periplasmic extract was prepared and applied to 96-well MaxiSorp plates (Thermo Fisher Scientific) coated with 250 nM of hCD98hcED. After 1 h incubation bound lipocalin variants were detected by means of their C-terminal Strep-tag II using an ExtrAvidin/alkaline phosphatase (AP) conjugate (Sigma-Aldrich). Signals were developed using 0.5 mg/ml p-nitrophenyl phosphate in AP buffer (0.1 M NaCl, 5 mM MgCl2, 0.1 M Tris/HCl, pH 8.8) and absorbance measured at 405 nm with an Infinite 200 PRO microplate reader (Tecan, Mannerdorf, Switzerland). For clones showing significant binding towards hCD98hcED the expression cassette on the plasmid DNA was sequenced, and the soluble lipocalin variant was produced in a preparative scale as soluble, secretory protein in *E. coli* JM83 with a C-terminal His$_6$-tag using the plasmid pNGAL118 [50]. After periplasmic protein extraction the recombinant proteins were purified by immobilized metal ion affinity chromatography (IMAC) using a Ni(II)-charged HisTrap HP column (GE Healthcare, Munich, Germany) and subsequently subjected to size-exclusion chromatography (SEC) in PBS (4 mM KH$_2$PO$_4$, 160 mM Na$_2$HPO$_4$, 115 mM NaCl pH 7.4) on a 24 ml Superdex 75 10/300 GL column (GE Healthcare). Furthermore, plasmid construct design and production of recombinant D11vs-PAS200, D11vs-PAS200-Cys and Lcn2-PAS200-Cys was performed as previously described [51] and purified as described above.

Protein Crystallization and Structure Determination

For protein crystallization a variant of hCD98hcED with N-terminal Strep-tag II was produced in *E. coli* stain BL21 as described previously (Deuschle et al. submitted) (FIG. 12A). After incubation with the purified lipocalin variant P3D11 in a 1:1 molar ratio for 1 h at 4° C., the P3D11●hCD98hcED complex was isolated via SEC on a Superdex 200 10/300 GL column (GE Healthcare) and directly eluted in crystallization buffer comprising 10 mM Hepes/NaOH pH 7.5, 100 mM NaCl and 0.02% (w/v) NaN$_3$. The complex was concentrated to 15.7 mg/ml using a 30 kDa MWCO Amicon centrifugational filter (Merck Millipore, Burlington, Mass.) and subjected to crystallization by vapor diffusion in hanging drops at 20° C. Diffraction quality crystals were obtained by mixing 1 μl of the P3D11●hCD98hcED solution with 1 μl of reservoir solution containing 18% (w/v) PEG3350 and 100 mM Na-malonate pH 4.75. Suitable crystals were transferred into cryoprotectant consisting of 19% (w/v) PEG3350, 100 mM Na-malonate pH 5.0 and 20% (v/v) ethylene glycol prior to flash cooling in liquid nitrogen. X-ray diffraction data were collected at the Helmholtz-Zentrum Berlin, BESSY beamline 14.2 [52] and reduced with the XDS package [53] (Table 4).

TABLE 4

Data collection and refinement statistics

| Data collection | |
|---|---|
| Space group | C2 |
| Unit cell parameters | a = 202.81 Å, b = 46.05 Å, c = 137.09 Å, α = γ = 90°, β = 106.64° |
| Wavelength [Å] | 0.9184 |
| Resolution Å | 30.0 – 1.80 (1.90 – 1.80) |
| Completeness [%] | 99.8 (99.9) |
| Unique reflections | 113253 (16844) |
| Multiplicity | 6.8 (7.0) |
| Mean I/σ (I) | 23.9 (2.3) |
| R$_{meas}$ [%] | 4.9 (93.4) |
| Wilson B-factor [Å] | 37.4 |
| Refinement | |
| Resolution [Å] | 30.0 – 1.80 (1.85 – 1.80) |
| Reflections (working) | 111018 (8149) |
| Reflections (test)[b] | 2234 (187) |
| R$_{cryst}$ [%] | 18.4 (60.8) |
| R$_{free}$ [%] | 22.6 (67.0) |
| Protein molecules per au | 4 |
| Number of atoms: protein/solvent[c] | 9356/909 |
| B-values of atoms: protein/solvent [Å$^2$] | 33.3/39.2 |
| Ramachandran plot[d]: favored/outliers [%] | 96.8/0.2 |
| RMSD bonds [Å]/angles [°] | 0.02/1.76 |

[a]Values in parentheses refer to the highest resolution shell.
[b]Test set corresponds to 2% of all reflections
[c]Solvent refers to waters, ions as well as ordered buffer or cryoprotectant molecules
[d]Ramachandran statistics were calculated with MolProbity The crystal structure was solved by molecular replacement with Phaser [54] using coordinates of the hCD98hcED (PDB entry 2DH2) [55] and of the Anticalin N7A (PDB entry 4GH7) [50] as search models. Manual rebuilding and refinement were done with Coot [56] and Refmac5 [57], respectively (Table 4). Translation, libration and screw (TLS) groups were determined with TLSMD [58]. The asymmetric unit of space group C2 contained two P3D11●hCD98hcED complexes, of which the complex comprising chain pairs A and B, with overall lower B-factors, was used for analysis.

Biomolecular Interaction Analysis Via Surface Plasmon Resonance (SPR) Spectroscopy Real time surface plasmon resonance (SPR) spectroscopy was performed on a BIAcore 2000 system (BIAcore, Uppsala, Sweden) at 25° C. using HBS-T (20 mM Hepes/NaOH pH 7.5, 150 mM NaCl, 0.005% v/v Tween20) as running buffer. The purified biotinylated m/hCD98hcED (3 μg/ml protein solution in HBS-T produced in HEK cells or *E. coli*)

was immobilized (ARU-225) via streptavidin on a CAP sensorchip of the Biotin CAPture kit (GE Healthcare). SPR single cycle kinetic experiments were performed using five consecutive injections of a 1:2 dilution series of the purified lipocalin variant at a flow rate of 25 μl/min, with 288 s contact time and 3500 s dissociation time after the fifth injection. For multi cycle kinetic experiments, eight samples from a consecutive 1:2 dilution series of the purified lipocalin variant were measured. Rate constants of association and dissociation were calculated from reference-corrected sensorgrams by fitting to a global 1:1 Langmuir binding model using BIAevaluation software (BIAcore). The equilibrium dissociation constants ($K_D$ value) were calculated as the quotient $k_{off}/k_{on}$. To test competitive binding of the lipocalin variants P3D11, P3A12 and P1E4 to glycosylated hCD98hcED, 100 nM of P3D11 was first injected and followed by a subsequent injection of either 100 nM P3A12 or 100 nM P1E4. HBS-T injections served as negative control.

Error-Prone Library Construction and Bacterial Cell Surface Display Selection

Stability and affinity engineering of the lipocalin variant P3D11 was accomplished by means of directed evolution and bacterial surface display (BSD) as previously published [51, 59, 60]. Briefly, error-prone PCR was executed using the GeneMorph II random mutagenesis kit (Agilent, Santa Clara, Calif.) with 10 μg of the central coding region for the lipocalin variant P3D11 used as template. After digest of the PCR product with BstXI, the randomized DNA fragment was ligated with the backbone of pNGAL146 and used for electrotransformation of *E. coli* JK321, yielding $5\times10^9$ transformants plated on LB agar medium supplemented with 100 μg/ml ampicillin. The bacterial lawn was scraped from the plate(s), resuspended in 50 ml LB/Amp medium, followed by inoculation to an initial $OD_{550}$ of 0.15 at 37° C. Gene expression was induced at $OD_{550}$=0.5 with 10 ng/ml anhydrotetracycline (aTc) for 2.5 h. Approximately $2\times10^8$ cells were sedimented and resuspended in PBS with biotinylated hCD98hcED at different concentrations (cycles 1 and 2: 100 nM; cycles 3 and 4: 10 nM; cycles 5 and 6: 1 nM) for 1 h at 4° C. After one washing step with PBS, the bacteria were incubated with 25 μg/ml streptavidin/phycoerythrin (PE) conjugate (Biolegend, San Diego, Calif.) and 3 μM dye-labeled Fab A3C5-DY634 [61] in PBS for 30 min followed by a last washing step in PBS. Bacteria were sorted on a FACSAria IIu instrument (BD Bioscience, Heidelberg, Germany) using a 488 nm LASER diode with a 585/42 band pass filter or a 633 nm HeNe LASER in combination with a 660/20 band pass filter for excitation/detection of PE and DY634 fluorescence, respectively. Sorted bacteria were plated on LB/Amp agar, incubated at 37° C. for 12 h and then subjected to a new sorting cycle. After BSD cycle 6, single clone analysis was performed by cytofluorimetric analysis of individual colonies. Data were processed using FlowJo v10 software (FlowJo, Ashland, Oreg.).

Flow Cytofluorimetry

The human cancer cell lines Ramos, Raji, SU-DHL-4, PC3 and DU-145 were cultivated in Roswell Park Memorial Institute (RPMI) 1640 medium containing 2.0 g/L $NaHCO_3$ and stable L-glutamine (Biochrom, Berlin, Germany), supplemented with 10% (v/v) fetal bovine serum (FBS) (PAA Laboratories, Pasching, Austria) at 37° C. under humidified 5% $CO_2$ atmosphere. Adherent cells (PC3, DU-145 and Caco-2) were washed with PBS (w/o $Ca^{2+}$ and $Mg^{2+}$) (Biochrom) and detached using PBS (w/o $Ca^{2+}$ and $Mg^{2+}$) supplemented with 0.5 mM EDTA for 10 min at 37° C. Cells growing in suspension (Ramos, Raji and SU-DHL-4) were directly washed with PBS (w/o $Ca^{2+}$ and $Mg^{2+}$). For each measurement, 250,000 viable cells were resuspended in 250 μl FACS buffer (PBS+10% (v/v) FBS) containing 1 μM D11vs-PAS200-Cy5.5 (cf. Supplementary information) and incubated for 1 h at 4° C. Competition experiments were performed by adding a 10-fold molar concentration of either unlabeled D11vs-PAS200 or the soluble glycosylated hCD98hcED. After incubation, cells were washed three times in PBS and finally resuspended in 250 μl FACS buffer. Flow cytofluorometric experiments were performed on a FACSAria IIu instrument using an excitation wavelength of 650 nm and an emission band-path filter of 780/60 nm.

Immunofluorescence Microscopy of CD98hc Expressing Cells

PC-3 and Caco-2 cells were cultivated at 37° C. on poly-D-lysine (PDL) coated Lab-Tek II chamber slides (Thermo Fisher Scientific, Waltham, Mass.) in RPMI 1640 medium containing 2.0 g/L $NaHCO_3$ and stable L-glutamine, supplemented with 10 (v/v) % FBS, until 60-70 confluence was reached. After three times washing with PBS, the cells were incubated with 1 μM D11vs-PAS200-Cy5.5 for 1 h at 37° C., followed by another three washing steps. Ramos cells, on the other hand, were grown in suspension and stained in the same manner using a reaction tube, followed by transfer to a PDL coated Lab-Tek II chamber slide. For control experiments, the D11vs-PAS200-Cy5.5 conjugate was premixed with a 10-fold molar concentration of unlabeled D11vs-PAS200 or the equivalent conjugate of wtLcn2 (Lcn2-PAS200-Cy5.5) was applied. Cells were fixed and counterstained by 5 min incubation with ice-cold methanol containing 1 μg/ml 4',6-diamidino-2-phenylindole (DAPI; Sigma-Aldrich). Digital fluorescence images were recorded on an Axiovert 40 CFL microscope equipped with an AxioCam MRm camera (Carl Zeiss Microscopy, Jena, Germany) using 365/12 nm (DAPI) and 716/40 nm (Cy5.5) band-pass filters with identical exposure times.

Circular Dichroism (CD) Spectroscopy and Thermal Denaturation

CD spectra and thermal unfolding of purified Lcn2 variants were recorded using a Jasco J-810 spectropolarimeter (Jasco, Pfungstadt, Germany) controlled by Spectra manager software (ver. 1.53.05) equipped with a PT-423S Peltier element. Proteins were dialyzed against 20 mM $KP_i$ pH 7.5 and 50 mM $K_2SO_4$ and applied at a concentration of 1 μM. In order to identify the wavelength with maximum change in CD signal for thermal denaturation studies, spectra were measured in a 1 mm path length quartz cuvette (Hellma, Müllheim, Germany) from 190-250 nM at 20° C. and 90° C. Thermal unfolding of the lipocalin variants was measured at a wavelength of 214 nm by heating from 20° C. to 90° C. at a rate of 60° C./h. Data were fitted to an equation for a one-step unfolding transition, and the melting temperature ($T_m$), enthalpy of unfolding ($\Delta H_m$) and Gibb's free energy of unfolding ($\Delta G^0$) at ambient temperature was calculated as previously described [62].

In Vivo Xenograft Studies

Animal experiments were conducted with permission from the District Government of Upper Bavaria (application no.: 55.2-1-54-2532-216-15). CB17-SCID mice at an age of 6 weeks (♂) and (♀) were purchased from Charles River Laboratories (Wilmington, Mass.) and housed under specific pathogen free (SPF) conditions. Mice were injected subcutaneously with 100 μl RPMI 1640 medium (without supplements) containing $6\times10^6$ PC-3 cells above the right shoulder. On day 12 p.i. the tumor had reached a diameter of ~0.5 cm and the mice were used for in vivo studies.

$^{89}$Zr Positron Emission Tomography

For $^{89}$Zr-labeling of Dfo-conjugated [63] D11vs-PAS200 (for protein production and coupling cf. Supplementary information), 250 μg of the protein dialyzed against 250 mM Na-acetate pH 5.5 was incubated with 200 μl 0.5 M Hepes/NaOH pH 7.0, 50 μl 0.5 M gentistic acid and 111 MBq $^{89}$Zr in 1 M oxalic acid (neutralized with 3 M Na$_2$CO$_3$) (Perkin Elmer, Waltham, Mass.). After 1 h incubation at 37° C., radiolabeling was confirmed by radio thin layer chromatography (radio-TLC) on strips using Na-citrate pH 5.0 as mobile phase. The radio-labeled protein tracer was separated by gel filtration using a PD-10 column (GE Healthcare) equilibrated with 0.9% NaCl solution (B. Braun, Melsungen, Germany). Radiochemical purity of the protein tracer was confirmed by radio-TLC prior to its use for injections.

For the biodistribution study, mice were injected with the protein tracer via the tail vein at a dose of 3.96±0.12 MBq. For blocking experiments, a 100-fold (FIG. 5) or 250-fold (FIG. 6) molar amount of D11vs-PAS200 was injected 2 h prior to the tracer injection. Static PET/CT imaging was performed at indicated time points under isoflurane anesthesia in an Inveon PET/CT small-animal scanner (Siemens Medical Solutions, Erlangen, Germany) with 20 min PET and 5 min CT acquisition. Data were analyzed with the Inveon Research Workplace software (Siemens Medical Solutions, Erlangen, Germany) and reconstructed using the 0.8 mm high resolution OSEM-3D algorithm. Quantification of regions of interest (ROI) was performed by threshold-based image segmentation with a lower threshold at 50% of the hottest voxel for in vivo PET and a threshold of 10 kBq/ml for ex vivo PET images.

Biodistribution Analysis and Autoradiography

Tumor, blood and organs were dissected from the sacrificed animals at the end of the experiment in order to determine weight and quantify radioactivity using a 2480 Wizard$^2$ automatic gamma counter (PerkinElmer). A 1% fraction of the injected protein tracer dose was used as reference. Uptake values were calculated as % ID/g and corrected for radioactive decay from the time point of injection.

After radioactivity measurement, the tumor was transversally bisected and used for immunohistochemistry and autoradiography analysis. For autoradiography the tumor was embedded in Tissue-Tek O.C.T. (Sakura Finetek, Alphen aan den Rijn, The Netherlands) in an embedding mold and frozen. Subsequently, 10 μm sections were prepared using a CM1950 cryostat (Leica Biosystems, Nußloch, Germany) and the sections were mounted on a superfrost microscopic slide (Thermo Fisher Scientific). The slide was exposed, together with a standard dilution row in silicon isolators (Grace Bio-Labs, Bend, Oreg.), to a storage phosphor screen BAS-IP super resolution film (GE Healthcare) for one week, followed by quantification using a CR 25 BIO autoradiography scanner (Durr Medical, Bietigheim-Bissingen, Germany) and data analysis with AIDA software ver. 4.24.036 (Raytest, Straubenhardt, Germany). Chosen pictures show the sections with the highest exposure level to allow comparison of blocked and unblocked tumor sections.

Immunohistochemistry

Tumor tissue was fixed for 48 h in 4% paraformaldehyde in PBS and stored in PBS at 4° C. until radioactivity decayed. Tissue was dehydrated under standard conditions (ASP300S; Leica Biosystems) and embedded in paraffin. Serial 2-μm-thin sections prepared with a rotary microtome (HM355S; Thermo Fisher Scientific) were collected and subjected to histological and immunohistochemical analysis. Hematoxylin-eosin staining was performed on deparaffinized sections.

Immunohistochemistry was done under standard conditions using appropriate antibodies (AT-2; Leica Biosystems). Representative images were collected using Aperio Imagescope software (version 12.3; Leica Biosystems).

Statistics

For mean comparison between two groups of animals, the Student's t test for unpaired data was used. P values 0.05 were considered statistically significant (* P≤0.05; ** P≤0.005). Experimental data were analyzed using Prism 6 (GraphPad Software, San Diego, Calif.) and standard deviations (S.D.) are indicated.

Soluble Production and Purification of the Monobiotinylated Human and Murine CD98hc Ectodomains The human and murine CD98hcED (UniProt ID P10852-1, residues Glu105-Ala526 and UniProt ID P08195-2, residues Glu111-Ala529, respectively) were produced in E. coli strain BL21 using pASK-IBA5(+)-BAP-m/hCD98hcED and in human embryonic kidney (HEK) 293E cells (MEXi expression system, IBA Lifesciences, Goettingen, Germany) using the expression plasmid pDSG-BM-His$_6$-BAP-m/hCD98hcEDg-Igk-BirA-StrepDEL (StrepDEL=Fusion of the Strep-tag II amino acid sequence WSHPQFEK and the endoplasmic reticulum retention signal sequence KDEL).

For expression in E. coli, BL21 was co-transformed with pBirAcm encoding biotin ligase (Avidity LLC, Aurora, Colo.), and heterologous gene expression was induced with 0.5 mg/L anhydrotetracycline (aTc) and 1 mM isopropyl-f3-D-thiogalactopyranoside (IPTG) for 12 h at 26° C. in 2 L 2xYT medium. Cells were harvested by centrifugation, resuspended in anion-exchange chromatography (AEX) buffer (20 mM Tris/HCl pH 8.0, 1 mM EDTA) and disrupted with a PandaPLUS 2000 homogenizer (GEA Niro Soavi, Parma, Italy). The recombinant ectodomain was purified from the whole cell extract by AEX using a MacroCap Q column (GE Healthcare, Munich, Germany) equilibrated with AEX buffer using a linear concentration gradient of 0-500 mM NaCl. Appropriate fractions were pooled, dialyzed against 100 mM Tris/HCl pH 8.0, 50 mM NaCl, 1 mM EDTA, and applied to a 5 ml column carrying a streptavidin mutant which allows binding of biotinylated proteins and competitive elution via an excess of free biotin (unpublished). After elution using 5 mM biotin in the same buffer, preparative size-exclusion chromatography (SEC) was performed on a 24 ml Superdex 200 10/300 GL column (GE Healthcare) using PBS (4 mM KH$_2$PO$_4$, 16 mM Na$_2$HPO$_4$, 115 mM NaCl, pH 7.4) as a running buffer.

Expression procedure of the m/hCD98hcEDg in MEXi cells was essentially performed as recommended by the manufacturer. Briefly, cells were cultivated in MEXi culture medium supplemented with 50 mg/l G-418 and 8 mM L-alanyl-L-glutamine at 37° C. under humidified 5% CO$_2$ atmosphere. 250 ml containing 5×10$^6$ cells/mi were transfected using 5 μg plasmid DNA/1×10$^6$ cells, and mixed at a 1:3 mass ratio with polyethylenimine in MEXi transfection medium. After 4 h incubation at 37° C., 500 ml of MEXi cultivation medium was added, and secretory expression was continued for 4 days. After sedimentation of the HEK cells by centrifugation, the supernatant was dialyzed against an immobilized metal ion affinity chromatography (IMAC) buffer (20 mM Tris/HCl pH 8.0, 500 mM NaCl), and IMAC was performed on a Ni(II)-charged HisTrap HP column (GE Healthcare). Elution fractions obtained after applying a linear concentration gradient of 0-300 mM imidazole/HCl in IMAC buffer were pooled and further purified via streptavidin affinity chromatography and preparative SEC as described above.

Analytical SEC and SDS-PAGE

Analytical SEC was performed using a 24 ml Superdex 200 10/300 GL column (GE Healthcare) in PBS pH 7.4 at a flow rate of 0.5 ml/min. For apparent molecular weight determination, the column was calibrated with the following standard proteins (Sigma-Aldrich, Munich, Germany): thyroglobulin (669 kDa), alcohol dehydrogenase (150 kDa), bovine serum albumin (66 kDa), carbonic anhydrase (29 kDa), cytochrome c (12.4 kDa) and aprotinin (6.5 kDa). The void volume of the column was determined using Blue dextran (Sigma-Aldrich). Based on the elution volumes, the partition coefficients $K_{av}$ were calculated and used to interpolate the apparent molecular sizes of the analyzed proteins.

SDS-PAGE was performed using a high molarity Tris buffer system with or without the addition of 2-mercaptoethanol in the sample buffer, followed by staining with Coomassie brilliant blue or direct detection of Cy5.5 fluorescence (for corresponding protein conjugates) using an Ettan DIGE fluorescence scanner (GE Healthcare) with an excitation wavelength of 635/30 nm and a 680/30 nm emission band-path filter Enzymatic Cleavage of N-Linked Sugars from m/hCD98hcEDg Using PNGase F N-linked glycans were enzymatically removed from m/hCD98hcEDg produced in HEK cells using Peptide-N-Glycosidase F (PNGase F) (New England Biolabs, Ipswich, Mass.). 5 µg protein were first denatured by adding 0.5% sodium dodecyl sulfate (SDS) and 40 mM dithiothreitol (DTT) for 10 min at 100° C. Subsequently, 50 mM $Na_3PO_4$ pH 7.5, 1% (v/v) NP-40 and 250 units of PNGase F were added, incubated for 1 h at 37° C. and subjected to SDS-PAGE for comparison with the untreated ectodomain (Fig. S7D).

Site-Specific Thiol Labelling of PASylated Lipocalin Variants Via Maleimide Chemistry For site-specific labelling at the engineered C-terminal Cys side chain (FIG. 17), maleimide-functionalized deferoxamine (Dfo; Macrocyclics, Plano, Tex.) or Sulfo-Cyanine5.5 (Cy5.5, Lumiprobe, Hannover, Germany) was used. To ensure presence of the free thiol for homogeneous C-terminal labelling without cleaving the intramolecular disulfide bridge of the lipocalin variant, the purified protein was incubated with a 20-fold molar concentration of DTT for 1 h at 20° C. in PBS pH 7.4. Then, the buffer was exchanged against 50 mM $NaH_2PO_4$ pH 5.5, 100 mM NaCl, 1 mM EDTA by gel filtration on a PD-10 column (GE Healthcare). After adjusting the pH to 7.4 using an appropriate volume of $Na_3PO_4$ and quantification of the protein concentration, a 5-fold molar concentration of the respective coupling reagent was added and incubated for 12 h at 4° C. Residual reagents were removed using a 24 ml Superdex 200 10/300 GL column equilibrated in PBS (pH 7.4). Successful 1:1 coupling with Dfo or Cy5.5 was verified using ESI-MS and the target affinity of each conjugate was verified.

ESI Mass Spectrometry

Mass spectra of proteins were measured on a maXis mass spectrometer with an electrospray ionization (ESI) source (Bruker Daltonics, Bremen, Germany) in the positive ion mode. To measure the intact protein mass (under denaturing conditions), the purified protein was dialyzed against 10 mM ammonium acetate pH 6.6 followed by the addition of 50% (v/v) methanol and 0.1% (v/v) acetic acid and application to the mass spectrometer via a syringe pump operated at 180 µL/h. The following conditions for the ion-transfer were used: 3400 V capillary voltage, 500 V endplate offset, 4 L/min dry gas at 200° C. temperature, 0.3 bar nebulizer pressure and 3 eV collision energy. Raw spectra were collected and deconvoluted with the Bruker Compass Data Analysis Software using the MaxEnt algorithm.

EXAMPLE 2—RESULTS

Phage Display Selection Divulged a hCD98hcED-Specific Lcn2 Variant with Pico-Molar Affinity The soluble, monomeric extracellular domain of human CD98hc (UniProt ID P08195-2, residues Glu105-Ala526) was produced fully glycosylated in eukaryotic human embryonic kidney (HEK) cells (CD98hcEDg) and unglycosylated in E. coli (CD98hcED) (FIG. 7). The four occupied N-glycosylation sites of CD98hcEDg (Asn264, 280, 323 and 405) account for 32.4 of its apparent mass as determined by analytical SEC and reduce its electrophoretic mobility (FIG. 7 and Table 2).

TABLE 2

Size determination of the glycosylated and unglycosylated m/hCD98hcED

| Protein | Theoretical mass [kDa] | Apparent mass (SEC)[kDa] | Apparent mass increase [%][a] |
|---|---|---|---|
| hCD98hcED | 48.4 | 49.4 | — |
| mCD98hcED | 49.3 | 51.6 | — |
| hCD98hcEDg | 49.3 | 73.1 | 32.4 |
| mCD98hcEDg | 50.2 | 79.8 | 37.1 |

[a]Apparent mass increase caused by the N-linked glycosylation of h/mCD98hcED after production in HEK cells compared to production in E. coli This extensive glycosylation of hCD98hcED could impede in vitro phage display selection of cognate Anticalins due to poor sterical accessibility of potential surface epitopes, as previously seen in the selection of Anticalins against the prostate-specific membrane antigen [65]. To avoid the necessity of glycan removal, which either requires harsh reaction conditions or results in incomplete deglycosylation, here the unglycosylated ectodomain produced in E. coli was used as the initial molecular target for selection. N-terminal fusion of the biotin acceptor peptide (BAP) resulted in the intracellular enzymatic attachment of a single biotin group upon co-expression of the BirA ligase (verified via western blot analysis, data not shown) for both CD98hcEDg and CD98hcED, regardless of the expression system used [66]. This modification allowed immobilization of the ectodomain to beads or surfaces in an orientation that resembles the in vivo situation for the type II membrane protein, accessible for binding of lipocalin variants during phage display selection, ELISA screening and in vitro binding studies.

Anticalin candidates were selected from a Lcn2 random library with a combinatorial complexity of $1 \times 10^{10}$, which also had served for the development of other hapten- and protein-specific Anticalins in the past [50]. After six selection cycles, three independent CD98hc-specific lipocalin variants were identified by ELISA screening, then expressed as soluble proteins in E. coli at the shake flask scale and purified to homogeneity, resulting in monomeric proteins with apparent molecular size similar to wild type (wt) Lcn2 (FIG. 1B, FIGS. 8A and B). To determine the rate constants of association and dissociation of the selected Anticalin candidates, SPR real-time analyses were performed using both the glycosylated and unglycosylated immobilized CD98hcED. The three lipocalin variants showed equilibrium dissociation constants in the single-digit to sub-nanomolar range (Table 1, FIG. 1C and FIG. 8C).

TABLE 1

Affinities for hCD98hcED and thermal stabilities of engineered lipocalin variants

| Protein | Affinity | | | | Stability | | |
|---|---|---|---|---|---|---|---|
| | $K_D$ [nM] | $k_{on}$ [M$^{-1}$ × s$^{-1}$] | $k_{off}$ [s$^{-1}$] | T½ [min] | $T_m$ [° C.] | $\Delta H_m$ [kJ/mol] | $\Delta G_U$ [kJ/mol] |
| P1E4 | 4.5$^a$ | 2.5 × 10$^6$ | 1.1 × 10$^{-2}$ | 1.1 | 68.8 | 812 | 104.0 |
| P3A12 | 2.8$^b$ | 6.2 × 10$^4$ | 1.7 × 10$^{-4}$ | 67.7 | 64.1 | 635 | 73.6 |
| P3D11 | 0.15$^b$ | 2.2 × 10$^5$ | 3.2 × 10$^{-5}$ | 359.4 | 55.2 | 368 | 33.8 |
| D11vs | 0.05$^b$ | 4.5 × 10$^5$ | 2.6 × 10$^{-5}$ | 442.3 | 63.5 | 646 | 73.9 |

$^a$= multiple cycle kinetics
$^b$= single cycle kinetics

Notably, the lipocalin variant P3D11 revealed a very low $K_D$ value of 150 pM for hCD98hcED and a long complex half-life of 6 h, hence suitable for tumor targeting in vivo (FIG. 1C). Interestingly, a series of competitive SPR experiments indicated that all three Anticalins recognize overlapping epitopes on hCD98hcED (FIG. 8D, example shown for the variants P3D11 and P3A12), despite considerable sequence deviation in particular between variants P1E4 and P3D11 (cf. FIG. 8A).

Protruding Loops Constitute the Major Epitope for hCD98hcED Recognition by the Engineered Lipocalin To identify the epitope region targeted by these Anticalin candidates and to understand the structural mechanisms of the tight molecular interaction of P3D11 with the ectodomain, we crystallized P3D11 in complex with hCD98hcED (carrying a N-terminal Strep-tag II) after isolation of the 1:1 complex via SEC (FIG. 9). The hCD98hcED●P3D11 complex crystallized in space group C2 with two complexes per asymmetric unit, and its X-ray structure was refined to a resolution of 1.8 Å (Table 4). hCD98hcED resembles a glycoside hydrolase fold, comprising a central $(\alpha/\beta)_8$-TIM barrel core domain (residues 114-438) and a C-terminal β-sandwich domain (residues 439-529), as previously described [55]. Both N- and C-termini point toward the cytoplasmic membrane, hence mainly the C-terminal membrane distal side of the TIM barrel domain is accessible to bind molecules. Indeed, the engineered lipocalin binds the membrane-distal part of hCD98hcED with its four variable loops #1-#4 protruding from the β-barrel (FIG. 2). The β-barrel axis of P3D11 is tilted by ~45° with regard to the TIM barrel axis of hCD98hcED. The contact interface between both molecules involves a total buried surface area (BSA) of 1473 Å$^2$ (1424 Å$^2$ on the side of the lipocalin and 1521 Å$^2$ on the one of the membrane protein), 15 hydrogen bonds and 3 salt bridges (Table 5), resulting in the largest interface observed for Anticalin●protein complexes thus far [67].

TABLE 5

Summary of the contact area and contacts provided by the lipocalin variant P3D11

| | BSA [Å$^2$] | BSA mutated [Å$^2$] | HB/SB |
|---|---|---|---|
| Loop #1 | 486 | 156 | 5/2 |
| Loop #2 | 175 | 169 | 2/— |
| Loop #3 | 90 | 1.0 | 1/— |
| Loop #4 | 97 | 77 | 1/— |
| β-barrel | 576 | 364 | 6/1 |
| SUM | 1424 | 767 | 15/3 |

In part the interaction is driven by electrostatics as P3D11 is positively charged, favoring interaction with the predominantly negatively charged epitope on hCD98hcED, which is reflected by the calculated pI values of 8.8 and 5.2 for P3D11 and hCD98hcED, respectively. The epitope of hCD98hcED essentially consists of two loops, L1 (residues 128-137) and L2 (374-404), which follow to the first and the eighth β-strand of the TIM barrel, respectively.

Almost 75% of the contact interface is contributed by the interaction with L2, which penetrates deep into the β-barrel of the engineered lipocalin, whereas L1 provides approximately 20% of the total BSA (Table 6)

TABLE 6

Summary of the contact area and contacts provided by hCD98hcED

| | BSA [Å$^2$] | HB/SB |
|---|---|---|
| hCD98hcED | 1521 | 15/3 |
| Loop L1 | 288 | 6/1 |
| Loop L2 | 1111 | 6/1 |

Further to the direct protein●protein contacts, 16 water molecules mediate hydrogen bonds at the complex interface. Based on the distribution of hydrogen bond donors, acceptors as well as water molecules, the P3D11 interface with the hCD98hcED can be dissected into two distinct areas, a rather polar region around the lipocalin loops #1 and #2 including the cavity as well as a rather apolar region around loop #3 and #4 (FIG. 2B).

Interestingly, binding of P3D11 causes an induced fit of hCD98hcED. Superposition of the hCD98hcED Cα positions in complex with P3D11 and for hCD98hcED crystallized alone (PDB entry 2DH2) [55], excluding the epitope loops L1 and L2, revealed an RMSD value of 0.97 Å (for 375 equivalent Cα positions), while in this context loops 1 and 2 deviate by 1.6 and 1.8 Å, respectively (FIG. 10A). Likewise, P3D11 shows conformational differences among its loops #1-4 compared with wtLcn2 (PDB code 1L6M); yet, these may be caused by the sequence changes (FIG. 10B).

Although the selection of P3D11 was performed with the unglycosylated hCD98hcED, its affinity for the glycosylated hCD98hcEDg was indistinguishable (Table 3).

TABLE 3

Affinities of selected and engineered lipocalin variants for hCD98hcEDg determined via SPR analysis

| Protein | $K_D$ [nM] | $k_{on}$ M$^{-1}$ × s$^{-1}$ | $k_{off}$ [s$^{-1}$] | $T_{1/2}$ [min] |
|---|---|---|---|---|
| P1E4 | 162 | 5.6 × 10$^5$ | 9.0 × 10$^{-2}$ | <1 |
| P3A12 | 1.9 | 2.2 × 10$^4$ | 4.0 × 10$^{-4}$ | 29 |
| P3D11 | 0.17 | 3.0 × 10$^5$ | 5.0 × 10$^{-5}$ | 230 |
| D11vs | 0.05 | 4.6 × 10$^5$ | 2.2 × 10$^{-5}$ | 523 |

Modeling of the glycan moieties suggests that the Anticalin binds the protruding epitope in close proximity to two of the oligosaccharides but is not sterically hindered by them (FIG. 2C). Interestingly, P3D11 does not show any affinity for the murine antigen (mCD98hcED, data not shown), which can be explained by significant differences both in the amino acid sequences and in the glycosylation pattern between the CD98hc orthologs. In particular, loop L2 of mCD98hcED is shorter by one residue, carries a N-glycosylation site and shows considerable sequence changes (Deuschle et al. submitted). Notably, this observation is in line with the known properties of the clinical-stage mAb IGN523, which also recognizes loop L2 (residues 374-401) of hCD98hcED with picomolar affinity but shows no detectable affinity for mCD98hc [20, 68].

Directed Evolution Results in an Anticalin with Improved Affinity and Stability

Despite its tight binding activity towards hCD98hcED, the lipocalin variant P3D11 suffered from low thermal stability, a caveat for further preclinical as well as clinical development (Table 1). To tackle this issue, stability engineering was performed via directed evolution using bacterial surface display (BSD) starting from an error-prone library with moderate amino acid mutation rate (with approximately two amino acid exchanges on average) (FIG. 11A).

To select variants of P3D11 with enhanced thermal stability, expression of the membrane-anchored protein was induced at 37° C. and only bacteria showing both strong hCD98hcED binding and high cell surface display level were gated in the FACS experiment (FIG. 3A). After six enrichment cycles, the lipocalin library exhibited a strong average binding signal after incubation with 1 nM hCD98hcED, whereas almost no binding was detectable for the initial clone P3D11 if tested under the same conditions. Single clone analysis with 1 nM hCD98hcED verified strong binding of several of the new P3D11 variants (D11.1 shown as an example, FIG. 3B and FIG. 11B) whereas just very modest binding was detected for P3D11, and no signal for wtLcn2 as expected. Considering that P3D11 exhibits a $K_D$ value of 150 pM for hCD98hcED the increased binding signal is likely caused by the more efficient bacterial surface display of lipocalin variants with improved protein folding and/or stability. Subsequent sequence analysis revealed that replacement of Gly81 and Phe71 by Val and Ser, respectively, in the P3D11 sequence appear to be crucial in this regard (FIG. 11C). Therefore, the P3D11 variant D11vs, which carries both mutations, was generated and characterized with respect to its thermal stability and affinity.

CD thermal unfolding studies at physiological pH demonstrated a significant rise by 8.6° C. in the melting temperature ($T_m$) for D11vs ($T_m$=63.5° C.) compared to P3D11 ($T_m$=55.2° C.) (FIG. 3C and Table 1). Importantly, the cooperativity of the unfolding transition was much steeper, corresponding to a higher enthalpy of denaturation ($\Delta H_m$) and extrapolated free energy of denaturation ($\Delta G_U$) at standard conditions (25° C.). This is in line with a lower tendency of D11vs to aggregate during incubation at 37° C. compared to P3D11 (FIG. 11D). Additionally, D11vs showed even higher affinity towards hCD98hcED, with a $K_D$ value of 50 pM, due to both faster association and slower dissociation rate constants (FIG. 11E and Table 1).

The enhanced stability and affinity of D11vs can be explained on the basis of the crystal structure solved for the hCD98hcED●P3D11 complex: residue Gly81 was introduced during the initial selection campaign, where it replaced Arg81 present in wtLcn2, thus creating space for tight target binding (FIG. 11C). However, due to the lack of a β-carbon, glycine causes a higher backbone conformational flexibility, which destabilizes the β-barrel [69]. Accordingly, substitution by valine leads to enhanced protein stability while filling a hydrophobic cavity in this region lined by the lipocalin residues Tyr68, Gly81, Phe83 and Leu94 (FIG. 12A), of which Tyr68 also was introduced during the initial selection. Moreover, Val81 increases the contact area with hCD98hcED, which likely contributes to the enhanced affinity (FIG. 12B). On the other hand, replacement of Phe71 by Ser enables the formation of stabilizing hydrogen bonds to Asn174 and Lys50 within the Anticalin (FIG. 12C) Furthermore, the smaller Ser side chain may enable loop #2 of the engineered lipocalin to bend slightly away from the β-barrel axis, thus creating some space for better target binding.

D11vs Binds Human CD98hc on Different Tumor Cell Lines

For in vivo studies in mice, a modified version of D11vs with moderately prolonged plasma half-life was designed using PASylation technology [70]. To this end, a structurally disordered polypeptide comprising in total 200 proline, alanine and serine residues (PAS200) was genetically fused to the C-terminus of the engineered lipocalin, thus increasing its hydrodynamic molecular volume which leads to a retarded kidney filtration (FIG. 17A) [49]. In the context of in vivo imaging applications, previous investigations have shown that fine-tuning of the pharmacokinetics in this manner can boost protein tracer accumulation and tumor contrast [46]. Furthermore, D11vs-PAS200 was equipped with an engineered Cys residue at the C-terminus of the PAS-tag, which enabled homogenous site-specific conjugation of chemical groups for in vitro and in vivo imaging as well as drug delivery (FIG. 17).

The ability of D11vs-PAS200 to bind hCD98hc in a native cellular environment was investigated by cytofluorometry and immunofluorescence microscopy using human cancer cell lines of different origins exhibiting strong expression of this tumor marker. Flow cytometric analysis of the B-cell lymphoma cell lines SU-DHL-4, Raji and Ramos, the prostate carcinoma cells DU-145 and PC-3 and the colorectal adenocarcinoma cell line Caco-2 with Cy5.5-labeled D11vs-PAS200 revealed strong binding of the membrane-associated target protein (FIG. 4A). Competition experiments with excess unlabeled D11vs-PAS200 as well as soluble glycosylated hCD98hcED resulted in signal suppression, hence confirmed high binding specificity of the Anticalin towards native hCD98hc. Immunofluorescence microscopy experiments with D11vs-PAS200-Cy5.5 revealed pronounced membrane and also cytoplasmic staining of Ramos, PC-3 and Caco-2 cancer cells (FIG. 4B-C). Cell staining was effectively blocked when adding a 10-fold molar concentration of the unlabeled lipocalin variant, again confirming its specificity. As expected, no fluorescence staining for any of the tested cell lines was detected when using the Cy5.5-labeled PASylated wtLcn2.

D11vs Shows Strong and Specific Accumulation in Two Human Xenograft Models

The applicability of PASylated D11vs for in vivo targeting of hCD98hc was evaluated by a PET/CT imaging study with the $^{89}$Zr-labeled protein in two murine xenograft tumor models. For this purpose, the human cancer cell lines Ramos (FIG. 13) and PC-3 (FIG. 5) were chosen, considering that CD98hc was described as a promising tumor marker for lymphoma [24] as well as other hematological cancers [17] and is known to be overexpressed in metastatic prostate cancer [23, 71]. In a first study, five female mice each were injected with ~3 MBq of the radiolabeled protein tracer, and PET/CT imaging was performed at time points t=24, 48 and 72 h p.i. (FIGS. 5A and 13A-C). To assess target-specificity of the injected Anticalin, two of these five mice received a 100-fold molar excess of the unlabeled PASylated Anticalin 2 h before $^{89}$Zr-tracer injection. After 24 h, the best imaging contrast and a high accumulation of 3.0±0.3% ID/g was observed for the PC-3 tumors, with decreasing tumor to background contrast after 48 and 72 h. Threshold-based segmentation of the PET images (FIG. 5B) showed a significant (P=0.024) difference in radiotracer accumulation between tracer-injected mice (N=3) and those mice (N=2) which were additionally injected with unlabeled Anticalin. Apart from the strong uptake by the tumors, elimination-related accumulation of radioactivity in liver, kidney and bladder was observed. Furthermore, signals in the joints were detected, which can be explained by accumulation of liberated zirconium caused by the limited complex stability of the linear chelator Dfo [72]. Notably, signals detected in joints and kidneys showed no significant difference in mice with or without blocked CD98hc epitopes, which indicated a tracer-independent uptake into these tissues (FIG. 5B).

Furthermore, the $^{89}$Zr-labeled D11vs-PAS200 tracer allowed good visualization of the Ramos xenografts 24 h p.i., yet at a lower level compared to the PC-3 tumors. Of note, the Ramos xenografts were less well localized and fast growing, which led to blurred imaging signals. Consequently, the PC-3 xenografts were used for further experiments. After in vivo PET imaging, explanted PC-3 tumors were used for autoradiography of tissue cross sections. In this analysis, a homogeneous distribution of the radiotracer within the PC-3 tumor tissue was detected (FIG. 5C), which was strongly reduced in tumors collected from the blocked mice. Concomitant immunohistochemical analysis of vessel distribution (via staining of CD31) as well as hCD98hc abundancy, using cognate antibodies, revealed a well-vascularized tumor with high expression of this tumor marker for both PC-3 and Ramos xenografts (FIG. 5D and Fig. S10). For comparison, one mouse from each cohort was imaged with the small molecule tracers $^{18}$F-fluorodeoxyglucose (FDG) and $^{18}$F-fluoroethyl-L-tyrosine (FET) in PET/CT (FIG. 15). Interestingly, the segmentation-derived values for uptake of FET, which is mainly mediated by the CD98lc Lat-1, was higher in Ramos (15.9±2.9% ID/g) than in PC-3 (9.7±1.4% ID/g), which is in contrast to the observed accumulation of the $^{89}$Zr-Anticalin tracer.

In order to confirm these imaging results and to obtain quantitative data from ex vivo biodistribution experiments at the optimal time point 24 h p.i., a second study using male CB17-SCID mice baring PC-3 tumors was conducted (FIG. 6). Two cohorts with each five mice were injected with either 3.96±0.12 MBq $^{89}$Zr-labeled D11vs-PAS or the protein tracer together with a 250-fold molar amount of the unlabeled PASylated Anticalin (t=−2 h). After 24 h, PET/CT scans were performed, tumors were explanted, subjected to an ex vivo PET scan and, finally, a biodistribution analysis was conducted. PET/CT images of the mice without prior blocking of hCD98hc showed pronounced accumulation of radioactivity in the tumor while the tumors were merely visible in the blocked mice, in line with the ex vivo PET/CT ROI segmentation analysis (P=0.027). Finally, biodistribution study revealed high accumulation of radioactivity (8.6±1.1% ID/g) in the tumor (vs. 5.4±1.1% ID/g in the blocked cohort, P=0.0032), with good tumor-to-blood and tumor-to-muscle ratios of 3.5 and 11.8, respectively. Radioactivity in the excretion-related organs matched the observations above with a particularly pronounced accumulation in the spleen. This can be explained by formation of insoluble Zr-phosphate, which gets quickly absorbed [73]. In summary, the hCD98hc-specific PASylated Anticalin tracer showed high and specific tumor uptake, which may in part be explained by the intracellular accumulation of the residualizing $^{89}$Zr radiometal after targeting the highly expressed and rapidly internalizing tumor marker.

EXAMPLE 3—DISCUSSION

The pathophysiological significance of CD98hc expression in several solid and blood cancers is well established today. Even though also expressed weakly in healthy cells and tissues such as activated lymphocytes, proximal tubules, placenta or testis, strong overexpression of this membrane protein has been shown to correlate with tumor progression and aggressiveness, thus allowing the assessment of disease prognosis, treatment response as well as overall survival in oncologic diseases. Hence, CD98hc constitutes a highly attractive biomedical target for diagnostic as well as therapeutic purposes in oncology. However, no CD98hc-specific reagents for in vivo imaging and only few drug candidates addressing this target are available to date.

To meet this need, an Anticalin was developed with exquisite specificity and high (picomolar) affinity towards the extracellular domain of hCD98hc. The initial Anticalin candidates were selected from a random library based on human lipocalin 2 (Lcn2), an abundant siderophore-binding plasma protein. This previously designed library, which carries an optimally distributed set of randomized amino acid positions within the binding site of the protein scaffold, was successfully applied in previous studies to generate Anticalins against proteinaceous biomedical targets (ED-B, Hsp70, VEGFR-3 or PSMA) [50, 60, 71, 72], peptides (monomeric Aβ) [73] and hapten-type ligands (Colchicin, Y$^{III}$-DTPA, Petrobactin) [50, 60, 71, 72]. The lipocalin variants selected towards hCD98hcED from this naïve Lcn2 library show $K_D$ values already in the pico- to single-digit nanomolar range combined with a stable monomeric behavior, which once again validates the utility of this library.

Based on its association and dissociation rate constants, with a remarkable complex dissociation half-life of ~6 h, P3D11 was chosen as the lead candidate for further characterization and optimization. X-ray structural analysis of its complex with the CD98hc ectodomain revealed deep penetration of loop L2 within the membrane-distal part of CD98hc into the cup-shaped β-barrel of the Anticalin, with a buried total paratope surface area of 1424 Å$^2$. Competition analysis for binding of glycosylated hCD98hc showed that all the selected Anticalins, including P3D11, recognize the same epitope region. P3D11 and P3A12 share a similar set of amino acid exchanges compared with wtLcn2, with 8 identical residues among the 20 randomized positions. Highly similar sequence stretches are seen for loop #1, loop #2 as well as their neighboring β-strands A/B and C/D (FIG. 8A), which also strongly contribute to the protein interface in the hCD98hcED●P3D11 complex (Table 5).

While N-glycosylation has no influence on target affinity of P3D11 (or its improved version D11vs) and P3A12, binding of P1E4 is significantly diminished (~100-fold). This behavior can be explained by minor variations in the mutual orientations between hCD98hcED and the different Anticalins, which could lead to varying sensitivity towards sterically demanding carbohydrate side chains in the neighborhood despite targeting of a similar epitope region (FIG. 2C). Indeed, such a kind of structural paratope plasticity was previously observed for a set of Anticalins directed against the extra-domain B of oncofetal fibronectin [64]. Of note, the clinical-stage mAb IGN523 recognizes the same loop L2 (residues 374-401) of hCD98hcED, also with picomolar affinity [20, 66]. Treatment of patients in a phase I clinical trial did not lead to severe adverse effects, suggesting that this epitope of CD98hc can be targeted safely.

Despite remarkable antigen affinity, which would be suitable for in vivo tumor targeting, especially the Anticalin candidate P3D11 suffered from lower thermal stability and showed pronounced aggregation after prolonged incubation at 37° C. To overcome this obstacle, directed evolution via moderate random mutagenesis was employed in combination with high throughput sorting using a recently developed system for the bacterial surface display of Anticalins [59]. By applying high temperature (37° C.) during protein expression selection of variants showing improved protein folding and stability was forced. With just two additional amino acid substitutions—Phe71Ser and Gly81Val (located in loop #2 and β-strand D, respectively)—the variant D11vs exhibited both increased affinity (approximately three-fold) as well as significantly increased melting temperature (by ~8° C.; cf. Table 1 and FIG. 3C), thus nicely illustrating the power of directed evolution for stability engineering of proteins. (FIG. 11C).

Small animal PET/CT imaging and biodistribution analysis with the plasma half-life optimized and $^{89}$Zr-labeled D11vs radiotracer showed high accumulation in PC-3 xenograft tumors with good imaging contrast. Blocking of CD98hc binding by addition of unlabeled D11 vs-PAS200 reduced tracer accumulation by ~40%. This is in line with in vitro cytofluorometry and immunofluorescence microscopy, where highly specific binding of D11vs on several CD98hc-positive human cancer cell lines, but not on cells with the blocked CD98hc epitope, was evident. Tracer uptake in kidney, liver, spleen and joints was as expected due to the known in vivo release of $^{89}$Zr(IV) from the radiochelator [69, 74]. Superior $^{89}$Zr chelating reagents with higher in vivo stability, as for example fusarinin C, a siderophore-based cyclic chelator derived from *Aspergillus fumigatus* [75, 76], may be an option for future experiments.

In conclusion, human CD98hcED-specific Anticalin was selected and engineered with high affinity and successfully applied it for CD98hc-targeted PET diagnostic imaging. This novel radiotracer showed high tumor uptake in prostate carcinoma as well as B-cell lymphoma xenograft models in mice with excellent tumor visualization. To our knowledge, this is the first in vivo imaging study of CD98hc overexpression on tumor cells described in the literature. Considering the clinical importance of elevated CD98hc expression in several human cancers, this Anticalin constitutes a promising new tool for preclinical and, potentially, clinical applications in oncology.

REFERENCES

1. Cantor J M, Ginsberg M H. CD98 at the crossroads of adaptive immunity and cancer. Journal of cell science. 2012; 125: 1373-82.
2. Fotiadis D, Kanai Y, Palacin M. The SLC3 and SLC7 families of amino acid transporters Molecular aspects of medicine. 2013; 34: 139-58.
3. Kanai Y, Segawa H, Miyamoto K, Uchino H, Takeda E, Endou H. Expression cloning and characterization of a transporter for large neutral amino acids activated by the heavy chain of 4F2 antigen (CD98) The Journal of biological chemistry. 1998; 273: 23629-32.
4. Pineda M, Fernandez E, Torrents D, Estevez R, Lopez C, Camps M, et al. Identification of a membrane protein, LAT-2, that Co-expresses with 4F2 heavy chain, an L-type amino acid transport activity with broad specificity for small and large zwitterionic amino acids The Journal of biological chemistry. 1999; 274: 19738-44.
5. Torrents D, Estevez R, Pineda M, Fernandez E, Lloberas J, Shi Y B, et al. Identification and characterization of a membrane protein (y+L amino acid transporter-1) that associates with 4F2hc to encode the amino acid transport activity y+L. A candidate gene for lysinuric protein intolerance The Journal of biological chemistry. 1998; 273: 32437-45.
6. Broer A, Wagner C A, Lang F, Broer S. The heterodimeric amino acid transporter 4F2hc/y+LAT2 mediates arginine efflux in exchange with glutamine. The Biochemical journal. 2000; 349 Pt 3: 787-95.
7. Fukasawa Y, Segawa H, Kim J Y, Chairoungdua A, Kim D K, Matsuo H, et al. Identification and characterization of a Na(+)-independent neutral amino acid transporter that associates with the 4F2 heavy chain and exhibits substrate selectivity for small neutral D- and L-amino acids. The Journal of biological chemistry. 2000; 275: 9690-8.
8. Sato H, Tamba M, Ishii T, Bannai S. Cloning and expression of a plasma membrane cystine/glutamate exchange transporter composed of two distinct proteins The Journal of biological chemistry. 1999; 274: 11455-8.
9. Nakamura E, Sato M, Yang H, Miyagawa F, Harasaki M, Tomita K, et al. 4F2 (CD98) heavy chain is associated covalently with an amino acid transporter and controls intracellular trafficking and membrane topology of 4F2 heterodimer The Journal of biological chemistry. 1999; 274: 3009-16.
10. Nicklin P, Bergman P, Zhang B, Triantafellow E, Wang H, Nyfeler B, et al. Bidirectional transport of amino acids regulates mTOR and autophagy. Cell. 2009; 136: 521-34.
11. Koppula P, Zhang Y, Zhuang L, Gan B. Amino acid transporter SLC7A11/xCT at the crossroads of regulating redox homeostasis and nutrient dependency of cancer. Cancer communications. 2018; 38: 12.
12. Yoshida G J. Metabolic reprogramming: The emerging concept and associated therapeutic strategies. Journal of experimental & clinical cancer research: CR. 2015; 34: 111.
13. Cantor J M, Ginsberg M H, Rose D M. Integrin-associated proteins as potential therapeutic targets. Immunological reviews. 2008; 223: 236-51.
14. Miyamoto Y J, Mitchell J S, McIntyre B W. Physical association and functional interaction between β1 integrin and CD98 on human T lymphocytes. Molecular immunology. 2003; 39: 739-51.
15. Zent R, Fenczik C A, Calderwood D A, Liu S, Dellos M, Ginsberg M H. Class- and splice variant-specific association of CD98 with integrin β cytoplasmic domains. The Journal of biological chemistry. 2000; 275: 5059-64.
16. Henderson N C, Collis E A, Mackinnon A C, Simpson K J, Haslett C, Zent R, et al. CD98hc (SLC3A2) interaction with β1 integrins is required for transformation. The Journal of biological chemistry. 2004; 279: 54731-41.
17. Bajaj J, Konuma T, Lytle N K, Kwon H Y, Ablack J N, Cantor J M, et al. CD98-mediated adhesive signaling enables the establishment and propagation of acute myelogenous leukemia. Cancer cell. 2016; 30: 792-805.
18. Ye Y, Wang M, Wang B, Yang X-M, Chen Z-N. CD98, a potential diagnostic cancer-related biomarker, and its prognostic impact in colorectal cancer patients. Int J Clin Exp Pathol. 2017; 10: 5418-29.

19. Kaira K, Oriuchi N, Imai H, Shimizu K, Yanagitani N, Sunaga N, et al. CD98 expression is associated with poor prognosis in resected non-small-cell lung cancer with lymph node metastases. Ann Surg Oncol. 2009; 16: 3473-81.
20. Hayes G M, Chinn L, Cantor J M, Cairns B, Levashova Z, Tran H, et al. Antitumor activity of an anti-CD98 antibody. International journal of cancer. 2015; 137: 710-20.
21. El Ansari R, Craze M L, Diez-Rodriguez M, Nolan C C, Ellis I O, Rakha E A, et al. The multifunctional solute carrier 3A2 (SLC3A2) confers a poor prognosis in the highly proliferative breast cancer subtypes. Brit J Cancer. 2018; 118: 1115-22.
22. Furuya M, Horiguchi J, Nakajima H, Kanai Y, Oyama T. Correlation of L-type amino acid transporter 1 and CD98 expression with triple negative breast cancer prognosis. Cancer Sci. 2012; 103: 382-9.
23. Wang Q, Tiffen J, Bailey C G, Lehman M L, Ritchie W, Fazli L, et al. Targeting amino acid transport in metastatic castration-resistant prostate cancer: Effects on cell cycle, cell growth, and tumor development. Journal of the National Cancer Institute. 2013; 105: 1463-73.
24. Salter D M, Krajewski A S, Sheehan T, Turner G, Cuthbert R J, McLean A. Prognostic significance of activation and differentiation antigen expression in B-cell non-Hodgkin's lymphoma The Journal of pathology. 1989; 159: 211-20.
25. Digomann D, Kurth I, Tyutyunnykova A, Chen O, Lock S, Gorodetska I, et al. The CD98 heavy chain is a marker and regulator of head and neck squamous cell carcinoma radiosensitivity. Clinical cancer research: an official journal of the American Association for Cancer Research. 2019.
26. Yang H, Zou W, Li Y, Chen B, Xin X. Bridge linkage role played by CD98hc of anti-tumor drug resistance and cancer metastasis on cisplatin-resistant ovarian cancer cells. Cancer biology & therapy. 2007; 6: 942-7.
27. Kaira K, Ohde Y, Endo M, Nakagawa K, Okumura T, Takahashi T, et al. Expression of 4F2hc (CD98) in pulmonary neuroendocrine tumors Oncology reports. 2011; 26: 931-7.
28. Rietbergen M M, Martens-de Kemp S R, Bloemena E, Witte B I, Brink A, Baatenburg de Jong R J, et al. Cancer stem cell enrichment marker CD98: A prognostic factor for survival in patients with human papillomavirus-positive oropharyngeal cancer. European journal of cancer (Oxford, England: 1990). 2014; 50: 765-73.
29. Prager G W, Poettler M, Schmidinger M, Mazal P R, Susani M, Zielinski C C, et al. CD98hc (SLC3A2), a novel marker in renal cell cancer. European journal of clinical investigation. 2009; 39: 304-10.
30. Isoda A, Kaira K, Iwashina M, Oriuchi N, Tominaga H, Nagamori S, et al. Expression of L-type amino acid transporter 1 (LAT1) as a prognostic and therapeutic indicator in multiple myeloma. Cancer Sci. 2014; 105: 1496-502.
31. Kaira K, Oriuchi N, Imai H, Shimizu K, Yanagitani N, Sunaga N, et al. L-type amino acid transporter 1 and CD98 expression in primary and metastatic sites of human neoplasms. Cancer Sci. 2008; 99: 2380-6.
32. Toyoda M, Kaira K, Shino M, Sakakura K, Takahashi K, Takayasu Y, et al. CD98 as a novel prognostic indicator for patients with stage III/IV hypopharyngeal squamous cell carcinoma Head & neck. 2015; 37: 1569-74.
33. Hayashi K, Anzai N. Novel therapeutic approaches targeting L-type amino acid transporters for cancer treatment. World J Gastrointest Oncol. 2017; 9: 21-9.
34. Salisbury T B, Arthur S. The regulation and function of the L-type amino acid transporter 1 (LAT1) in cancer. Int J Mol Sci. 2018; 19: 2373.
35. Barollo S, Bertazza L, Watutantrige-Fernando S, Censi S, Cavedon E, Galuppini F, et al. Overexpression of L-type amino acid transporter 1 (LAT1) and 2 (LAT2): Novel markers of neuroendocrine tumors. PloS one. 2016; 11: e0156044-e.
36. Sugano K, Maeda K, Ohtani H, Nagahara H, Shibutani M, Hirakawa K. Expression of xCT as a predictor of disease recurrence in patients with colorectal cancer. Anticancer Res. 2015; 35: 677-82.
37. Ji X, Qian J, Rahman S M J, Siska P J, Zou Y, Harris B K, et al. xCT (SLC7A11)-mediated metabolic reprogramming promotes non-small cell lung cancer progression Oncogene. 2018; 37: 5007-19.
38. Kaira K, Oriuchi N, Imai H, Shimizu K, Yanagitani N, Sunaga N, et al. Prognostic significance of L-type amino acid transporter 1 (LAT1) and 4F2 heavy chain (CD98) expression in early stage squamous cell carcinoma of the lung. Cancer Sci. 2009; 100: 249-54.
39. Nakanishi K, Ogata S, Matsuo H, Kanai Y, Endou H, Hiroi S, et al. Expression of LAT1 predicts risk of progression of transitional cell carcinoma of the upper urinary tract. Virchows Arch A. 2007; 451: 681-90.
40. Bixby D, Wieduwilt M J, Akard L P, Khoury H J, Becker P S, Van Der Horst E H, et al. A Phase I Study of IGN523, a Novel Anti-CD98 Monoclonal Antibody in Patients with Relapsed or Refractory Acute Myeloid Leukemia (AML). Blood. 2015; 126: 3809.
41. Wang Q, Hoist J. L-type amino acid transport and cancer: Targeting the mTORC1 pathway to inhibit neoplasia. Am J Cancer Res. 2015; 5: 1281-94.
42. Klasner B D, Krause B J, Beer A J, Drzezga A. PET imaging of gliomas using novel tracers: A sleeping beauty waiting to be kissed. Expert review of anticancer therapy. 2010; 10: 609-13.
43. Ikotun O F, Marquez B V, Huang C, Masuko K, Daiji M, Masuko T, et al. Imaging the L-type amino acid transporter-1 (LAT1) with Zr-89 immunoPET. PloS one. 2013; 8: e77476-e.
44. Hutterer M, Nowosielski M, Putzer D, Jansen N L, Seiz M, Schocke M, et al. [18F]-fluoro-ethyl-L-tyrosine PET: A valuable diagnostic tool in neuro-oncology, but not all that glitters is glioma. Neuro-oncology. 2013; 15: 341-51.
45. Singh N, Ecker G F. Insights into the structure, function, and ligand discovery of the large neutral amino acid transporter 1, LAT1. Int J Mol Sci. 2018; 19.
46. Mendler C T, Friedrich L, Laitinen I, Schlapschy M, Schwaiger M, Wester H J, et al. High contrast tumor imaging with radio-labeled antibody Fab fragments tailored for optimized pharmacokinetics via PASylation. mAbs. 2015; 7: 96-109.
47. Richter A, Eggenstein E, Skerra A. Anticalins: Exploiting a non-Ig scaffold with hypervariable loops for the engineering of binding proteins. FEBS letters. 2014; 588: 213-8.
48. Rothe C, Skerra A. Anticalin® proteins as therapeutic agents in human diseases. BioDrugs. 2018; 32: 233-43.
49. Schlapschy M, Binder U, Borger C, Theobald I, Wachinger K, Kisling S, et al. PASylation:
A biological alternative to PEGylation for extending the plasma half-life of pharmaceutically active proteins. Protein engineering, design & selection: PEDS. 2013; 26: 489-501.

50. Gebauer M, Schiefner A, Matschiner G, Skerra A. Combinatorial design of an Anticalin directed against the extra-domain b for the specific targeting of oncofetal fibronectin Journal of molecular biology. 2013; 425: 780-802.

51. Friedrich L, Kornberger P, Mendler C T, Multhoff G, Schwaiger M, Skerra A. Selection of an Anticalin® against the membrane form of Hsp70 via bacterial surface display and its theranostic application in tumour models. Biological chemistry. 2018; 399: 235-52.

52. Mueller U, Darowski N, Fuchs M R, Forster R, Hellmig M, Paithankar K S, et al. Facilities for macromolecular crystallography at the Helmholtz-Zentrum Berlin. J Synchrotron Radiat. 2012; 19: 442-9.

53. Kabsch W. XDS. Acta Crystallographica Section D Biological Crystallography. 2010; 66: 125-32.

54. McCoy A J, Grosse-Kunstleve R W, Adams P D, Winn M D, Storoni L C, Read R J. Phaser crystallographic software. J Appl Crystallogr. 2007; 40: 658-74.

55. Fort J, de la Ballina L R, Burghardt H E, Ferrer-Costa C, Turnay J, Ferrer-Orta C, et al. The structure of human 4F2hc ectodomain provides a model for homodimerization and electrostatic interaction with plasma membrane. The Journal of biological chemistry. 2007; 282: 31444-52.

56. Emsley P, Lohkamp B, Scott W G, Cowtan K. Features and development of Coot. Acta Crystallographica Section D Biological Crystallography. 2010; 66: 486-501.

57. Murshudov G N, Skubak P, Lebedev A A, Pannu N S, Steiner R A, Nicholls R A, et al. REFMAC5 for the refinement of macromolecular crystal structures. Acta Crystallographica Section D Biological Crystallography. 2011; 67: 355-67.

58. Painter J, Merritt E A. TLSMD web server for the generation of multi-group TLS models. J Appl Crystallogr. 2006; 39: 109-11.

59. Barkovskiy M, Ilyukhina E, Dauner M, Eichinger A, Skerra A. An engineered lipocalin that tightly complexes the plant poison colchicine for use as antidote as well as bioanalytical applications. Biological chemistry. 2018.

60. Binder U, Matschiner G, Theobald I, Skerra A. High-throughput sorting of an Anticalin library via EspP-mediated functional display on the *Escherichia coli* cell surface. Journal of molecular biology. 2010; 400: 783-802.

61. Costa J, Grabenhorst E, Nimtz M, Conradt H S. Stable expression of the Golgi form and secretory variants of human fucosyltransferase III from BHK-21 cells. The Journal of biological chemistry. 1997; 272: 11613-21.

62. Schlehuber S, Skerra A. Tuning ligand affinity, specificity, and folding stability of an engineered lipocalin variant—a so-called 'anticalin'—using a molecular random approach. Biophys Chem. 2002; 96: 213-28.

63. Vosjan M J, Perk L R, Visser G W, Budde M, Jurek P, Kiefer G E, et al. Conjugation and radiolabeling of monoclonal antibodies with zirconium-89 for PET imaging using the bifunctional chelate p-isothiocyanatobenzyl-desferrioxamine. Nat Protoc. 2010; 5: 739-43.

64. Wollscheid B, Bausch-Fluck D, Henderson C, O'Brien R, Bibel M, Schiess R, et al. Mass-spectrometric identification and relative quantification of N-linked cell surface glycoproteins Nature biotechnology. 2009; 27: 378-86.

65. Barinka C, Ptacek J, Richter A, Novakova Z, Morath V, Skerra A. Selection and characterization of Anticalins targeting human prostate-specific membrane antigen (PSMA) Protein engineering, design & selection: PEDS. 2016; 29: 105-15.

66. Beckett D, Kovaleva E, Schatz P J. A minimal peptide substrate in biotin holoenzyme synthetase-catalyzed biotinylation Protein science: a publication of the Protein Society. 1999; 8: 921-9.

67. Schiefner A, Gebauer M, Richter A, Skerra A. Anticalins reveal high plasticity in the mode of complex formation with a common tumor antigen. Structure (London, England: 1993). 2018; 26: 649-56.e3.

68. Lippincott J, Van der Horst E T H, Zachwieja J, Tran H. Anti-CD98 antibodies and methods of use thereof. In: Organization WIP, editor.; 2013.

69. Matthews B W, Nicholson H, Becktel W J. Enhanced protein thermostability from site-directed mutations that decrease the entropy of unfolding. Proc Natl Acad Sci USA. 1987; 84: 6663-7.

70. Binder U, Skerra A. PASylation®: A versatile technology to extend drug delivery. Curr Opin Colloid Interface Sci. 2017; 31: 10-7.

71. Papetti M, Herman I M. Controlling tumor-derived and vascular endothelial cell growth: Role of the 4Ff2 cell surface antigen. Am J Pathol. 2001; 159: 165-78.

72. Fischer G, Seibold U, Schirrmacher R, Wangler B, Wangler C. (89)Zr, a radiometal nuclide with high potential for molecular imaging with PET: Chemistry, applications and remaining challenges. Molecules (Basel, Switzerland). 2013; 18: 6469-90.

73. Abou D S, Ku T, Smith-Jones P M. In vivo biodistribution and accumulation of 89Zr in mice Nuclear medicine and biology. 2011; 38: 675-81.

74. Richter A, Skerra A. Anticalins directed against vascular endothelial growth factor receptor 3 (VEGFR-3) with picomolar affinities show potential for medical therapy and in vivo imaging. Biological chemistry. 2017; 398: 39-55.

75. Rauth S, Hinz D, Borger M, Uhrig M, Mayhaus M, Riemenschneider M, et al. High-affinity Anticalins with aggregation-blocking activity directed against the Alzheimer beta-amyloid peptide. The Biochemical journal. 2016; 473: 1563-78.

76. Mendler C T, Gehring T, Wester H J, Schwaiger M, Skerra A. (89)Zr-labeled versus (124)I-labeled αHER2 Fab with optimized plasma half-life for high-contrast tumor imaging in vivo. Journal of nuclear medicine: official publication, Society of Nuclear Medicine. 2015; 56: 1112-8.

77. Summer D, Garousi J, Oroujeni M, Mitran B, Andersson K G, Vorobyeva A, et al. Cyclic versus noncyclic chelating scaffold for (89)Zr-labeled ZEGFR:2377 Affibody bioconjugates targeting epidermal growth factor receptor overexpression. Molecular pharmaceutics. 2018; 15: 175-85.

78. Summer D, Rangger C, Klingler M, Laverman P, Franssen G M, Lechner B E, et al. Exploiting the concept of multivalency with (68)Ga- and (89)Zr-labeled Fusarinine C-Minigastrin Bioconjugates for targeting CCK2R expression. Contrast media & molecular imaging. 2018; 2018: 3171794.

The invention claimed is:

1. A cluster of differentiation 98 heavy chain (CD98hc)-specific binding protein, wherein the CD98hc-specific binding protein is a lipocalin 2 (Lcn2)-derived binding protein, and wherein the CD98hc-specific binding protein
   (a) comprises or consists of an amino acid sequence as represented in formula I:

QDSTSD($X_1$)($X_2$)PAPPLSKVPLQQNFQDNQF(Q/H)GKWY($X_3$)VG($X_4$)AG($X_5$)($X_6$)($X_7$)($X_8$)($X_9$)E($X_{10}$)($X_{11}$)($X_{12}$)($X_{13}$)($X_{14}$)($X_{15}$)M($X_{16}$)ATIYELKEDKS(Y/F)NVT($X_{17}$)V($X_{18}$)($X_{19}$)($X_{20}$)($X_{21}$)(K/T)KC($X_{22}$)(Y/N)($X_{23}$)($X_{24}$)($X_{25}$)(T/S)($X_{26}$)VPG(C/S)QPGE(F/Y)(T/N)($X_{27}$)G(N/K)I($X_{28}$)S(Y/R/G/A)P($X_{29}$)($X_{30}$)($X_{31}$)S($X_{32}$)L($X_{33}$)RVVSTNYNQ(H/Y)A(M/L)VF($X_{34}$)K($X_{35}$)(V/E)($X_{36}$)($X_{37}$)N($X_{38}$)E($X_{39}$)($X_{40}$)($X_{41}$)I($X_{42}$)L($X_{43}$)GRTKELTSELKE(N/I/Y)FIRFSKSLGLPE($X_{44}$)($X_{45}$)IVFPVPIDQCIDG, wherein
   ($X_1$) is L;
   ($X_2$) is I;
   ($X_3$) is V;
   ($X_4$) is R;
   ($X_5$) is N;
   ($X_6$) is L or T;
   ($X_7$) is G;
   ($X_8$) is L;
   ($X_9$) is R;
   ($X_{10}$) is D;
   ($X_{11}$) is K;
   ($X_{12}$) is D;
   ($X_{13}$) is P;
   ($X_{14}$) is A or G;
   ($X_{15}$) is K;
   ($X_{16}$) is F;
   ($X_{17}$) is Y;
   ($X_{18}$) is W;
   ($X_{19}$) is F or S;
   ($X_{20}$) is D or G;
   ($X_{21}$) is L or Q;
   ($X_{22}$) is K or M;
   ($X_{23}$) is S;
   ($X_{24}$) is I;
   ($X_{25}$) is H, G or V;
   ($X_{26}$) is F;
   ($X_{27}$) is L;
   ($X_{28}$) is K;
   ($X_{29}$) is G;
   ($X_{30}$) is H, R or Q;
   ($X_{31}$) is T;
   ($X_{32}$) is W;
   ($X_{33}$) is V;
   ($X_{34}$) is F;
   ($X_{35}$) is W or S;
   ($X_{36}$) is G or T;
   ($X_{37}$) is Q;
   ($X_{38}$) is R;
   ($X_{39}$) is N, G or E;
   ($X_{40}$) is F;
   ($X_{41}$) is A;
   ($X_{42}$) is T;
   ($X_{43}$) is Y;
   ($X_{44}$) is N; and
   ($X_{45}$) is H; or
   (b) comprises or consists of an amino acid sequence which is at least 80% identical to the amino acid sequence of (a), provided that amino acid positions ($X_1$) to ($X_{45}$) are maintained as defined in item (a).

2. The CD98hc-specific binding protein of claim 1, wherein the CD98hc-specific binding protein
   (a) comprises or consists of the amino acid sequence of (SEQ ID NO: 14)
QDSTSDLIPAPPLSKVPLQQNFQDNQF<u>HGKWYVVGIAGNSMLREDKDPF</u>

<u>KMTATIYELKEDKSYNVTRVRFDDKKCLYRILTFVPGSQPGEFTLGNIK</u>

<u>SRPGVVTSWLVRVVSTNYNQH</u>AMVFFKRVHQNRETFWITLYGRTKELTS

ELKENFIRFSKSLGLPENHIVFPVPIDQCIDG;

or
   (b) comprises or consists of an amino acid sequence which is at least 80% identical to the amino acid sequence of (a), provided that the underlined amino acids are maintained as defined in item (a).

3. The CD98hc-specific binding protein of claim 1, wherein the CD98hc-specific binding protein comprises or consists of
   the amino acid sequence of any one of SEQ ID NOs 2 to 13.

4. A protein conjugate or fusion protein comprising the CD98hc-specific binding protein of claim 1.

5. The protein conjugate or fusion protein of claim 4, wherein the CD98hc-specific binding protein is conjugated to or is part of a fusion protein wherein the fusion partner is
   (a) a fluorescent dye or a fluorescent protein,
   (b) a radionuclide,
   (c) a toxic compound,
   (d) a photosensitizer,
   (e) an enzyme or truncated version thereof,
   (f) a membrane protein or functional fragment thereof retaining the enzyme function,
   (g) a contrast agent,
   (h) a cytokine,
   (i) a chemokine,
   (j) a pro-coagulant factor,
   (k) an acetylcholineesterase inhibitor,
   (l) an inhibitor of Aβ aggregation,
   (m) a nucleic acid molecule, or
   (n) a nanoparticle.

6. The protein conjugate or fusion protein of claim 4, wherein the CD98hc-specific binding protein is conjugated to a binding protein.

7. A pharmaceutical composition or a diagnostic composition comprising
   (i) the CD98hc-specific binding protein of claim 1; or
   (ii) a protein conjugate or fusion protein comprising the CD98hc-specific binding protein of (i).

8. The CD98hc-specific binding protein of claim 1 for use in therapy and/or diagnosis of a tumor, wherein the tumor is located in the brain and/or the spinal cord.

9. The protein conjugate or fusion protein of claim 4 for use in therapy and/or diagnosis of a tumor, wherein the tumor is located in the brain and/or the spinal cord.

10. The protein conjugate or fusion protein of claim 6, wherein the binding protein is selected from an antibody or immunoglobulin, an antibody fragment, and an antibody mimetic.

11. The protein conjugate or fusion protein of claim 10, wherein the antibody mimetic is selected from the group consisting of an Anticalin, Affibody, Adnectin, DARPin, Avimer, Nanofitin, Affilin, β-Wrapin, ADAPT, Monobody, RasIn, FingR, Pronectin, Centyrin, Affimer, Adhiron, Affitin, αRep, Repebody, i-body, Fynomer, and a Kunitz domain protein.

* * * * *

UNITED STATES PATENT AND TRADEMARK OFFICE
CERTIFICATE OF CORRECTION

| | | |
|---|---|---|
| PATENT NO. | : 12,173,038 B2 | Page 1 of 1 |
| APPLICATION NO. | : 17/440520 | |
| DATED | : December 24, 2024 | |
| INVENTOR(S) | : Skerra et al. | |

It is certified that error appears in the above-identified patent and that said Letters Patent is hereby corrected as shown below:

In the Claims

In Claim 2, Column 92, Line 16, delete "SRPGVVT" and insert -- SRPGWT --, therefor.

Signed and Sealed this
Twenty-first Day of October, 2025

John A. Squires
*Director of the United States Patent and Trademark Office*

SEQUENCE LISTING

<160> NUMBER OF SEQ ID NOS: 30

<210> SEQ ID NO 1
<211> LENGTH: 419
<212> TYPE: PRT
<213> ORGANISM: Homo sapiens
<220> FEATURE:
<223> OTHER INFORMATION: huCD98hcED

<400> SEQUENCE: 1

```
Glu Leu Pro Ala Gln Lys Trp Trp His Thr Gly Ala Leu Tyr Arg Ile
1               5                   10                  15

Gly Asp Leu Gln Ala Phe Gln Gly His Gly Ala Gly Asn Leu Ala Gly
            20                  25                  30

Leu Lys Gly Arg Leu Asp Tyr Leu Ser Ser Leu Lys Val Lys Gly Leu
        35                  40                  45

Val Leu Gly Pro Ile His Lys Asn Gln Lys Asp Asp Val Ala Gln Thr
    50                  55                  60

Asp Leu Leu Gln Ile Asp Pro Asn Phe Gly Ser Lys Glu Asp Phe Asp
65                  70                  75                  80

Ser Leu Leu Gln Ser Ala Lys Lys Lys Ser Ile Arg Val Ile Leu Asp
                85                  90                  95

Leu Thr Pro Asn Tyr Arg Gly Glu Asn Ser Trp Phe Ser Thr Gln Val
            100                 105                 110

Asp Thr Val Ala Thr Lys Val Lys Asp Ala Leu Glu Phe Trp Leu Gln
        115                 120                 125

Ala Gly Val Asp Gly Phe Gln Val Arg Asp Ile Glu Asn Leu Lys Asp
    130                 135                 140

Ala Ser Ser Phe Leu Ala Glu Trp Gln Asn Ile Thr Lys Gly Phe Ser
145                 150                 155                 160

Glu Asp Arg Leu Leu Ile Ala Gly Thr Asn Ser Ser Asp Leu Gln Gln
                165                 170                 175

Ile Leu Ser Leu Leu Glu Ser Asn Lys Asp Leu Leu Leu Thr Ser Ser
            180                 185                 190

Tyr Leu Ser Asp Ser Gly Ser Thr Gly Glu His Thr Lys Ser Leu Val
        195                 200                 205

Thr Gln Tyr Leu Asn Ala Thr Gly Asn Arg Trp Cys Ser Trp Ser Leu
    210                 215                 220

Ser Gln Ala Arg Leu Leu Thr Ser Phe Leu Pro Ala Gln Leu Leu Arg
225                 230                 235                 240

Leu Tyr Gln Leu Met Leu Phe Thr Leu Pro Gly Thr Pro Val Phe Ser
                245                 250                 255

Tyr Gly Asp Glu Ile Gly Leu Asp Ala Ala Leu Pro Gly Gln Pro
            260                 265                 270

Met Glu Ala Pro Val Met Leu Trp Asp Glu Ser Ser Phe Pro Asp Ile
        275                 280                 285

Pro Gly Ala Val Ser Ala Asn Met Thr Val Lys Gly Gln Ser Glu Asp
    290                 295                 300

Pro Gly Ser Leu Leu Ser Leu Phe Arg Arg Leu Ser Asp Gln Arg Ser
305                 310                 315                 320

Lys Glu Arg Ser Leu Leu His Gly Asp Phe His Ala Phe Ser Ala Gly
                325                 330                 335

Pro Gly Leu Phe Ser Tyr Ile Arg His Trp Asp Gln Asn Glu Arg Phe
            340                 345                 350

Leu Val Val Leu Asn Phe Gly Asp Val Gly Leu Ser Ala Gly Leu Gln
```

```
                355                 360                 365
Ala Ser Asp Leu Pro Ala Ser Ala Ser Leu Pro Ala Lys Ala Asp Leu
        370                 375                 380

Leu Leu Ser Thr Gln Pro Gly Arg Glu Glu Gly Ser Pro Leu Glu Leu
385                 390                 395                 400

Glu Arg Leu Lys Leu Glu Pro His Glu Gly Leu Leu Leu Arg Phe Pro
                405                 410                 415

Tyr Ala Ala

<210> SEQ ID NO 2
<211> LENGTH: 178
<212> TYPE: PRT
<213> ORGANISM: Artificial Sequence
<220> FEATURE:
<223> OTHER INFORMATION: hCD98hcED-D11vs

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Arg Ala Gly Asn Thr Gly Leu Arg Glu Asp Lys Asp Pro
            35                  40                  45

Gly Lys Met Phe Ala Thr Ile Tyr Glu Leu Lys Glu Asp Lys Ser Tyr
    50                  55                  60

Asn Val Thr Tyr Val Trp Ser Gly Gln Lys Lys Cys Met Tyr Ser Ile
65                  70                  75                  80

Val Thr Phe Val Pro Gly Ser Gln Pro Gly Glu Phe Thr Leu Gly Asn
                85                  90                  95

Ile Lys Ser Ala Pro Gly Arg Thr Ser Trp Leu Val Arg Val Val Ser
            100                 105                 110

Thr Asn Tyr Asn Gln His Ala Met Val Phe Phe Lys Ser Val Thr Gln
    115                 120                 125

Asn Arg Glu Gly Phe Ala Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: hCD98hcED-D11.1

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Arg Ala Gly Asn Thr Gly Leu Arg Glu Asp Lys Asp Pro
            35                  40                  45

Gly Lys Met Phe Ala Thr Ile Tyr Glu Leu Lys Glu Asp Lys Ser Tyr
    50                  55                  60
```

```
Asn Val Thr Tyr Val Trp Ser Gly Gln Lys Lys Cys Met Tyr Ser Ile
 65                  70                  75                  80

Val Thr Phe Val Pro Gly Ser Gln Pro Gly Glu Phe Thr Leu Gly Asn
                 85                  90                  95

Ile Lys Ser Ala Pro Gly Gln Thr Ser Trp Leu Val Arg Val Val Ser
            100                 105                 110

Thr Asn Tyr Asn Gln His Ala Met Val Phe Phe Lys Ser Val Thr Gln
                115                 120                 125

Asn Arg Glu Gly Phe Ala Ile Thr Leu Tyr Gly Arg Thr Lys Glu Leu
            130                 135                 140

Thr Ser Glu Leu Lys Glu Ile Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: Artificial Sequence
<220> FEATURE:
<223> OTHER INFORMATION: hCD98hcED-D11.2

<400> SEQUENCE: 4

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Arg Ala Gly Asn Thr Gly Leu Arg Glu Asp Lys Asp Pro
            35                  40                  45

Gly Lys Met Phe Ala Thr Ile Tyr Glu Leu Lys Glu Asp Lys Ser Tyr
        50                  55                  60

Asn Val Thr Tyr Val Trp Ser Gly Gln Lys Lys Cys Met Tyr Ser Ile
 65                  70                  75                  80

Val Thr Phe Val Pro Gly Ser Gln Pro Gly Glu Phe Thr Leu Gly Asn
                 85                  90                  95

Ile Lys Ser Ala Pro Gly Arg Thr Ser Trp Leu Val Arg Val Val Ser
            100                 105                 110

Thr Asn Tyr Asn Gln His Ala Leu Val Phe Phe Lys Ser Val Thr Gln
                115                 120                 125

Asn Arg Glu Gly Phe Ala Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial Sequence
<220> FEATURE:
<223> OTHER INFORMATION: hCD98hcED-D11.3

<400> SEQUENCE: 5
```

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Arg Ala Gly Asn Thr Gly Leu Arg Glu Asp Lys Asp Pro
            35                  40                  45

Gly Lys Met Phe Ala Thr Ile Tyr Glu Leu Lys Glu Asp Lys Ser Tyr
        50                  55                  60

Asn Val Thr Tyr Val Trp Phe Gly Gln Lys Lys Cys Met Tyr Ser Ile
65                  70                  75                  80

Val Thr Phe Val Pro Gly Ser Gln Pro Gly Glu Phe Thr Leu Gly Asn
                85                  90                  95

Ile Lys Ser Ala Pro Gly Arg Thr Ser Trp Leu Val Arg Val Val Ser
                100                 105                 110

Thr Asn Tyr Asn Gln Tyr Ala Met Val Phe Phe Lys Ser Val Thr Gln
            115                 120                 125

Asn Arg Glu Gly Phe Ala Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: Artificial Sequence
<220> FEATURE:
<223> OTHER INFORMATION: hCD98hcED-D11.4

<400> SEQUENCE: 6

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Arg Ala Gly Asn Thr Gly Leu Arg Glu Asp Lys Asp Pro
            35                  40                  45

Gly Lys Met Phe Ala Thr Ile Tyr Glu Leu Lys Glu Asp Lys Ser Phe
        50                  55                  60

Asn Val Thr Tyr Val Trp Phe Gly Gln Lys Lys Cys Met Tyr Ser Ile
65                  70                  75                  80

Val Thr Phe Val Pro Gly Ser Gln Pro Gly Glu Phe Thr Leu Gly Asn
                85                  90                  95

Ile Lys Ser Ala Pro Gly Arg Thr Ser Trp Leu Val Arg Val Val Ser
                100                 105                 110

Thr Asn Tyr Asn Gln His Ala Met Val Phe Phe Lys Ser Val Thr Gln
            115                 120                 125

Asn Arg Glu Gly Phe Ala Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: Artificial Sequence
<220> FEATURE:
<223> OTHER INFORMATION: hCD98hcED-D11.5

<400> SEQUENCE: 7

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Thr Gly Leu Arg Glu Asp Lys Asp Pro
        35                  40                  45

Gly Lys Met Phe Ala Thr Ile Tyr Glu Leu Lys Glu Asp Lys Ser Tyr
    50                  55                  60

Asn Val Thr Tyr Val Trp Phe Gly Gln Lys Lys Cys Met Asn Ser Ile
65                  70                  75                  80

Val Thr Phe Val Pro Gly Ser Gln Pro Gly Glu Phe Thr Leu Gly Asn
                85                  90                  95

Ile Lys Ser Ala Pro Gly Arg Thr Ser Trp Leu Val Arg Val Val Ser
            100                 105                 110

Thr Asn Tyr Asn Gln Tyr Ala Met Val Phe Phe Lys Ser Val Thr Gln
        115                 120                 125

Asn Arg Glu Gly Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 8
<211> LENGTH: 178
<212> TYPE: PRT
<213> ORGANISM: Artificial Sequence
<220> FEATURE:
<223> OTHER INFORMATION: hCD98hcED-D11.6

<400> SEQUENCE: 8

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Thr Gly Leu Arg Glu Asp Lys Asp Pro
        35                  40                  45

Gly Lys Met Phe Ala Thr Ile Tyr Glu Leu Lys Glu Asp Lys Ser Tyr
    50                  55                  60

Asn Val Thr Tyr Val Trp Phe Gly Gln Lys Lys Cys Met Tyr Ser Ile
65                  70                  75                  80

Val Thr Phe Val Pro Gly Ser Gln Pro Gly Glu Phe Thr Leu Gly Asn
                85                  90                  95

Ile Lys Ser Ala Pro Gly Arg Thr Ser Trp Leu Val Arg Val Val Ser
            100                 105                 110

Thr Asn Tyr Asn Gln Tyr Ala Met Val Phe Phe Lys Ser Glu Thr Gln
        115                 120                 125
```

```
Asn Arg Glu Gly Phe Ala Ile Thr Leu Tyr Gly Arg Thr Lys Glu Leu
            130                 135                 140

Thr Ser Glu Leu Lys Glu Tyr Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
<212> TYPE: PRT
<213> ORGANISM: Artificial Sequence
<220> FEATURE:
<223> OTHER INFORMATION: hCD98hcED-D11.7

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Thr Gly Leu Arg Glu Asp Lys Asp Pro
        35                  40                  45

Gly Lys Met Phe Ala Thr Ile Tyr Glu Leu Lys Glu Asp Lys Ser Tyr
    50                  55                  60

Asn Val Thr Tyr Val Trp Phe Gly Gln Lys Lys Cys Met Tyr Ser Ile
65                  70                  75                  80

Val Thr Phe Val Pro Gly Ser Gln Pro Gly Glu Phe Thr Leu Gly Asn
                85                  90                  95

Ile Lys Ser Ala Pro Gly Arg Thr Ser Trp Leu Val Arg Val Val Ser
            100                 105                 110

Thr Asn Tyr Asn Gln His Ala Met Val Phe Phe Lys Ser Val Thr Gln
        115                 120                 125

Asn Arg Glu Glu Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: Artificial Sequence
<220> FEATURE:
<223> OTHER INFORMATION: hCD98hcED-D11.8

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Thr Gly Leu Arg Glu Asp Lys Asp Pro
        35                  40                  45

Gly Lys Met Phe Ala Thr Ile Tyr Glu Leu Lys Glu Asp Lys Ser Tyr
    50                  55                  60
```

```
Asn Val Thr Tyr Val Trp Ser Gly Gln Lys Lys Cys Met Tyr Ser Ile
 65                  70                  75                  80

Val Ser Phe Val Pro Gly Ser Gln Pro Gly Glu Tyr Asn Leu Gly Asn
                 85                  90                  95

Ile Lys Ser Ala Pro Gly Arg Thr Ser Trp Leu Val Arg Val Val Ser
            100                 105                 110

Thr Asn Tyr Asn Gln His Ala Met Val Phe Phe Lys Ser Val Thr Gln
        115                 120                 125

Asn Arg Glu Gly Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 178
<212> TYPE: PRT
<213> ORGANISM: Artificial Sequence
<220> FEATURE:
<223> OTHER INFORMATION: hCD98hcED-D11.9

<400> SEQUENCE: 11

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Arg Ala Gly Asn Thr Gly Leu Arg Glu Asp Lys Asp Pro
             35                  40                  45

Gly Lys Met Phe Ala Thr Ile Tyr Glu Leu Lys Glu Asp Lys Ser Tyr
         50                  55                  60

Asn Val Thr Tyr Val Trp Ser Gly Gln Thr Lys Cys Met Tyr Ser Ile
 65                  70                  75                  80

Val Thr Phe Val Pro Gly Ser Gln Pro Gly Glu Phe Thr Leu Gly Asn
                 85                  90                  95

Ile Lys Ser Ala Pro Gly Arg Thr Ser Trp Leu Val Arg Val Val Ser
            100                 105                 110

Thr Asn Tyr Asn Gln His Ala Met Val Phe Phe Lys Ser Val Thr Gln
        115                 120                 125

Asn Arg Glu Gly Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 12
<211> LENGTH: 178
<212> TYPE: PRT
<213> ORGANISM: Artificial Sequence
<220> FEATURE:
<223> OTHER INFORMATION: hCD98hcED-P3D11

<400> SEQUENCE: 12

Gln Asp Ser Thr Ser Asp Leu Ile Pro Ala Pro Pro Leu Ser Lys Val
```

```
  1               5                  10                  15
Pro Leu Gln Gln Asn Phe Gln Asp Asn Gln Phe His Gly Lys Trp Tyr
             20                  25                  30

Val Val Gly Arg Ala Gly Asn Thr Gly Leu Arg Glu Asp Lys Asp Pro
             35                  40                  45

Gly Lys Met Phe Ala Thr Ile Tyr Glu Leu Lys Glu Asp Lys Ser Tyr
             50                  55                  60

Asn Val Thr Tyr Val Trp Phe Gly Gln Lys Lys Cys Met Tyr Ser Ile
 65                  70                  75                  80

Gly Thr Phe Val Pro Gly Ser Gln Pro Gly Glu Phe Thr Leu Gly Asn
                 85                  90                  95

Ile Lys Ser Ala Pro Gly Arg Thr Ser Trp Leu Val Arg Val Val Ser
             100                 105                 110

Thr Asn Tyr Asn Gln His Ala Met Val Phe Phe Lys Ser Val Thr Gln
             115                 120                 125

Asn Arg Glu Gly Phe Ala Ile Thr Leu Tyr Gly Arg Thr Lys Glu Leu
             130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                 165                 170                 175

Asp Gly

<210> SEQ ID NO 13
<211> LENGTH: 178
<212> TYPE: PRT
<213> ORGANISM: Artificial Sequence
<220> FEATURE:
<223> OTHER INFORMATION: hCD98hcED-P3A12

<400> SEQUENCE: 13

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
             20                  25                  30

Val Val Gly Arg Ala Gly Asn Leu Gly Leu Arg Glu Asp Lys Asp Pro
             35                  40                  45

Ala Lys Met Phe Ala Thr Ile Tyr Glu Leu Lys Glu Asp Lys Ser Tyr
             50                  55                  60

Asn Val Thr Tyr Val Trp Phe Asp Leu Lys Lys Cys Lys Tyr Ser Ile
 65                  70                  75                  80

His Thr Phe Val Pro Gly Ser Gln Pro Gly Glu Phe Thr Leu Gly Lys
                 85                  90                  95

Ile Lys Ser Gly Pro Gly His Thr Ser Trp Leu Val Arg Val Val Ser
             100                 105                 110

Thr Asn Tyr Asn Gln His Ala Met Val Phe Phe Lys Trp Val Gly Gln
             115                 120                 125

Asn Arg Glu Asn Phe Ala Ile Thr Leu Tyr Gly Arg Thr Lys Glu Leu
             130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                 165                 170                 175

Asp Gly
```

<210> SEQ ID NO 14
<211> LENGTH: 178
<212> TYPE: PRT
<213> ORGANISM: Artificial Sequence
<220> FEATURE:
<223> OTHER INFORMATION: hCD98hcED-P1E4

<400> SEQUENCE: 14

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ile Ala Gly Asn Ser Met Leu Arg Glu Asp Lys Asp Pro
        35                  40                  45

Phe Lys Met Thr Ala Thr Ile Tyr Glu Leu Lys Glu Asp Lys Ser Tyr
    50                  55                  60

Asn Val Thr Arg Val Arg Phe Asp Asp Lys Lys Cys Leu Tyr Arg Ile
65                  70                  75                  80

Leu Thr Phe Val Pro Gly Ser Gln Pro Gly Glu Phe Thr Leu Gly Asn
                85                  90                  95

Ile Lys Ser Arg Pro Gly Trp Thr Ser Trp Leu Val Arg Val Val Ser
            100                 105                 110

Thr Asn Tyr Asn Gln His Ala Met Val Phe Phe Lys Arg Val His Gln
        115                 120                 125

Asn Arg Glu Thr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 15
<211> LENGTH: 1260
<212> TYPE: DNA
<213> ORGANISM: Homo sapiens
<220> FEATURE:
<223> OTHER INFORMATION: huCD98hcED

<400> SEQUENCE: 15

```
gaactgcctg cacagaaatg gtggcatacc ggtgcactgt atcgtattgg tgatctgcag    60
gcatttcagg gtcatggtgc aggtaatctg caggtctga aaggtcgtct ggattatctg   120
agcagcctga agttaaaggt tctggttctg gtccgattc acaaaaatca gaaagatgat   180
gttgcacaga ccgatctgct gcagattgat ccgaattttg gtagcaaaga gatttcgat   240
agcctgctgc agtcagccaa aaaaaaaagc attcgtgtta ttctggatct gaccccgaat   300
tatcgtggtg aaaatagctg gtttagcacc caggttgata ccgttgcaac caaagtgaaa   360
gatgcactgg aatttttggct gcaggcaggc gttgatggtt ttcaggttcg tgatattgaa   420
aatctgaaag acgcaagcag ctttctggca gaatggcaga atattaccaa aggctttagc   480
gaagatcgtc tgctgattgc aggcaccaat agcagcgatc tgcaacaaat tctgagcctg   540
ctggaaagca ataaagacct gctgctgacc agcagctatc tgagcgatag cggtagcacc   600
ggtgaacata ctaaaagcct ggttacccag tatctgaatg caaccggtaa tcgttggtgt   660
agctggtcac tgagccaggc acgcctgctg acctcatttc tgcctgccca gctgctgcgc   720
```

```
ctgtatcaac tgatgctgtt taccctgcct ggtacaccgg ttttagcta tggtgatgaa      780 attggtctgg atgcagcagc actgcctggt cagccgatgg aagcaccggt tatgctgtgg      840
gatgaaagca gttttccgga tattccgggt gcagttagcg caaatatgac cgtgaaaggt      900
cagagtgaag atccgggtag tctgctgagc ctgtttcgtc gtctgagtga tcagcgtagt      960
aaagaacgtt cactgctgca tggtgatttt catgcattta gcgcaggtcc gggtctgttt     1020
agctatattc gtcattggga tcagaatgaa cgttttctgg ttgttctgaa ctttggtgat     1080
gttggtctga gtgcaggtct gcaggccagt gatctgcctg caagcgcaag cctgccagca     1140
aaagcggatc tgctgctgag cacccagcct ggtcgtgaag aaggtagtcc gctggaactg     1200
gaacgtctga aactggaacc gcatgaagga ctgctgctgc gttttccgta tgcagcataa     1260
```

```
<210> SEQ ID NO 16
<211> LENGTH: 178
<212> TYPE: PRT
<213> ORGANISM: Artificial Sequence
<220> FEATURE:
<223> OTHER INFORMATION: Formula I
<220> FEATURE:
<221> NAME/KEY: VARIANT
<222> LOCATION: 7
<223> OTHER INFORMATION: L
<220> FEATURE:
<221> NAME/KEY: VARIANT
<222> LOCATION: 8
<223> OTHER INFORMATION: I
<220> FEATURE:
<221> NAME/KEY: VARIANT
<222> LOCATION: 28
<223> OTHER INFORMATION: Q or H
<220> FEATURE:
<221> NAME/KEY: VARIANT
<222> LOCATION: 33
<223> OTHER INFORMATION: V
<220> FEATURE:
<221> NAME/KEY: VARIANT
<222> LOCATION: 36
<223> OTHER INFORMATION: R
<220> FEATURE:
<221> NAME/KEY: VARIANT
<222> LOCATION: 39
<223> OTHER INFORMATION: N
<220> FEATURE:
<221> NAME/KEY: VARIANT
<222> LOCATION: 40
<223> OTHER INFORMATION: L or T
<220> FEATURE:
<221> NAME/KEY: VARIANT
<222> LOCATION: 41
<223> OTHER INFORMATION: G
<220> FEATURE:
<221> NAME/KEY: VARIANT
<222> LOCATION: 42
<223> OTHER INFORMATION: L
<220> FEATURE:
<221> NAME/KEY: VARIANT
<222> LOCATION: 43
<223> OTHER INFORMATION: R
<220> FEATURE:
<221> NAME/KEY: VARIANT
<222> LOCATION: 45
<223> OTHER INFORMATION: D
<220> FEATURE:
<221> NAME/KEY: VARIANT
<222> LOCATION: 46
<223> OTHER INFORMATION: K
<220> FEATURE:
<221> NAME/KEY: VARIANT
<222> LOCATION: 47
<223> OTHER INFORMATION: D
<220> FEATURE:
<221> NAME/KEY: VARIANT
```

```
<222> LOCATION: 48
<223> OTHER INFORMATION: P
<220> FEATURE:
<221> NAME/KEY: VARIANT
<222> LOCATION: 49
<223> OTHER INFORMATION: A or G
<220> FEATURE:
<221> NAME/KEY: VARIANT
<222> LOCATION: 50
<223> OTHER INFORMATION: K
<220> FEATURE:
<221> NAME/KEY: VARIANT
<222> LOCATION: 52
<223> OTHER INFORMATION: F
<220> FEATURE:
<221> NAME/KEY: VARIANT
<222> LOCATION: 64
<223> OTHER INFORMATION: Y or F
<220> FEATURE:
<221> NAME/KEY: VARIANT
<222> LOCATION: 68
<223> OTHER INFORMATION: Y
<220> FEATURE:
<221> NAME/KEY: VARIANT
<222> LOCATION: 70
<223> OTHER INFORMATION: W
<220> FEATURE:
<221> NAME/KEY: VARIANT
<222> LOCATION: 71
<223> OTHER INFORMATION: F or S
<220> FEATURE:
<221> NAME/KEY: VARIANT
<222> LOCATION: 72
<223> OTHER INFORMATION: D or G
<220> FEATURE:
<221> NAME/KEY: VARIANT
<222> LOCATION: 73
<223> OTHER INFORMATION: L or Q
<220> FEATURE:
<221> NAME/KEY: VARIANT
<222> LOCATION: 74
<223> OTHER INFORMATION: K or T
<220> FEATURE:
<221> NAME/KEY: VARIANT
<222> LOCATION: 77
<223> OTHER INFORMATION: K or M
<220> FEATURE:
<221> NAME/KEY: VARIANT
<222> LOCATION: 78
<223> OTHER INFORMATION: Y or N
<220> FEATURE:
<221> NAME/KEY: VARIANT
<222> LOCATION: 79
<223> OTHER INFORMATION: S
<220> FEATURE:
<221> NAME/KEY: VARIANT
<222> LOCATION: 80
<223> OTHER INFORMATION: I
<220> FEATURE:
<221> NAME/KEY: VARIANT
<222> LOCATION: 81
<223> OTHER INFORMATION: H, G or V
<220> FEATURE:
<221> NAME/KEY: VARIANT
<222> LOCATION: 82
<223> OTHER INFORMATION: T or S
<220> FEATURE:
<221> NAME/KEY: VARIANT
<222> LOCATION: 83
<223> OTHER INFORMATION: F
<220> FEATURE:
<221> NAME/KEY: VARIANT
<222> LOCATION: 87
<223> OTHER INFORMATION: C or S
<220> FEATURE:
<221> NAME/KEY: VARIANT
<222> LOCATION: 92
<223> OTHER INFORMATION: F or Y
<220> FEATURE:
```

```
<221> NAME/KEY: VARIANT
<222> LOCATION: 93
<223> OTHER INFORMATION: T or N
<220> FEATURE:
<221> NAME/KEY: VARIANT
<222> LOCATION: 94
<223> OTHER INFORMATION: L
<220> FEATURE:
<221> NAME/KEY: VARIANT
<222> LOCATION: 96
<223> OTHER INFORMATION: N or K
<220> FEATURE:
<221> NAME/KEY: VARIANT
<222> LOCATION: 98
<223> OTHER INFORMATION: K
<220> FEATURE:
<221> NAME/KEY: VARIANT
<222> LOCATION: 100
<223> OTHER INFORMATION: Y, R, G or A
<220> FEATURE:
<221> NAME/KEY: VARIANT
<222> LOCATION: 102
<223> OTHER INFORMATION: G
<220> FEATURE:
<221> NAME/KEY: VARIANT
<222> LOCATION: 103
<223> OTHER INFORMATION: H, R or Q
<220> FEATURE:
<221> NAME/KEY: VARIANT
<222> LOCATION: 104
<223> OTHER INFORMATION: T
<220> FEATURE:
<221> NAME/KEY: VARIANT
<222> LOCATION: 106
<223> OTHER INFORMATION: W
<220> FEATURE:
<221> NAME/KEY: VARIANT
<222> LOCATION: 108
<223> OTHER INFORMATION: V
<220> FEATURE:
<221> NAME/KEY: VARIANT
<222> LOCATION: 118
<223> OTHER INFORMATION: H or Y
<220> FEATURE:
<221> NAME/KEY: VARIANT
<222> LOCATION: 120
<223> OTHER INFORMATION: M or L
<220> FEATURE:
<221> NAME/KEY: VARIANT
<222> LOCATION: 123
<223> OTHER INFORMATION: F
<220> FEATURE:
<221> NAME/KEY: VARIANT
<222> LOCATION: 125
<223> OTHER INFORMATION: W or S
<220> FEATURE:
<221> NAME/KEY: VARIANT
<222> LOCATION: 126
<223> OTHER INFORMATION: V or E
<220> FEATURE:
<221> NAME/KEY: VARIANT
<222> LOCATION: 127
<223> OTHER INFORMATION: G or T
<220> FEATURE:
<221> NAME/KEY: VARIANT
<222> LOCATION: 128
<223> OTHER INFORMATION: Q
<220> FEATURE:
<221> NAME/KEY: VARIANT
<222> LOCATION: 130
<223> OTHER INFORMATION: R
<220> FEATURE:
<221> NAME/KEY: VARIANT
<222> LOCATION: 132
<223> OTHER INFORMATION: N, G or E
<220> FEATURE:
<221> NAME/KEY: VARIANT
<222> LOCATION: 133
<223> OTHER INFORMATION: F
```

-continued

```
<220> FEATURE:
<221> NAME/KEY: VARIANT
<222> LOCATION: 134
<223> OTHER INFORMATION: A
<220> FEATURE:
<221> NAME/KEY: VARIANT
<222> LOCATION: 136
<223> OTHER INFORMATION: T
<220> FEATURE:
<221> NAME/KEY: VARIANT
<222> LOCATION: 138
<223> OTHER INFORMATION: Y
<220> FEATURE:
<221> NAME/KEY: VARIANT
<222> LOCATION: 151
<223> OTHER INFORMATION: N, I or Y
<220> FEATURE:
<221> NAME/KEY: VARIANT
<222> LOCATION: 164
<223> OTHER INFORMATION: N
<220> FEATURE:
<221> NAME/KEY: VARIANT
<222> LOCATION: 165
<223> OTHER INFORMATION: H

<400> SEQUENCE: 16

Gln Asp Ser Thr Ser Asp Xaa Xaa Pro Ala Pro Pro Leu Ser Lys Val
1               5                   10                  15

Pro Leu Gln Gln Asn Phe Gln Asp Asn Gln Phe Xaa Gly Lys Trp Tyr
            20                  25                  30

Xaa Val Gly Xaa Ala Gly Xaa Xaa Xaa Xaa Glu Xaa Xaa Xaa Xaa
        35                  40                  45

Xaa Xaa Met Xaa Ala Thr Ile Tyr Glu Leu Lys Glu Asp Lys Ser Xaa
    50                  55                  60

Asn Val Thr Xaa Val Xaa Xaa Xaa Xaa Lys Cys Xaa Xaa Xaa Xaa
65                  70                  75                  80

Xaa Xaa Xaa Val Pro Gly Xaa Gln Pro Gly Glu Xaa Xaa Gly Xaa
                85                  90                  95

Ile Xaa Ser Xaa Pro Xaa Xaa Xaa Ser Xaa Leu Xaa Arg Val Val Ser
            100                 105                 110

Thr Asn Tyr Asn Gln Xaa Ala Xaa Val Phe Xaa Lys Xaa Xaa Xaa Xaa
            115                 120                 125

Asn Xaa Glu Xaa Xaa Xaa Ile Xaa Leu Xaa Gly Arg Thr Lys Glu Leu
130                 135                 140

Thr Ser Glu Leu Lys Glu Xaa Phe Ile Arg Phe Ser Lys Ser Leu Gly
145                 150                 155                 160

Leu Pro Glu Xaa Xaa Ile Val Phe Pro Val Pro Ile Asp Gln Cys Ile
                165                 170                 175

Asp Gly

<210> SEQ ID NO 17
<211> LENGTH: 534
<212> TYPE: DNA
<213> ORGANISM: Artificial Sequence
<220> FEATURE:
<223> OTHER INFORMATION: hCD98hcED-D11vs

<400> SEQUENCE: 17
caggactcca cctcagacct gatcccagcc ccacctctga gcaaggtccc tctgcagcag      60
aacttccagg acaaccaatt ccatgggaaa tggtatgtcg tgggccgtgc cggaaatacc     120
ggactgcgtg aggataagga tccgggaaaa atgttcgcga ccatttacga gttgaaagaa     180
gataaatcat ataacgtcac ctacgtgtgg tctggacaaa agaaatgcat gtacagcatt     240
``` gtaaccttg tgccggggag ccagccgggc gagtttactt taggcaatat taaaagtgca    300
ccgggccgta catcatggtt ggtccgcgtc gtgagcacca actacaacca gcatgccatg    360
gtgttcttca agagcgtgac ccagaaccgc gagggatttg caatcacact gtacgggcgc    420
acgaaagaac tgacaagcga gctgaaggaa aactttatcc gctttccaa atctctgggc    480 ctccctgaaa accacatcgt cttccctgtc ccaatcgacc agtgtatcga cggc    534

<210> SEQ ID NO 18
<211> LENGTH: 534
<212> TYPE: DNA
<213> ORGANISM: Artificial Sequence
<220> FEATURE:
<223> OTHER INFORMATION: hCD98hcED-D11.1

<400> SEQUENCE: 18
caggactcca cctcagacct gatcccagcc ccacctctga gcaaggtccc tctgcagcag    60
aacttccagg acaaccaatt ccatgggaaa tggtatgtcg tgggccgtgc cggaaatacc    120
ggactgcgtg aggataagga tccgggaaaa atgttcgcga ccatttacga gttgaaagaa    180
gataaatcat ataacgtcac ctacgtgtgg tctggacaaa agaaatgcat gtacagcatt    240 gtaaccttg tgccggggag ccagccgggc gagtttactt taggcaatat taaaagtgca    300
ccgggccaaa catcatggtt ggtccgcgtc gtgagcacca actacaacca gcatgccatg    360
gtgttcttca agagcgtgac ccagaaccgc gagggatttg caatcacact gtacgggcgc    420
acgaaagaac tgacaagcga gctgaaggaa atttttatcc gcttttccaa atctctgggc    480
ctccctgaaa accacatcgt cttccctgtc ccaatcgacc agtgtatcga cggc    534

<210> SEQ ID NO 19
<211> LENGTH: 534
<212> TYPE: DNA
<213> ORGANISM: Artificial Sequence
<220> FEATURE:
<223> OTHER INFORMATION: hCD98hcED-D11.2

<400> SEQUENCE: 19
caggactcca cctcagacct gatcccagcc ccacctctga gcaaggtccc tctgcagcag    60
aacttccagg acaaccaatt ccatgggaaa tggtatgtcg tgggccgtgc cggaaatacc    120
ggactgcgtg aggataagga tccgggaaaa atgttcgcga ccatttacga gttgaaagaa    180
gataaatcat ataacgtcac ctacgtgtgg tctggacaaa agaaatgcat gtacagcatt    240 gtaaccttg tgccggggag ccagccgggc gagtttactt taggcaatat taaaagtgca    300
ccgggccgta catcatggtt ggtccgcgtc gtgagcacca actacaacca gcatgccttg    360 gtgttttca agagcgtgac ccagaaccgc gagggatttg caatcacact gtacgggcgc    420
acgaaagaac tgacaagcga gctgaaggaa aatttttatac gcttttccaa atctctgggc    480
ctccctgaaa accacatcgt cttccctgtc ccaatcgacc agtgtatcga cggc    534

<210> SEQ ID NO 20
<211> LENGTH: 534
<212> TYPE: DNA
<213> ORGANISM: Artificial Sequence
<220> FEATURE:
<223> OTHER INFORMATION: hCD98hcED-D11.3

<400> SEQUENCE: 20
caggactcca cctcagacct gatcccagcc ccacctctga gcaaggtccc tctgcagcag    60

| | |
|---|---|
| aacttccagg acaaccaatt ccatgggaaa tggtatgtcg tgggccgtgc cggaaatacc | 120 |
| ggactgcgtg aggataagga tccgggaaaa atgttcgcga ccatttacga gttgaaagaa | 180 |
| gataaatcat ataacgtcac ctacgtgtgg tttggacaaa agaaatgcat gtacagcatt | 240 |
| gtaacctttg tgccggggag ccagccgggc gagtttactt taggcaatat taaaagtgca | 300 |
| ccgggccgta catcatggtt ggtccgcgtc gtgagcacca actacaacca gtatgccatg | 360 |
| gtgttcttca agagcgtgac ccagaaccgc gagggatttg caatcacact gtacgggcgc | 420 |
| acgaaagaac tgacaagcga gctgaaggaa aattttatcc gcttttccaa atctctgggc | 480 |
| ctccctgaaa accacatcgt cttccctgtc ccaatcgacc agtgtatcga cggc | 534 |

<210> SEQ ID NO 21
<211> LENGTH: 534
<212> TYPE: DNA
<213> ORGANISM: Artificial Sequence
<220> FEATURE:
<223> OTHER INFORMATION: hCD98hcED-D11.4

<400> SEQUENCE: 21

| | |
|---|---|
| caggactcca cctcagacct gatcccagcc ccacctctga gcaaggtccc tctgcagcag | 60 |
| aacttccagg acaaccaatt ccatgggaaa tggtatgtcg tgggccgtgc cggaaatacc | 120 |
| ggactgcgtg aggataagga tccgggaaaa atgttcgcga ccatttacga gttgaaagaa | 180 |
| gataaatcat ttaacgtcac ctacgtgtgg tttggacaaa agaaatgcat gtacagcatt | 240 |
| gtaacctttg tgccggggag ccagccgggc gagtttactt taggcaatat taaaagtgca | 300 |
| ccgggccgta catcatggtt ggtccgcgtc gtgagcacca actacaacca gcatgccatg | 360 |
| gtgttcttca agagcgtgac ccagaaccgc gagggatttg caatcacact gtacgggcgc | 420 |
| acgaaagaac tgacaagcga gctgaaggaa aattttatcc gcttttccaa atctctgggc | 480 |
| ctccctgaaa accacatcgt cttccctgtc ccaatcgacc agtgtatcga cggc | 534 |

<210> SEQ ID NO 22
<211> LENGTH: 534
<212> TYPE: DNA
<213> ORGANISM: Artificial Sequence
<220> FEATURE:
<223> OTHER INFORMATION: hCD98hcED-D11.5

<400> SEQUENCE: 22

| | |
|---|---|
| caggactcca cctcagacct gatcccagcc ccacctctga gcaaggtccc tctgcagcag | 60 |
| aacttccagg acaaccaatt ccatgggaaa tggtatgtcg tgggccgtgc cggaaatacc | 120 |
| ggactgcgtg aggataagga tccgggaaaa atgttcgcga ccatttacga gttgaaagaa | 180 |
| gataaatcat ataacgtcac ctacgtgtgg tttggacaaa agaaatgcat gaacagcatt | 240 |
| gtaacctttg tgccggggag ccagccgggc gagtttactt taggcaatat taaaagtgca | 300 |
| ccgggccgta catcatggtt ggtccgcgtc gtgagcacca actacaacca gtatgccatg | 360 |
| gtgttcttca agagcgtgac ccagaaccgc gagggatttg caatcacact gtacgggcgc | 420 |
| acgaaagaac tgacaagcga gctgaaggaa aattttatcc gcttttccaa atctctgggc | 480 |
| ctccctgaaa accacatcgt cttccctgtc ccaatcgacc agtgtatcga cggc | 534 |

<210> SEQ ID NO 23
<211> LENGTH: 534
<212> TYPE: DNA
<213> ORGANISM: Artificial Sequence
<220> FEATURE:
<223> OTHER INFORMATION: hCD98hcED-D11.6

<400> SEQUENCE: 23

```
caggactcca cctcagacct gatcccagcc ccacctctga gcaaggtccc tctgcagcag    60
aacttccagg acaaccaatt ccatgggaaa tggtatgtcg tgggccgtgc cggaaatacc   120
ggactgcgtg aggataagga tccgggaaaa atgttcgcga ccatttacga gttgaaagaa   180
gataaatcat ataacgtcac ctacgtgtgg tttggacaaa agaaatgcat gtacagcatt   240
gtaacctttg tgccggggag ccagccgggc gagtttactt taggcaatat taaaagtgca   300
ccgggccgta catcatggtt ggtccgcgtc gtgagcacca actacaacca gtatgccatg   360
gtgttcttca gagcgagac ccagaaccgc gagggatttg caatcacact gtacgggcgc   420
acgaaagaac tgacaagcga gctgaaggaa tattttatcc gcttttccaa atctctgggc   480
ctccctgaaa accacatcgt cttccctgtc ccaatcgacc agtgtatcga cggc         534
```

<210> SEQ ID NO 24
<211> LENGTH: 534
<212> TYPE: DNA
<213> ORGANISM: Artificial Sequence
<220> FEATURE:
<223> OTHER INFORMATION: hCD98hcED-D11.7

<400> SEQUENCE: 24

```
caggactcca cctcagacct gatcccagcc ccacctctga gcaaggtccc tctgcagcag    60
aacttccagg acaaccaatt ccatgggaaa tggtatgtcg tgggccgtgc cggaaatacc   120
ggactgcgtg aggataagga tccgggaaaa atgttcgcga ccatttacga gttgaaagaa   180
gataaatcat ataacgtcac ctacgtgtgg tttggacaaa agaaatgcat gtacagcatt   240
gtaacctttg tgccggggag ccagccgggc gagtttactt taggcaatat taaaagtgca   300
ccgggccgta catcatggtt ggtccgcgtc gtgagcacca actacaacca gcatgccatg   360
gtgttcttca gagcgtgac ccagaaccgc gaggaatttg caatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 25
<211> LENGTH: 534
<212> TYPE: DNA
<213> ORGANISM: Artificial Sequence
<220> FEATURE:
<223> OTHER INFORMATION: hCD98hcED-D11.8

<400> SEQUENCE: 25

```
caggactcca cctcagacct gatcccagcc ccacctctga gcaaggtccc tctgcagcag    60
aacttccagg acaaccaatt ccatgggaaa tggtatgtcg tgggccgtgc cggaaatacc   120
ggactgcgtg aggataagga tccgggaaaa atgttcgcga ccatttacga gttgaaagaa   180
gataaatcat ataacgtcac ctacgtgtgg tctggacaaa agaaatgcat gtacagcatt   240
gtatcctttg tgccggggag ccagccgggc gagtataatt taggcaatat taaaagtgca   300
ccaggccgta catcatggtt ggtccgcgtc gtgagcacca actacaacca gcatgccatg   360
gtgttcttca gagcgtgac ccagaaccgc gagggatttg caatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 26

```
<211> LENGTH: 534
<212> TYPE: DNA
<213> ORGANISM: Artificial Sequence
<220> FEATURE:
<223> OTHER INFORMATION: hCD98hcED-D11.9

<400> SEQUENCE: 26
caggactcca cctcagacct gatcccagcc ccacctctga gcaaggtccc tctgcagcag      60
aacttccagg acaaccaatt ccatgggaaa tggtatgtcg tgggccgtgc cggaaatacc     120
ggactgcgtg aggataagga tccgggaaaa atgttcgcga ccatttacga gttgaaagaa     180
gataaatcat ataacgtcac ctacgtgtgg tctggacaaa cgaaatgcat gtacagcatt     240
gtaacctttg tgccggggag tcagccgggc gagtttactt taggcaatat taaaagtgca     300
ccgggccgta catcatggtt ggtccgcgtc gtgagcacca actacaacca gcatgccatg     360
gtgttcttca agagcgtgac ccagaaccgc gagggatttg caatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534

<210> SEQ ID NO 27
<211> LENGTH: 534
<212> TYPE: DNA
<213> ORGANISM: Artificial Sequence
<220> FEATURE:
<223> OTHER INFORMATION: hCD98hcED-P3D11

<400> SEQUENCE: 27
caggactcca cctcagacct gatcccagcc ccacctctga gcaaggtccc tctgcagcag      60
aacttccagg acaaccaatt ccatgggaaa tggtatgtcg tgggccgtgc cggaaatacc     120
ggactgcgtg aggataagga tccgggaaaa atgttcgcga ccatttacga gttgaaagaa     180
gataaatcat ataacgtcac ctacgtgtgg tttggacaaa agaaatgcat gtacagcatt     240
ggaacctttg tgccggggag ccagccgggc gagtttactt taggcaatat taaaagtgca     300
ccgggccgta catcatggtt ggtccgcgtc gtgagcacca actacaacca gcatgccatg     360
gtgttcttca agagcgtgac ccagaaccgc gagggatttg caatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534

<210> SEQ ID NO 28
<211> LENGTH: 534
<212> TYPE: DNA
<213> ORGANISM: Artificial Sequence
<220> FEATURE:
<223> OTHER INFORMATION: hCD98hcED-P3A12

<400> SEQUENCE: 28
caggactcca cctcagacct gatcccagcc ccacctctga gcaaggtccc tctgcagcag      60
aacttccagg acaaccaatt ccatgggaaa tggtatgtcg tgggccgtgc cggaaatctg     120
ggactgcgtg aggataagga tccggcaaaa atgttcgcga ccatttacga gttgaaagaa     180
gataaatcat ataacgtcac ctacgtgtgg tttgacctga agaaatgcaa atacagcatt     240
cacacctttg tgccggggag ccagccgggc gagtttactt taggcaaaat taaaagtgga     300
ccgggccaca catcatggtt ggtccgcgtc gtgagcacca actacaacca gcatgccatg     360
gtgttcttca agtgggtggg acagaaccgc gagaattttg caatcacact gtacgggcgc     420
acgaaagaac tgacaagcga gctgaaggaa aattttatcc gcttttccaa atctctgggc     480
```

```
ctccctgaaa accacatcgt cttccctgtc ccaatcgacc agtgtatcga cggc        534
```

<210> SEQ ID NO 29
<211> LENGTH: 534
<212> TYPE: DNA
<213> ORGANISM: Artificial Sequence
<220> FEATURE:
<223> OTHER INFORMATION: hCD98hcED-P1E4

<400> SEQUENCE: 29

```
caggactcca cctcagacct gatcccagcc ccacctctga gcaaggtccc tctgcagcag    60
aacttccagg acaaccaatt ccatgggaaa tggtatgtcg tgggcatcgc cggaaatagc   120
atgctgcgtg aggataagga tccgttcaaa atgaccgcga ccatttacga gttgaaagaa   180
gataaatcat ataacgtcac ccgtgtgcgt tttgacgaca gaaatgcct gtaccgtatt    240
ctgacctttg tgccggggag ccagccgggc gagtttactt taggcaatat taaaagtcgt   300
ccgggctgga catcatggtt ggtccgcgtc gtgagcacca actacaacca gcatgccatg   360
gtgttcttca agcgtgtgca ccagaaccgc gagacctttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc        534
```

<210> SEQ ID NO 30
<211> LENGTH: 178
<212> TYPE: PRT
<213> ORGANISM: Homo sapiens
<220> FEATURE:
<223> OTHER INFORMATION: Wild type Lcn2

<400> SEQUENCE: 30

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly